US012391737B2

(12) United States Patent
Haebel et al.

(10) Patent No.: US 12,391,737 B2
(45) Date of Patent: Aug. 19, 2025

(54) SOLUBLE NPY2 RECEPTOR AGONISTS

(71) Applicant: Boehringer Ingelheim International GmbH, Ingelheim am Rhein (DE)

(72) Inventors: Peter Wilhelm Haebel, Mittelbiberach (DE); Albert Brennauer, Biberach an der Riss (DE); Stefan Peters, Biberach an der Riss (DE); Charlotte Stahl Madsen, Måløv (DK); Søren Ljungberg Pedersen, Borup (DK)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 463 days.

(21) Appl. No.: 17/394,522

(22) Filed: Aug. 5, 2021

(65) Prior Publication Data

US 2022/0041678 A1 Feb. 10, 2022

(30) Foreign Application Priority Data

Aug. 7, 2020 (EP) .................................... 20189966

(51) Int. Cl.

*C07K 14/575* (2006.01)
*A61K 38/22* (2006.01)
*A61K 45/06* (2006.01)
*A61P 3/04* (2006.01)
*A61K 38/00* (2006.01)

(52) U.S. Cl.

CPC ............ *C07K 14/575* (2013.01); *A61K 38/22* (2013.01); *A61K 45/06* (2013.01); *A61P 3/04* (2018.01); *A61K 38/00* (2013.01)

(58) Field of Classification Search

None
See application file for complete search history.

(56) References Cited

U.S. PATENT DOCUMENTS

| | | | | |
|---|---|---|---|---|
| 12,054,525 | B2 * | 8/2024 | Haebel | A61K 38/22 |
| 2007/0135351 | A1 | 6/2007 | Conde-Knape et al. | |
| 2008/0207512 | A1 | 8/2008 | Roth et al. | |
| 2009/0105122 | A1 | 4/2009 | Lumb et al. | |
| 2010/0323955 | A1 | 12/2010 | Roth et al. | |
| 2013/0281373 | A1 | 10/2013 | Klein et al. | |
| 2015/0152150 | A1 | 6/2015 | Oestergaard et al. | |
| 2018/0155406 | A1 | 6/2018 | Bossart et al. | |
| 2019/0002520 | A1 | 1/2019 | Oh et al. | |
| 2019/0207505 | A1 | 7/2019 | Ramadass et al. | |
| 2019/0231850 | A1 | 8/2019 | Acosta et al. | |
| 2020/0014514 | A1 | 1/2020 | Gao et al. | |
| 2020/0140514 | A1 | 5/2020 | Briere et al. | |
| 2022/0041678 | A1 | 2/2022 | Haebel et al. | |
| 2023/0340039 | A1 * | 10/2023 | Haebel | A61K 38/2271 |

FOREIGN PATENT DOCUMENTS

| | | | |
|---|---|---|---|
| CO | 7500115 | A2 | 1/2016 |
| WO | 2005077072 | A2 | 8/2005 |
| WO | 2005089789 | A2 | 9/2005 |
| WO | 2005077072 | | 11/2005 |
| WO | 2006049681 | A2 | 5/2006 |
| WO | 2006066024 | A2 | 6/2006 |
| WO | 2008152403 | | 6/2008 |
| WO | 2008101017 | | 8/2008 |
| WO | 2008101017 | A2 | 8/2008 |
| WO | 2008152403 | A1 | 12/2008 |
| WO | 2009064298 | | 5/2009 |
| WO | 2009064298 | A1 | 5/2009 |
| WO | 2010007251 | | 6/2010 |
| WO | 2010070251 | A1 | 6/2010 |
| WO | 2010070252 | | 6/2010 |
| WO | 2010070252 | A1 | 6/2010 |
| WO | 2010070253 | | 6/2010 |
| WO | 2010070253 | A1 | 6/2010 |
| WO | 2010070255 | | 6/2010 |
| WO | 2010070255 | A1 | 6/2010 |
| WO | 2011006497 | | 1/2011 |
| WO | 2011006497 | A1 | 1/2011 |
| WO | 2011033068 | A1 | 3/2011 |
| WO | 2011058165 | A1 | 5/2011 |
| WO | 2011060630 | A1 | 5/2011 |
| WO | 2011160630 | | 12/2011 |
| WO | 2011160633 | | 12/2011 |
| WO | 2011160633 | A1 | 12/2011 |
| WO | 2012168430 | | 12/2012 |
| WO | 2012168430 | A2 | 12/2012 |
| WO | 2012168431 | A2 | 12/2012 |
| WO | 2012168432 | | 12/2012 |
| WO | 2012168432 | A1 | 12/2012 |
| WO | 2013092703 | | 6/2013 |
| WO | 2013092703 | A2 | 6/2013 |
| WO | 2013164483 | | 11/2013 |

(Continued)

OTHER PUBLICATIONS

Ahn, Advances in experimental medicine and biology, Amylin Pharma, vol. 611, 2009.
Batterham, Inhibition of food intake, New England J. Med, vol. 349, 2003.
Bak, Physicochemical and Formulation Developability Assessment, The AAPS Journal, vol. 17, 2015.
Roux, Elimination and exchange of trifluoroacetate, J. Pept. Sci. Vol. 14, 2008.
Beck-Sickinger, Complete L-Alanine scan of Neuropeptide Y, Ero. J, Biochem, vol. 225, 1994.
European Search Report for 01-3446-WO-1mailed Feb. 22, 2021.
Koglin, Novel modified and radiolabelled neuropeptide Y analogies to study Y-receptor subtypes, Science Direct, vol. 38, 2004.
Henry, Vitamin B12 Conjugation, Endocrinology, vol. 156, 2015.

(Continued)

*Primary Examiner* — Maury A Audet
(74) *Attorney, Agent, or Firm* — Mary Breen Smith

(57) ABSTRACT

The invention relates to PYY analogues having alanine at position 4, lysine at position 7, QRY as the C-terminal end and a half-life extending group. The analogues of the invention are soluble around pH 6 and 7. The invention also relates to pharmaceutical compositions comprising such PYY analogues, and to the medical use of the analogues.

18 Claims, No Drawings

Specification includes a Sequence Listing.

(56) References Cited

FOREIGN PATENT DOCUMENTS

| | | | |
|---|---|---|---|
| WO | 2013164483 | A1 | 11/2013 |
| WO | 2014041195 | A1 | 3/2014 |
| WO | 2015067716 | | 5/2014 |
| WO | 2014178018 | A1 | 6/2014 |
| WO | 2015040182 | | 3/2015 |
| WO | 2015040182 | A2 | 3/2015 |
| WO | 2015055801 | A1 | 4/2015 |
| WO | 2015055802 | A2 | 4/2015 |
| WO | 2015067716 | A1 | 5/2015 |
| WO | 2015071229 | | 5/2015 |
| WO | 2015071229 | A1 | 5/2015 |
| WO | 2015071355 | A1 | 5/2015 |
| WO | 2016146739 | | 9/2016 |
| WO | 2016146739 | A1 | 9/2016 |
| WO | 2016166289 | A1 | 10/2016 |
| WO | 2016198624 | | 12/2016 |
| WO | 2016198624 | A1 | 12/2016 |
| WO | 2016198682 | A1 | 12/2016 |
| WO | 2017116204 | | 12/2016 |
| WO | 2017116205 | | 7/2017 |
| WO | 2017192538 | A1 | 11/2017 |
| WO | 2018046719 | | 3/2018 |
| WO | 2018046719 | A1 | 3/2018 |
| WO | 2018081370 | | 5/2018 |
| WO | 2018081370 | A1 | 5/2018 |
| WO | 2018081375 | A1 | 5/2018 |
| WO | 2018100134 | | 6/2018 |
| WO | 2018100134 | A1 | 6/2018 |
| WO | 2018100135 | | 6/2018 |
| WO | 2018172390 | A1 | 9/2018 |
| WO | 2018224630 | A1 | 12/2018 |
| WO | 2019110982 | A1 | 6/2019 |
| WO | 2019207505 | A1 | 10/2019 |
| WO | 2020092191 | A1 | 5/2020 |
| WO | 2021094259 | A1 | 5/2021 |

OTHER PUBLICATIONS

Corrigan, Salt forms, Encyclopedia of Pharma Tech., 2007.

Fields, Principles and Practice of Solid Phase Peptide Synthesis, Advances in Molecular Biology, 2002.

Berge, Pharmaceutical Salts, J. of Pharma Sciences, vol. 66, 1977.

U.S. Appl. No. 18/751,723, filed Jun. 24, 2024, Inventor Peter Haebel (The cited pending U.S. application is stored in the USPTO IFW system (MPEP 609.04(a)(II)(C)).

Ahn, John S. et al. "Synthesis and Biological Evaluation of PYY(3-36) Analogs Substituted with Alanine" (2009), Advances in Experimental Medicine and Biology, vol. 611, 515-516.

Bak, Annette et al. "Physicochemical and Formulaton Developability Assessment for Therapeutic Peptide Delivery—A Primer" (2015) The AAPS Journal, vol. 17, No. 1, 144-155.

Batterham, Rachel L. et la. Inhibition of Food Intake in Obese Subjects by Peptide YY3-36, (2003) The New England Journal of Medicine, vol. 349, 10, 941-948.

Beck-Sickinger, Annette G. et al. "Complete L-alanine scan of neuropeptide Y reveals ligands binding to Y1 and Y2 receptors with distinguished conformations" (1994), Eur. J. Biochem, vol. 225, 947-958.

Berge, Stephen, M et al. "Pharmaceutical Salts" (1977) Journal of Pharmaceutical Sciences, vol. 66, No. 1, 1-19.

Bujak, Emil et al. "Reformatting of scFv Antibodies into the scFv-Fc Format and their Downstream Purification", Chapter 20, Monoclonal Antibodies: Methods and Protocols, (2014) vol. 1131, 315-334.

Corrigan, Owen I. "Salt Forms: Pharmaceutical Aspects" (2007) Encyclopedia of Pharmaceutical Technology, 3177-3186.

Fields, Gregg B. et al. "Principles and Practice of Solid-Phase Peptide Synthesis" (2002) Synthetic Peptides, A User's Guide, Second Edition, 93-219.

Gershoni, Jonathan et al. "Epitope Mapping, The First Step in Developing Epitope-Based Vaccines" (2007) Drug Development, vol. 21, 145-156.

Henry, Kelly et al, "Vitamin B12 Conjugation of Peptide YY3-36 Decreases Food Intake, Compared to native Peptide-YY3-36 Upon Subcutaneous Administration in Male Rats" (2015) Endocrinology, vol. 156, 1739-1749.

International Search Report and Written Opinion for application PCT/EP2021/071873, mailed Dec. 20, 2021.

International Search Report for PCT/EP2020/081513 mailed Nov. 9, 2020.

Koglin, Norman et al. "Novel modified and radiolabeled neuropeptide Y analogues to study Y-receptor subtypes" (2004) Neuropeptides, vol. 38, No. 4. 153-161.

Merkouris, et al. "Supplemental Appendix, Function-Based Selection of TrB Activating Antibodies: Characterization of a Full BDNK Agonist Antibody on Human Neurons", PNAS, Published Jul. 9, 2018, 10 pgs.

Merkouris, Spyros et al., "Fully Human agonist antibodies to TrkB using autocrine cell-based selection from a combinatorial antibody library", (2018) PNAS, vol. 115, No. 30, E7023-E7032.

Roux, Stephane et al. "Elimination and exchange of trifluroacetate counter-ion from cationic peptides: a crtical evaluation of different approaches" (2008), Journal Peptide Science, vol. 14, 354-359.

Wang, Shudan et al. "Therapeutic Potential of a TrkB agonistic antibody for Alzheimer's Disease" (2020) Thernostics, vol. 10, Issue 15, 6854-6874.

* cited by examiner

SEQUENCE LISTING

```
<160> NUMBER OF SEQ ID NOS: 212

<210> SEQ ID NO 1
<211> LENGTH: 36
<212> TYPE: PRT
<213> ORGANISM: Homo sapiens
<220> FEATURE:
<223> OTHER INFORMATION: hNPY
<220> FEATURE:
<223> OTHER INFORMATION: C-term amidation

<400> SEQUENCE: 1

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35


<210> SEQ ID NO 2
<211> LENGTH: 36
<212> TYPE: PRT
<213> ORGANISM: Homo sapiens
```

```
<220> FEATURE:
<223> OTHER INFORMATION: hPYY(1-36)
<220> FEATURE:
<223> OTHER INFORMATION: C-term amidation

<400> SEQUENCE: 2

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35


<210> SEQ ID NO 3
<211> LENGTH: 36
<212> TYPE: PRT
<213> ORGANISM: Homo sapiens
<220> FEATURE:
<223> OTHER INFORMATION: hPP
<220> FEATURE:
<223> OTHER INFORMATION: C-term amidation

<400> SEQUENCE: 3

Ala Pro Leu Glu Pro Val Tyr Pro Gly Asp Asn Ala Thr Pro Glu Gln
1               5                   10                  15

Met Ala Gln Tyr Ala Ala Asp Leu Arg Arg Tyr Ile Asn Met Leu Thr
            20                  25                  30

Arg Pro Arg Tyr
        35


<210> SEQ ID NO 4
<211> LENGTH: 34
<212> TYPE: PRT
<213> ORGANISM: Homo sapiens
<220> FEATURE:
<223> OTHER INFORMATION: hPYY(3-36)

<400> SEQUENCE: 4

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr


<210> SEQ ID NO 5
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments
```

<400> SEQUENCE: 5

Ala Pro Glu Lys Pro Glu Ala Asp Ala Glu Pro Glu Glu Leu Gln Arg
1               5                   10                  15

Tyr Tyr Ile Ala Leu Arg His Tyr Tyr Asn Trp Leu Thr Arg Gln Arg
            20                  25                  30

Tyr

<210> SEQ ID NO 6
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 6

Ala Pro Glu Lys Pro Glu Glu Asp Ala Ser Pro Glu Glu Leu Gln Arg
1               5                   10                  15

Tyr Tyr Ile Ala Leu Arg His Tyr Tyr Asn Trp Leu Thr Arg Gln Arg
            20                  25                  30

Tyr

<210> SEQ ID NO 7
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 7

Ala Pro Ala Lys Pro Glu Ala Asp Ala Glu Pro Glu Glu Leu Gln Arg
1               5                   10                  15

Tyr Tyr Val Ala Leu Arg His Tyr Tyr Asn Trp Leu Thr Arg Gln Arg
            20                  25                  30

Tyr

<210> SEQ ID NO 8
<211> LENGTH: 33
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
connected to (6- [(4S)-4-carboxy-4-(17-carboxyheptadecanamido)
butanamido] hexanoyl
<220> FEATURE:
<223> OTHER INFORMATION: C-term amidation
<220> FEATURE:
<223> OTHER INFORMATION: See specification as filed for detailed
description of substitutions and preferred embodiments

<400> SEQUENCE: 8

```
Ala Pro Glu Lys Pro Glu Glu Ala Ala Glu Pro Glu Glu Leu Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 9
<211> LENGTH: 33
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
connected to (6- [(4S)-4-carboxy-4-(17-carboxyheptadecanamido)
butanamido] hexanoyl
<220> FEATURE:
<223> OTHER INFORMATION: C-term amidation
<220> FEATURE:
<223> OTHER INFORMATION: See specification as filed for detailed
description of substitutions and preferred embodiments

<400> SEQUENCE: 9

```
Ala Pro Ala Lys Pro Glu Glu Asp Ala Ser Pro Glu Glu Leu Gln Arg
1               5                   10                  15

Gln Tyr Val Ser Leu Arg His Tyr Tyr Asn Trp Leu Thr Arg Gln Arg
            20                  25                  30

Tyr
```

<210> SEQ ID NO 10
<211> LENGTH: 33
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 10

```
Ala Pro Glu Lys Pro Glu Ala Asp Ala Glu Pro Glu Glu Leu Gln Arg
1               5                   10                  15

Tyr Tyr Val Ala Leu Arg His Tyr Tyr Asn Trp Leu Thr Arg Gln Arg
            20                  25                  30

Tyr
```

<210> SEQ ID NO 11
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 11

```
Ala Pro Glu Lys Pro Glu Ala Asp Ala Thr Pro Glu Glu Ile Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 12
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 12

Ala Pro Glu Lys Pro Glu Glu Asp Glu Thr Pro Glu Glu Leu Gln Arg
1 5 10 15

Tyr Tyr Val Ser Leu Arg His Tyr Tyr Asn Trp Leu Thr Arg Gln Arg
20 25 30

Tyr

<210> SEQ ID NO 13
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 13

Ala Pro Glu Lys Pro Glu Glu Gln Ala Thr Pro Glu Glu Leu Gln Arg
1 5 10 15

Tyr Tyr Val Ser Leu Arg His Tyr Tyr Asn Trp Leu Thr Arg Gln Arg
20 25 30

Tyr

<210> SEQ ID NO 14
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 14

Ala Pro Ala Lys Pro Glu Ala Ala Ala Glu Pro Glu Glu Leu Gln Arg
1 5 10 15

Tyr Tyr Val Ala Leu Arg His Tyr Tyr Asn Trp Leu Thr Arg Gln Arg
20 25 30

Tyr

<210> SEQ ID NO 15
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 15

```
Ala Pro Glu Lys Pro Glu Ala Asp Ala Ser Pro Glu Glu Ile Gln Arg
1               5                   10                  15

Tyr Tyr Ile Ser Leu Arg His Tyr Tyr Asn Trp Leu Thr Arg Gln Arg
            20                  25                  30

Tyr
```

<210> SEQ ID NO 16
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 16

```
Ala Pro Glu Lys Pro Glu Glu Asp Ala Ser Pro Glu Glu Leu Gln Gln
1               5                   10                  15

Tyr Tyr Val Ser Leu Arg His Tyr Tyr His Trp Leu Thr Arg Gln Arg
            20                  25                  30

Tyr
```

<210> SEQ ID NO 17
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:

<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 17

```
Ala Pro Glu Lys Pro Glu Ala Asp Ala Ser Pro Glu Glu Thr Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 18
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 18

```
Ala Pro Glu Lys Pro Pro Glu Asp Ala Ser Pro Glu Glu Leu Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 19
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 19

Ala Pro Glu Lys Pro Glu Glu Asp Ala Ser Pro Glu Glu Ile Gln Gln
1 5 10 15

Tyr Tyr Val Ser Leu Arg His Tyr Tyr Asn Trp Leu Thr Arg Gln Arg
20 25 30

Tyr

<210> SEQ ID NO 20
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 20

Ala Pro Glu Lys Pro Glu Glu Asp Ala Thr Pro Glu Glu Leu Gln Lys
1 5 10 15

Tyr Tyr Val Ser Leu Arg His Tyr Tyr Asn Trp Leu Thr Arg Gln Arg
20 25 30

Tyr

<210> SEQ ID NO 21
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 21

Ala Pro Glu Lys Pro Glu Glu Asp Ala Thr Pro Glu Glu Ile Gln Arg
1 5 10 15

Tyr Tyr Pro Ser Leu Arg His Tyr Tyr Asn Trp Leu Thr Arg Gln Arg
20 25 30

Tyr

<210> SEQ ID NO 22
<211> LENGTH: 33
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
connected to (6- [(4S)-4-carboxy-4-(17-carboxyheptadecanamido)
butanamido] hexanoyl
<220> FEATURE:
<223> OTHER INFORMATION: C-term amidation
<220> FEATURE:
<223> OTHER INFORMATION: See specification as filed for detailed
description of substitutions and preferred embodiments

<400> SEQUENCE: 22

```
Ala Pro Glu Lys Pro Glu Glu Asp Ala Ser Pro Glu Glu Leu Gln Arg
1               5                   10                  15

Tyr Tyr Val Ala Leu Arg His Tyr Tyr Asn Trp Leu Thr Arg Gln Arg
            20                  25                  30

Tyr
```

<210> SEQ ID NO 23
<211> LENGTH: 33
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
connected to (6- [(4S)-4-carboxy-4-(17-carboxyheptadecanamido)
butanamido] hexanoyl
<220> FEATURE:
<223> OTHER INFORMATION: C-term amidation
<220> FEATURE:
<223> OTHER INFORMATION: See specification as filed for detailed
description of substitutions and preferred embodiments

<400> SEQUENCE: 23

```
Ala Pro Glu Lys Pro Glu Glu Asp Ala Thr Glu Glu Glu Leu Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 24
<211> LENGTH: 33
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 24

```
Ala Pro Ala Lys Pro Glu Glu Asp Ala Ser Pro Glu Glu Leu Gln Arg
1               5                   10                  15

Tyr Gln Val Ser Leu Arg His Tyr Tyr Asn Trp Leu Thr Arg Gln Arg
            20                  25                  30

Tyr
```

<210> SEQ ID NO 25
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 25

```
Ala Pro Glu Lys Pro Glu Glu Asp Ala Glu Pro Glu Glu Leu Gln Arg
1               5                   10                  15

Tyr Tyr Val Ala Leu Arg His Tyr Tyr Asn Trp Leu Thr Arg Gln Arg
            20                  25                  30

Tyr
```

<210> SEQ ID NO 26
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:

```
<223> OTHER INFORMATION: See specification as filed for detailed
      description of substitutions and preferred embodiments

<400> SEQUENCE: 26

Ala Pro Glu Lys Pro Glu Glu Asp Pro Thr Pro Glu Glu Leu Gln Arg
1               5                   10                  15

Tyr Tyr Val Ser Leu Arg His Tyr Tyr Asn Trp Leu Thr Arg Gln Arg
            20                  25                  30

Tyr


<210> SEQ ID NO 27
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 27

Ala Pro Glu Lys Pro Glu Glu Glu Ala Ser Pro Glu Glu Leu Gln Arg
1               5                   10                  15

Tyr Tyr Val Ser Leu Arg His Tyr Tyr Asn Trp Leu Thr Arg Gln Arg
            20                  25                  30

Tyr


<210> SEQ ID NO 28
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 28

Ala Pro Glu Lys Pro Glu Glu Asp Ser Ser Pro Glu Glu Leu Gln Arg
1               5                   10                  15

Tyr Tyr Val Ala Leu Arg His Tyr Tyr Asn Trp Leu Thr Arg Gln Arg
            20                  25                  30
```

Tyr

<210> SEQ ID NO 29
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 29

```
Ala Pro Glu Lys Pro Glu Ala Asp Ala Thr Pro Glu Glu Leu Gln Arg
1               5                   10                  15

Tyr Tyr Ile Ser Leu Arg His Tyr Tyr Asn Trp Leu Thr Arg Gln Arg
            20                  25                  30

Tyr
```

<210> SEQ ID NO 30
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 30

```
Ala Pro Ala Lys Pro Glu Glu Asp Ala Thr Pro Glu Glu Leu Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 31
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:

<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 31

```
Ala Pro Glu Lys Pro Glu Glu Asp Ala Glu Pro Glu Glu Ser Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 32
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 32

```
Ala Pro Glu Lys Pro Pro Glu Asp Ala Thr Pro Glu Glu Ile Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 33
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation -continued

```
<220> FEATURE:
<223> OTHER INFORMATION: See specification as filed for detailed
      description of substitutions and preferred embodiments

<400> SEQUENCE: 33

Ala Pro Glu Lys Pro Glu Ala Asp Ser Ser Pro Glu Glu Leu Gln Arg
1               5                   10                  15

Tyr Tyr Val Ser Leu Arg His Tyr Tyr Asn Trp Leu Thr Arg Gln Arg
            20                  25                  30

Tyr


<210> SEQ ID NO 34
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 34

Ala Pro Glu Lys Pro Pro Ala Asp Ala Thr Pro Glu Glu Leu Gln Arg
1               5                   10                  15

Tyr Tyr Val Ser Leu Arg His Tyr Tyr Asn Trp Leu Thr Arg Gln Arg
            20                  25                  30

Tyr


<210> SEQ ID NO 35
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 35

Ala Pro Glu Lys Pro Glu Glu Asp Ala Thr Pro Glu Glu Leu Gln Pro
1               5                   10                  15

Tyr Tyr Val Ser Leu Arg His Tyr Tyr Asn Trp Leu Thr Arg Gln Arg
            20                  25                  30
```

Tyr

<210> SEQ ID NO 36
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 36

```
Ala Pro Ala Lys Pro Glu Glu Asp Ala Ser Pro Glu Glu Leu Gln Arg
1               5                   10                  15

Tyr Tyr Val Ser Leu Arg His Gln Tyr Asn Trp Leu Thr Arg Gln Arg
            20                  25                  30

Tyr
```

<210> SEQ ID NO 37
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 37

```
Ala Pro Ala Lys Pro Glu Glu Asp Ala Glu Pro Glu Glu Leu Gln Arg
1               5                   10                  15

Tyr Tyr Ile Ser Leu Arg His Tyr Tyr Asn Trp Leu Thr Arg Gln Arg
            20                  25                  30

Tyr
```

<210> SEQ ID NO 38
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 38

```
Ala Pro Glu Lys Pro Glu Glu Asp Ala Ser Ala Glu Glu Leu Gln Gln
1               5                   10                  15

Tyr Tyr Val Ser Leu Arg His Tyr Tyr Asn Trp Leu Thr Arg Gln Arg
            20                  25                  30

Tyr
```

<210> SEQ ID NO 39
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 39

```
Ala Pro Ala Lys Pro Glu Glu Ala Ala Thr Pro Glu Glu Leu Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 40
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:

<223> OTHER INFORMATION: C-term amidation
<220> FEATURE:
<223> OTHER INFORMATION: See specification as filed for detailed description of substitutions and preferred embodiments

<400> SEQUENCE: 40

Ala Pro Ala Lys Pro Glu Glu Ala Ala Thr Pro Glu Glu Ile Gln Arg
1 5 10 15

Tyr Tyr Val Ser Leu Arg His Tyr Tyr Asn Trp Leu Thr Arg Gln Arg
20 25 30

Tyr

<210> SEQ ID NO 41
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 41

Ala Pro Glu Lys Pro Glu Glu Asp Ala Glu Pro Glu Glu Leu Gln Arg
1 5 10 15

Tyr Tyr Thr Ser Leu Arg His Tyr Tyr Asn Trp Leu Thr Arg Gln Arg
20 25 30

Tyr

<210> SEQ ID NO 42
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 42

Ala Pro Glu Lys Pro Glu Glu Asp Ala Thr Pro Glu Glu Leu Gln Glu
1 5 10 15

Tyr Tyr Val Ser Leu Arg His Tyr Tyr Asn Trp Leu Thr Arg Gln Arg 20 25 30

Tyr

<210> SEQ ID NO 43
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 43

Ala Pro Glu Lys Pro Glu Glu Asp Ala Ser Pro Glu Ala Leu Gln Glu
1 5 10 15

Tyr Tyr Val Ser Leu Arg His Tyr Tyr Asn Trp Leu Thr Arg Gln Arg
20 25 30

Tyr

<210> SEQ ID NO 44
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 44

Ala Pro Glu Lys Pro Glu Ala Asp Ala Ser Pro Glu Glu Ile Gln Arg
1 5 10 15

Tyr Tyr Ile Ala Leu Arg His Tyr Tyr Asn Trp Leu Thr Arg Gln Arg
20 25 30

Tyr

<210> SEQ ID NO 45
<211> LENGTH: 33
<212> TYPE: PRT
<213> ORGANISM: Artificial Sequence
<220> FEATURE:
<223> OTHER INFORMATION: Description of Artificial Sequence: Synthetic

```
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 45

Ala Pro Glu Lys Pro Glu Glu Asp Ala Glu Pro Glu Glu Leu Gln Arg
1               5                   10                  15

Tyr Tyr Thr Ser Leu Arg His Tyr Tyr Gln Trp Leu Thr Arg Gln Arg
            20                  25                  30

Tyr


<210> SEQ ID NO 46
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 46

Ala Pro Glu Lys Pro Glu Glu Pro Ala Thr Pro Glu Glu Leu Gln Arg
1               5                   10                  15

Tyr Tyr Val Ser Leu Arg His Tyr Tyr Asn Trp Leu Thr Arg Gln Arg
            20                  25                  30

Tyr


<210> SEQ ID NO 47
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
```

<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 47

```
Ala Pro Ala Lys Pro Glu Ala Ala Ala Glu Pro Glu Glu Leu Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 48
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 48

```
Ala Pro Glu Lys Pro Glu Glu Asp Ala Thr Pro Glu Glu Leu Gln Arg
1               5                   10                  15

Tyr Tyr Val Gly Leu Arg His Tyr Tyr Asn Trp Leu Thr Arg Gln Arg
            20                  25                  30

Tyr
```

<210> SEQ ID NO 49
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 49

```
Ala Pro Glu Lys Pro Glu Glu Ile Ala Thr Pro Glu Glu Leu Gln Arg
1               5                   10                  15
```

-continued

Tyr Tyr Val Ser Leu Arg His Tyr Tyr Asn Trp Leu Thr Arg Gln Arg
20 25 30

Tyr

<210> SEQ ID NO 50
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 50

Ala Pro Glu Lys Pro Glu Glu Asp Ala Glu Pro Glu Glu Leu Gln Arg
1 5 10 15

Tyr Tyr Ala Ser Leu Arg His Tyr Tyr Asn Trp Leu Thr Arg Gln Arg
20 25 30

Tyr

<210> SEQ ID NO 51
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 51

Ala Pro Glu Lys Pro Pro Glu Asp Ala Ser Pro Glu Glu Ile Gln Arg
1 5 10 15

Tyr Tyr Val Ala Leu Arg His Tyr Tyr Asn Trp Leu Thr Arg Gln Arg
20 25 30

Tyr

<210> SEQ ID NO 52
<211> LENGTH: 33
<212> TYPE: PRT
<213> ORGANISM: Artificial Sequence
<220> FEATURE:

<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 52

Ala Pro Ala Lys Pro Glu Glu Ala Ala Thr Pro Glu Glu Leu Gln Arg
1               5                   10                  15

Tyr Tyr Ile Ser Leu Arg His Tyr Tyr Asn Trp Leu Thr Arg Gln Arg
            20                  25                  30

Tyr

<210> SEQ ID NO 53
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 53

Ala Pro Glu Lys Pro Glu Glu Asp Ala Thr Pro Glu Glu Leu Gln Arg
1               5                   10                  15

Tyr Tyr Val Leu Leu Arg His Tyr Tyr Asn Trp Leu Thr Arg Gln Arg
            20                  25                  30

Tyr

<210> SEQ ID NO 54
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)

```
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 54

Ala Pro Glu Lys Pro Glu Glu Asp Ala Thr Pro Glu Glu Ile Gln Arg
1               5                   10                  15

Tyr Tyr Val Ala Leu Arg His Tyr Tyr Asn Trp Leu Thr Arg Gln Arg
            20                  25                  30

Tyr


<210> SEQ ID NO 55
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 55

Ala Pro Glu Lys Pro Glu Glu Asp Ala Thr Pro Glu Glu Leu Gln Arg
1               5                   10                  15

Tyr Tyr Val Gln Leu Arg His Tyr Tyr Asn Trp Leu Thr Arg Gln Arg
            20                  25                  30

Tyr


<210> SEQ ID NO 56
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 56

Ala Pro Glu Lys Pro Glu Glu Asp Ala Ser Pro Glu Glu Ile Gln Arg
1               5                   10                  15
```

Tyr Tyr Val Glu Leu Arg His Tyr Tyr Asn Trp Leu Thr Arg Gln Arg
20 25 30

Tyr

<210> SEQ ID NO 57
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 57

Ala Pro Glu Lys Pro Glu Glu Asp Ala Glu Pro Glu Glu Val Gln Arg
1 5 10 15

Tyr Tyr Val Ser Leu Arg His Tyr Tyr Asn Trp Leu Thr Arg Gln Arg
20 25 30

Tyr

<210> SEQ ID NO 58
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 58

Ala Pro Glu Lys Pro Glu Glu Asp Ala Thr Pro Glu Glu Ala Gln Arg
1 5 10 15

Tyr Tyr Val Ser Leu Arg His Tyr Tyr Asn Trp Leu Thr Arg Gln Arg
20 25 30

Tyr

<210> SEQ ID NO 59
<211> LENGTH: 33
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
connected to (6- [(4S)-4-carboxy-4-(17-carboxyheptadecanamido)
butanamido] hexanoyl
<220> FEATURE:
<223> OTHER INFORMATION: C-term amidation
<220> FEATURE:
<223> OTHER INFORMATION: See specification as filed for detailed
description of substitutions and preferred embodiments

<400> SEQUENCE: 59

```
Ala Pro Glu Lys Pro Glu Glu Asp Ala Ser Glu Glu Glu Ile Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 60
<211> LENGTH: 33
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
connected to (6- [(4S)-4-carboxy-4-(17-carboxyheptadecanamido)
butanamido] hexanoyl
<220> FEATURE:
<223> OTHER INFORMATION: C-term amidation
<220> FEATURE:
<223> OTHER INFORMATION: See specification as filed for detailed
description of substitutions and preferred embodiments

<400> SEQUENCE: 60

```
Ala Pro Glu Lys Pro Glu Glu Asp Ala Thr Ala Glu Glu Leu Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 61
<211> LENGTH: 33
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 61

```
Ala Pro Ala Lys Pro Glu Glu Asp Ala Thr Pro Glu Glu Ala Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 62
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 62

```
Ala Pro Glu Lys Pro Glu Glu Asp Ala Thr Pro Glu Glu Val Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 63
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 63

```
Ala Pro Ala Lys Pro Glu Glu Asp Ala Ser Pro Glu Glu Leu Gln Arg
```

-continued

```
1               5                   10                  15

Tyr Tyr Val Gln Leu Arg His Tyr Tyr Asn Trp Leu Thr Arg Gln Arg
            20                  25                  30

Tyr


<210> SEQ ID NO 64
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 64

Ala Pro Glu Lys Pro Glu Glu Asp Ala Ser Pro Glu Glu Leu Gln Arg
1               5                   10                  15

Tyr Tyr Val Ser Leu Arg His Tyr Tyr Gln Trp Leu Thr Arg Gln Arg
            20                  25                  30

Tyr


<210> SEQ ID NO 65
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 65

Ala Pro Glu Lys Pro Pro Ala Asp Ala Ser Pro Glu Glu Ile Gln Arg
1               5                   10                  15

Tyr Tyr Val Ser Leu Arg His Tyr Tyr Asn Trp Leu Thr Arg Gln Arg
            20                  25                  30

Tyr


<210> SEQ ID NO 66
<211> LENGTH: 33
<212> TYPE: PRT
```

<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
connected to (6- [(4S)-4-carboxy-4-(17-carboxyheptadecanamido)
butanamido] hexanoyl
<220> FEATURE:
<223> OTHER INFORMATION: C-term amidation
<220> FEATURE:
<223> OTHER INFORMATION: See specification as filed for detailed
description of substitutions and preferred embodiments

<400> SEQUENCE: 66

Ala Pro Ala Lys Pro Pro Glu Asp Ala Ser Pro Glu Glu Leu Gln Arg
1 5 10 15

Tyr Tyr Val Glu Leu Arg His Tyr Tyr Asn Trp Leu Thr Arg Gln Arg
20 25 30

Tyr

<210> SEQ ID NO 67
<211> LENGTH: 33
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
connected to (6- [(4S)-4-carboxy-4-(17-carboxyheptadecanamido)
butanamido] hexanoyl
<220> FEATURE:
<223> OTHER INFORMATION: C-term amidation
<220> FEATURE:
<223> OTHER INFORMATION: See specification as filed for detailed
description of substitutions and preferred embodiments

<400> SEQUENCE: 67

Ala Pro Ala Lys Pro Glu Glu Asp Ala Ser Pro Glu Glu Ile Gln Arg
1 5 10 15

Tyr Tyr Val Ser Leu Arg His Tyr Tyr Asn Trp Leu Thr Arg Gln Arg
20 25 30

Tyr

<210> SEQ ID NO 68
<211> LENGTH: 33
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)

<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 68

```
Ala Pro Glu Lys Pro Pro Glu Asp Ala Thr Pro Glu Glu Ile Gln Arg
1               5                   10                  15

Tyr Tyr Val Ala Leu Arg His Tyr Tyr Asn Trp Leu Thr Arg Gln Arg
            20                  25                  30

Tyr
```

<210> SEQ ID NO 69
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 69

```
Ala Pro Ala Lys Pro Glu Glu Asp Ala Ser Pro Glu Glu Ile Gln Arg
1               5                   10                  15

Tyr Tyr Ile Ala Leu Arg His Tyr Tyr Asn Trp Leu Thr Arg Gln Arg
            20                  25                  30

Tyr
```

<210> SEQ ID NO 70
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 70

Ala Pro Glu Lys Pro Glu Glu Asp Ala Thr Pro Glu Glu Leu Gln Arg
1 5 10 15

Tyr Tyr Ile Ser Leu Arg His Tyr Tyr Asn Trp Leu Thr Arg Gln Arg
20 25 30

Tyr

<210> SEQ ID NO 71
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 71

Ala Pro Glu Lys Pro Glu Glu Asp Ala Ser Pro Glu Glu Thr Gln Arg
1 5 10 15

Tyr Tyr Val Ala Leu Arg His Tyr Tyr Asn Trp Leu Thr Arg Gln Arg
20 25 30

Tyr

<210> SEQ ID NO 72
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 72

Ala Pro Glu Lys Pro Glu Glu Asp Ala Glu Pro Glu Glu Leu Gln Arg
1 5 10 15

Tyr Tyr Val Ser Leu Arg His Tyr Tyr Gln Trp Leu Thr Arg Gln Arg
20 25 30

Tyr

<210> SEQ ID NO 73
<211> LENGTH: 33

<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 73

```
Ala Pro Glu Lys Pro Pro Ala Asp Ala Ser Pro Glu Glu Thr Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 74
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 74

```
Ala Pro Ala Lys Pro Glu Glu Asp Ala Thr Pro Glu Glu Leu Gln Arg
1               5                   10                  15

Tyr Tyr Ile Ala Leu Arg His Tyr Tyr Asn Trp Leu Thr Arg Gln Arg
            20                  25                  30

Tyr
```

<210> SEQ ID NO 75
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES -continued
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 75

```
Ala Pro Ala Lys Pro Glu Glu Asp Ala Glu Pro Glu Glu Leu Gln Arg
1               5                   10                  15

Tyr Tyr Val Ala Leu Arg His Tyr Tyr Asn Trp Leu Thr Arg Gln Arg
            20                  25                  30

Tyr
```

<210> SEQ ID NO 76
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 76

```
Ala Pro Glu Lys Pro Glu Ala Asp Ala Glu Pro Glu Glu Leu Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 77
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 77

```
Ala Pro Glu Lys Pro Glu Glu Ala Ala Ser Pro Glu Glu Leu Gln Arg
1               5                   10                  15

Tyr Tyr Val Ala Leu Arg His Tyr Tyr Asn Trp Leu Thr Arg Gln Arg
            20                  25                  30

Tyr


<210> SEQ ID NO 78
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 78

Ala Pro Glu Lys Pro Glu Glu Asp Ala Thr Pro Glu Glu Leu Gln Arg
1               5                   10                  15

Tyr Tyr Val Ala Leu Arg His Tyr Tyr Asn Trp Leu Thr Arg Gln Arg
            20                  25                  30

Tyr


<210> SEQ ID NO 79
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 79

Ala Pro Glu Lys Pro Glu Glu Asp Ala Pro Pro Glu Glu Ile Gln Arg
1               5                   10                  15

Tyr Tyr Val Ser Leu Arg His Tyr Tyr Asn Trp Leu Thr Arg Gln Arg
            20                  25                  30

Tyr


<210> SEQ ID NO 80
```

<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 80

```
Ala Pro Glu Lys Pro Glu Glu Asp Ala Ser Pro Glu Glu Leu Gln Arg
1               5                   10                  15

Tyr Tyr Ile Ser Leu Arg His Tyr Tyr Asn Trp Leu Thr Arg Gln Arg
            20                  25                  30

Tyr
```

<210> SEQ ID NO 81
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 81

```
Ala Pro Ala Lys Pro Glu Glu Asp Ala Ser Pro Glu Glu Leu Gln Arg
1               5                   10                  15

Tyr Tyr Val Ser Leu Arg His Tyr Gln Asn Trp Leu Thr Arg Gln Arg
            20                  25                  30

Tyr
```

<210> SEQ ID NO 82
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:

```
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 82

Ala Pro Ala Lys Pro Glu Glu Asp Ala Ser Pro Glu Glu Leu Gln Arg
1               5                   10                  15

Tyr Tyr Val Ser Leu Arg His Tyr Tyr Gln Trp Leu Thr Arg Gln Arg
            20                  25                  30

Tyr


<210> SEQ ID NO 83
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 83

Ala Pro Glu Lys Pro Glu Glu Asp Ala Ser Pro Glu Glu Leu Gln Arg
1               5                   10                  15

Tyr Tyr Val Ser Leu Arg His Tyr Tyr Asn Trp Leu Thr Arg Gln Arg
            20                  25                  30

Tyr


<210> SEQ ID NO 84
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments
```

<400> SEQUENCE: 84

Ala Pro Glu Lys Pro Glu Glu Asp Ala Ser Glu Ala Glu Leu Gln Arg
1 5 10 15

Tyr Tyr Val Ser Leu Arg His Tyr Tyr Asn Trp Leu Thr Arg Gln Arg
20 25 30

Tyr

<210> SEQ ID NO 85
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 85

Ala Pro Glu Lys Pro Glu Glu Asp Ala Gln Pro Glu Glu Ile Gln Arg
1 5 10 15

Tyr Tyr Val Ser Leu Arg His Tyr Tyr Asn Trp Leu Thr Arg Gln Arg
20 25 30

Tyr

<210> SEQ ID NO 86
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 86

Ala Pro Ala Lys Pro Pro Glu Asp Ala Ser Pro Glu Glu Ile Gln Arg
1 5 10 15

Tyr Tyr Val Ser Leu Arg His Tyr Tyr Asn Trp Leu Thr Arg Gln Arg
20 25 30

Tyr

<210> SEQ ID NO 87
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 87

```
Ala Pro Glu Lys Pro Glu Glu Asp Ala Thr Ser Glu Glu Leu Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 88
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 88

```
Ala Pro Glu Lys Pro Glu Glu Asp Ala Thr Pro Glu Glu Ile Gln Arg
1               5                   10                  15

Tyr Tyr Val Ala Leu Arg His Tyr Tyr Asn Trp Leu Thr Arg Gln Arg
            20                  25                  30

Tyr
```

<210> SEQ ID NO 89
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl -continued
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 89

```
Ala Pro Ala Lys Pro Glu Glu Asp Ala Ser Pro Glu Glu Thr Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 90
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 90

```
Ala Pro Glu Lys Pro Glu Glu Asp Ala Thr Pro Glu Glu Ile Gln Arg
1               5                   10                  15

Tyr Tyr Ala Ser Leu Arg His Tyr Tyr Asn Trp Leu Thr Arg Gln Arg
            20                  25                  30

Tyr
```

<210> SEQ ID NO 91
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 91

Ala Pro Glu Lys Pro Glu Glu Asp Ala Thr Pro Glu Glu Leu Gln Arg
1 5 10 15

Tyr Tyr Val Pro Leu Arg His Tyr Tyr Asn Trp Leu Thr Arg Gln Arg
20 25 30

Tyr

<210> SEQ ID NO 92
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 92

Ala Pro Glu Lys Pro Glu Glu Asp Ala Thr Pro Glu Glu Leu Gln Arg
1 5 10 15

Gln Tyr Val Ser Leu Arg His Tyr Tyr Asn Trp Leu Thr Arg Gln Arg
20 25 30

Tyr

<210> SEQ ID NO 93
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 93

Ala Pro Ala Lys Pro Pro Glu Asp Ala Ser Pro Glu Glu Leu Gln Arg
1 5 10 15

Tyr Tyr Val Ala Leu Arg His Tyr Tyr Asn Trp Leu Thr Arg Gln Arg
20 25 30

Tyr

<210> SEQ ID NO 94
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 94

```
Ala Pro Glu Lys Pro Glu Glu Asp Ala Thr Pro Glu Glu Leu Gln Arg
1               5                   10                  15

Tyr Tyr Val Val Leu Arg His Tyr Tyr Asn Trp Leu Thr Arg Gln Arg
            20                  25                  30

Tyr
```

<210> SEQ ID NO 95
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 95

```
Ala Pro Glu Lys Pro Glu Glu Asp Ala Glu Pro Glu Glu Leu Gln Arg
1               5                   10                  15

Tyr Tyr Thr Ser Leu Arg His Tyr Tyr His Trp Leu Thr Arg Gln Arg
            20                  25                  30

Tyr
```

<210> SEQ ID NO 96
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:

-continued

<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 96

```
Ala Pro Glu Lys Pro Gly Glu Asp Ala Ser Pro Glu Glu Leu Gln Arg
1               5                   10                  15

Tyr Tyr Ile Ser Leu Arg His Tyr Tyr Asn Trp Leu Thr Arg Gln Arg
            20                  25                  30

Tyr
```

<210> SEQ ID NO 97
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 97

```
Ala Pro Glu Lys Pro Glu Glu Asp Ala Ser Pro Glu Glu Ile Gln Arg
1               5                   10                  15

Tyr Tyr Val Gln Leu Arg His Tyr Tyr Asn Trp Leu Thr Arg Gln Arg
            20                  25                  30

Tyr
```

<210> SEQ ID NO 98
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 98

```
Ala Pro Ala Lys Pro Glu Ala Asp Ala Ser Pro Glu Glu Leu Gln Arg
1               5                   10                  15

Tyr Tyr Val Glu Leu Arg His Tyr Tyr Asn Trp Leu Thr Arg Gln Arg
            20                  25                  30

Tyr
```

<210> SEQ ID NO 99
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 99

```
Ala Pro Glu Lys Pro Glu Glu Asp Ala Thr Pro Glu Glu Leu Gln Ala
1               5                   10                  15

Tyr Tyr Val Ser Leu Arg His Tyr Tyr Asn Trp Leu Thr Arg Gln Arg
            20                  25                  30

Tyr
```

<210> SEQ ID NO 100
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 100

```
Ala Pro Glu Lys Pro Glu Glu Ser Ala Thr Pro Glu Glu Leu Gln Arg
1               5                   10                  15

Tyr Tyr Val Ser Leu Arg His Tyr Tyr Asn Trp Leu Thr Arg Gln Arg
            20                  25                  30

Tyr
```

```
<210> SEQ ID NO 101
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 101

Ala Pro Glu Lys Pro Glu Glu Asp Ala Thr Pro Glu Glu Ile Gln Arg
1               5                   10                  15

Tyr Tyr Leu Ser Leu Arg His Tyr Tyr Asn Trp Leu Thr Arg Gln Arg
            20                  25                  30

Tyr


<210> SEQ ID NO 102
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 102

Ala Pro Glu Lys Pro Glu Ala Asp Ala Thr Pro Glu Glu Ile Gln Arg
1               5                   10                  15

Tyr Tyr Val Ser Leu Arg His Tyr Tyr Asn Trp Leu Thr Arg Gln Arg
            20                  25                  30

Tyr


<210> SEQ ID NO 103
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
```

<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 103

```
Ala Pro Ala Lys Pro Glu Glu Asp Ala Thr Pro Glu Glu Ile Gln Arg
1               5                   10                  15

Tyr Tyr Val Ala Leu Arg His Tyr Tyr Asn Trp Leu Thr Arg Gln Arg
            20                  25                  30

Tyr
```

<210> SEQ ID NO 104
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 104

```
Ala Pro Glu Lys Pro Glu Ala Asp Ala Thr Pro Glu Glu Leu Gln Arg
1               5                   10                  15

Tyr Tyr Ile Ala Leu Arg His Tyr Tyr Asn Trp Leu Thr Arg Gln Arg
            20                  25                  30

Tyr
```

<210> SEQ ID NO 105
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:

<223> OTHER INFORMATION: See specification as filed for detailed description of substitutions and preferred embodiments

<400> SEQUENCE: 105

Ala Pro Ala Lys Pro Glu Glu Asp Ala Thr Pro Glu Glu Leu Gln Arg
1               5                   10                  15

Tyr Tyr Val Ala Leu Arg His Tyr Tyr Asn Trp Leu Thr Arg Gln Arg
            20                  25                  30

Tyr

<210> SEQ ID NO 106
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 106

Ala Pro Glu Lys Pro Glu Glu Asp Ala Thr Leu Glu Glu Leu Gln Arg
1               5                   10                  15

Tyr Tyr Val Ser Leu Arg His Tyr Tyr Asn Trp Leu Thr Arg Gln Arg
            20                  25                  30

Tyr

<210> SEQ ID NO 107
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 107

Ala Pro Glu Lys Pro Glu Glu Asp Ala Ser Ala Glu Glu Leu Gln Arg
1               5                   10                  15

Tyr Tyr Val Ala Leu Arg His Tyr Tyr Asn Trp Leu Thr Arg Gln Arg
            20                  25                  30

Tyr

<210> SEQ ID NO 108
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 108

Ala Pro Glu Lys Pro Glu Glu Asp Ala Glu Pro Glu Glu Ala Gln Arg
1 5 10 15

Tyr Tyr Val Ser Leu Arg His Tyr Tyr Asn Trp Leu Thr Arg Gln Arg
20 25 30

Tyr

<210> SEQ ID NO 109
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 109

Ala Pro Glu Lys Pro Glu Glu Asp Ala Thr Gln Glu Glu Leu Gln Arg
1 5 10 15

Tyr Tyr Val Ser Leu Arg His Tyr Tyr Asn Trp Leu Thr Arg Gln Arg
20 25 30

Tyr

<210> SEQ ID NO 110
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:

<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 110

```
Ala Pro Ala Lys Pro Glu Glu Asp Ala Ser Pro Glu Glu Leu Gln Arg
1               5                   10                  15

Tyr Tyr Val Ala Leu Arg His Tyr Tyr Asn Trp Leu Thr Arg Gln Arg
            20                  25                  30

Tyr
```

<210> SEQ ID NO 111
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 111

```
Ala Pro Glu Lys Pro Glu Glu Asp Ala Glu Pro Glu Glu Thr Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 112
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 112

Ala Pro Glu Lys Pro Glu Ala Asp Ala Ser Glu Glu Glu Leu Gln Arg
1 5 10 15

Tyr Tyr Val Ser Leu Arg His Tyr Tyr Asn Trp Leu Thr Arg Gln Arg
20 25 30

Tyr

<210> SEQ ID NO 113
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 113

Ala Pro Glu Lys Pro Glu Glu Asp Leu Thr Pro Glu Glu Leu Gln Arg
1 5 10 15

Tyr Tyr Val Ser Leu Arg His Tyr Tyr Asn Trp Leu Thr Arg Gln Arg
20 25 30

Tyr

<210> SEQ ID NO 114
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 114

Ala Pro Glu Lys Pro Glu Glu Asp Ala Thr Pro Glu Glu Leu Gln Arg
1 5 10 15

Tyr Tyr Val Glu Leu Arg His Tyr Tyr Asn Trp Leu Thr Arg Gln Arg
20 25 30

Tyr

<210> SEQ ID NO 115
<211> LENGTH: 33
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
connected to (6- [(4S)-4-carboxy-4-(17-carboxyheptadecanamido)
butanamido] hexanoyl
<220> FEATURE:
<223> OTHER INFORMATION: C-term amidation
<220> FEATURE:
<223> OTHER INFORMATION: See specification as filed for detailed
description of substitutions and preferred embodiments

<400> SEQUENCE: 115

```
Ala Pro Ala Lys Pro Glu Ala Ala Ala Glu Pro Glu Glu Ile Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 116
<211> LENGTH: 33
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
connected to (6- [(4S)-4-carboxy-4-(17-carboxyheptadecanamido)
butanamido] hexanoyl
<220> FEATURE:
<223> OTHER INFORMATION: C-term amidation
<220> FEATURE:
<223> OTHER INFORMATION: See specification as filed for detailed
description of substitutions and preferred embodiments

<400> SEQUENCE: 116

```
Ala Pro Glu Lys Pro Glu Glu Asp Ala Glu Pro Glu Glu Ile Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 117
<211> LENGTH: 33
<212> TYPE: PRT
<213> ORGANISM: Artificial Sequence
<220> FEATURE:
<223> OTHER INFORMATION: Description of Artificial Sequence: Synthetic
polypeptide <220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 117

```
Ala Pro Glu Lys Pro Glu Glu Asp Ala Thr Pro Glu Glu Ile Gln Arg
1               5                   10                  15

Tyr Tyr Val Ser Leu Arg His Tyr Gln Asn Trp Leu Thr Arg Gln Arg
            20                  25                  30

Tyr
```

<210> SEQ ID NO 118
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 118

```
Ala Pro Ala Lys Pro Glu Glu Asp Ala Thr Pro Glu Glu Ile Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 119
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:

<223> OTHER INFORMATION: C-term amidation
<220> FEATURE:
<223> OTHER INFORMATION: See specification as filed for detailed description of substitutions and preferred embodiments

<400> SEQUENCE: 119

Ala Pro Glu Lys Pro Glu Glu Asp Ala Thr Pro Glu Glu Leu Gln Arg
1 5 10 15

Tyr Gln Val Ser Leu Arg His Tyr Tyr Asn Trp Leu Thr Arg Gln Arg
20 25 30

Tyr

<210> SEQ ID NO 120
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 120

Ala Pro Ala Lys Pro Glu Ala Ala Ala Glu Pro Glu Glu Ile Gln Arg
1 5 10 15

Tyr Tyr Val Ala Leu Arg His Tyr Tyr Asn Trp Leu Thr Arg Gln Arg
20 25 30

Tyr

<210> SEQ ID NO 121
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 121

Ala Pro Glu Lys Pro Glu Glu Asp Ala Ser Pro Glu Glu Ala Gln Arg
1 5 10 15

Tyr Tyr Val Ala Leu Arg His Tyr Tyr Asn Trp Leu Thr Arg Gln Arg 20 25 30

Tyr

<210> SEQ ID NO 122
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 122

Ala Pro Glu Lys Pro Pro Glu Asp Ala Glu Pro Glu Glu Ile Gln Arg
1 5 10 15

Tyr Tyr Val Ser Leu Arg His Tyr Tyr Asn Trp Leu Thr Arg Gln Arg
20 25 30

Tyr

<210> SEQ ID NO 123
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 123

Ala Pro Glu Lys Pro Glu Glu Asp Ala Thr Pro Glu Glu Ser Gln Arg
1 5 10 15

Tyr Tyr Val Ser Leu Arg His Tyr Tyr Asn Trp Leu Thr Arg Gln Arg
20 25 30

Tyr

<210> SEQ ID NO 124
<211> LENGTH: 33
<212> TYPE: PRT
<213> ORGANISM: Artificial Sequence
<220> FEATURE:
<223> OTHER INFORMATION: Description of Artificial Sequence: Synthetic

```
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 124

Ala Pro Ala Lys Pro Glu Glu Ala Ala Thr Pro Glu Glu Ile Gln Arg
1               5                   10                  15

Tyr Tyr Val Ala Leu Arg His Tyr Tyr Asn Trp Leu Thr Arg Gln Arg
            20                  25                  30

Tyr


<210> SEQ ID NO 125
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 125

Ala Pro Glu Lys Pro Glu Ala Asp Ala Ser Pro Glu Glu Leu Gln Arg
1               5                   10                  15

Tyr Tyr Val Gln Leu Arg His Tyr Tyr Asn Trp Leu Thr Arg Gln Arg
            20                  25                  30

Tyr


<210> SEQ ID NO 126
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
```

<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 126

```
Ala Pro Glu Lys Pro Glu Ala Glu Ala Ser Pro Glu Glu Leu Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 127
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 127

```
Ala Pro Glu Lys Pro Glu Glu Asp Ala Ala Pro Glu Glu Leu Gln Lys
1               5                   10                  15

Tyr Tyr Val Ser Leu Arg His Tyr Tyr Asn Trp Leu Thr Arg Gln Arg
            20                  25                  30

Tyr
```

<210> SEQ ID NO 128
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 128

```
Ala Pro Glu Lys Pro Glu Ala Ala Ala Glu Pro Glu Glu Ile Gln Arg
1               5                   10                  15
```

Tyr Tyr Val Ser Leu Arg His Tyr Tyr Asn Trp Leu Thr Arg Gln Arg
20 25 30

Tyr

<210> SEQ ID NO 129
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 129

Ala Pro Glu Lys Pro Glu Glu Asp Ala Ser Pro Glu Glu Leu Gln Arg
1 5 10 15

Tyr Tyr Val Glu Leu Arg His Tyr Tyr Asn Trp Leu Thr Arg Gln Arg
20 25 30

Tyr

<210> SEQ ID NO 130
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 130

Ala Pro Glu Lys Pro Glu Glu Asp Ala Glu Pro Glu Glu Leu Gln Arg
1 5 10 15

Tyr Tyr Val Ser Leu Arg His Tyr Tyr Asn Trp Leu Thr Arg Gln Arg
20 25 30

Tyr

<210> SEQ ID NO 131
<211> LENGTH: 33
<212> TYPE: PRT
<213> ORGANISM: Artificial Sequence
<220> FEATURE:

```
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 131

Ala Pro Glu Lys Pro Glu Ala Ala Ala Glu Pro Glu Glu Leu Gln Arg
1               5                   10                  15

Tyr Tyr Val Ala Leu Arg His Tyr Tyr Asn Trp Leu Thr Arg Gln Arg
            20                  25                  30

Tyr


<210> SEQ ID NO 132
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 132

Ala Pro Glu Lys Pro Glu Glu Ala Ala Thr Pro Glu Glu Leu Gln Arg
1               5                   10                  15

Tyr Tyr Val Ser Leu Arg His Tyr Tyr Asn Trp Leu Thr Arg Gln Arg
            20                  25                  30

Tyr


<210> SEQ ID NO 133
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
```

```
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 133

Ala Pro Glu Lys Pro Glu Glu Asp Ala Ser Ala Glu Glu Ile Gln Arg
1               5                   10                  15

Tyr Tyr Val Ser Leu Arg His Tyr Tyr Asn Trp Leu Thr Arg Gln Arg
            20                  25                  30

Tyr


<210> SEQ ID NO 134
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 134

Ala Pro Glu Lys Pro Glu Glu Asp Ala Thr Pro Glu Glu Leu Gln Leu
1               5                   10                  15

Tyr Tyr Val Ser Leu Arg His Tyr Tyr Asn Trp Leu Thr Arg Gln Arg
            20                  25                  30

Tyr


<210> SEQ ID NO 135
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 135

Ala Pro Glu Lys Pro Glu Ala Asp Ala Glu Pro Glu Glu Ile Gln Arg
1               5                   10                  15
```

Tyr Tyr Val Ala Leu Arg His Tyr Tyr Asn Trp Leu Thr Arg Gln Arg
20 25 30

Tyr

<210> SEQ ID NO 136
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 136

Ala Pro Glu Lys Pro Glu Ala Asp Ala Thr Pro Glu Glu Leu Gln Arg
1 5 10 15

Tyr Tyr Val Ser Leu Arg His Tyr Tyr Asn Trp Leu Thr Arg Gln Arg
20 25 30

Tyr

<210> SEQ ID NO 137
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 137

Ala Pro Ala Lys Pro Glu Glu Asp Ala Glu Pro Glu Glu Leu Gln Arg
1 5 10 15

Tyr Tyr Val Ser Leu Arg His Tyr Tyr Asn Trp Leu Thr Arg Gln Arg
20 25 30

Tyr

<210> SEQ ID NO 138
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 138

Ala Pro Glu Lys Pro Glu Glu Asp Ala Thr Pro Glu Glu Gln Gln Arg
1               5                   10                  15

Tyr Tyr Val Ser Leu Arg His Tyr Tyr Asn Trp Leu Thr Arg Gln Arg
            20                  25                  30

Tyr

<210> SEQ ID NO 139
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 139

Ala Pro Glu Lys Pro Glu Ala Ala Ala Glu Pro Glu Glu Ile Gln Arg
1               5                   10                  15

Tyr Tyr Val Ala Leu Arg His Tyr Tyr Asn Trp Leu Thr Arg Gln Arg
            20                  25                  30

Tyr

<210> SEQ ID NO 140
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is

```
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 140

Ala Pro Glu Lys Pro Glu Ala Asp Ala Thr Pro Glu Glu Leu Gln Arg
1               5                   10                  15

Tyr Tyr Val Ala Leu Arg His Tyr Tyr Asn Trp Leu Thr Arg Gln Arg
            20                  25                  30

Tyr


<210> SEQ ID NO 141
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 141

Ala Pro Glu Lys Pro Glu Glu Asp Ala Thr Pro Glu Glu Leu Gln Arg
1               5                   10                  15

Tyr Tyr Val Ser Leu Arg His Tyr Tyr Asn Trp Leu Leu Arg Gln Arg
            20                  25                  30

Tyr


<210> SEQ ID NO 142
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 142

Ala Pro Glu Lys Pro Glu Glu Asp Ala Glu Pro Glu Glu Leu Gln Glu
```

-continued

```
1               5                   10                  15

Tyr Tyr Val Ser Leu Arg His Tyr Tyr Asn Trp Leu Thr Arg Gln Arg
            20                  25                  30

Tyr


<210> SEQ ID NO 143
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 143

Ala Pro Glu Lys Pro Glu Glu Glu Ala Ser Pro Ala Glu Leu Gln Arg
1               5                   10                  15

Tyr Tyr Val Ser Leu Arg His Tyr Tyr Asn Trp Leu Thr Arg Gln Arg
            20                  25                  30

Tyr


<210> SEQ ID NO 144
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 144

Ala Pro Glu Lys Pro Glu Ala Asp Ala Ser Pro Glu Glu Ile Gln Arg
1               5                   10                  15

Tyr Tyr Val Ser Leu Arg His Tyr Tyr Asn Trp Leu Thr Arg Gln Arg
            20                  25                  30

Tyr


<210> SEQ ID NO 145
<211> LENGTH: 33
<212> TYPE: PRT
```

<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 145

Ala Pro Glu Lys Pro Glu Glu Asp Ala Thr Pro Glu Glu Leu Gln Ser
1 5 10 15

Tyr Tyr Val Ser Leu Arg His Tyr Tyr Asn Trp Leu Thr Arg Gln Arg
20 25 30

Tyr

<210> SEQ ID NO 146
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 146

Ala Pro Glu Lys Pro Glu Glu Asp Ala Leu Pro Glu Glu Ile Gln Arg
1 5 10 15

Tyr Tyr Val Ser Leu Arg His Tyr Tyr Asn Trp Leu Thr Arg Gln Arg
20 25 30

Tyr

<210> SEQ ID NO 147
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)

<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 147

```
Ala Pro Glu Lys Pro Glu Glu Asp Ser Thr Pro Glu Glu Leu Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 148
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 148

```
Ala Pro Glu Lys Pro Glu Glu Asp Gln Thr Pro Glu Glu Leu Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 149
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 149

Ala Pro Ala Lys Pro Glu Glu Asp Ala Ser Pro Glu Glu Leu Gln Arg
1 5 10 15

Tyr Tyr Val Ser Leu Arg His Tyr Tyr Asn Trp Leu Thr Arg Gln Arg
20 25 30

Tyr

<210> SEQ ID NO 150
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 150

Ala Pro Glu Lys Pro Glu Glu Glu Ala Thr Pro Glu Glu Leu Gln Arg
1 5 10 15

Tyr Tyr Val Ser Leu Arg His Tyr Tyr Asn Trp Leu Thr Arg Gln Arg
20 25 30

Tyr

<210> SEQ ID NO 151
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 151

Ala Pro Glu Lys Pro Glu Glu Asp Ala Ser Pro Glu Glu Ile Gln Arg
1 5 10 15

Tyr Tyr Val Ser Leu Arg His Tyr Tyr Asn Trp Leu Thr Arg Gln Arg
20 25 30

Tyr

<210> SEQ ID NO 152
<211> LENGTH: 33

<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
connected to (6- [(4S)-4-carboxy-4-(17-carboxyheptadecanamido)
butanamido] hexanoyl
<220> FEATURE:
<223> OTHER INFORMATION: C-term amidation
<220> FEATURE:
<223> OTHER INFORMATION: See specification as filed for detailed
description of substitutions and preferred embodiments

<400> SEQUENCE: 152

```
Ala Pro Glu Lys Pro Glu Glu Asp Ala Thr Pro Glu Glu Leu Gln Arg
1               5                   10                  15

Tyr Tyr Val Thr Leu Arg His Tyr Tyr Asn Trp Leu Thr Arg Gln Arg
            20                  25                  30

Tyr
```

<210> SEQ ID NO 153
<211> LENGTH: 33
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
connected to (6- [(4S)-4-carboxy-4-(17-carboxyheptadecanamido)
butanamido] hexanoyl
<220> FEATURE:
<223> OTHER INFORMATION: C-term amidation
<220> FEATURE:
<223> OTHER INFORMATION: See specification as filed for detailed
description of substitutions and preferred embodiments

<400> SEQUENCE: 153

```
Ala Pro Ala Lys Pro Glu Glu Asp Ala Ser Pro Glu Glu Ser Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 154
<211> LENGTH: 33
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES

```
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 154

Ala Pro Glu Lys Pro Glu Glu Ala Ala Ser Pro Glu Glu Ile Gln Arg
1               5                   10                  15

Tyr Tyr Val Ser Leu Arg His Tyr Tyr Asn Trp Leu Thr Arg Gln Arg
            20                  25                  30

Tyr


<210> SEQ ID NO 155
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 155

Ala Pro Glu Lys Pro Glu Glu Asp Ser Ser Pro Glu Glu Leu Gln Arg
1               5                   10                  15

Tyr Tyr Val Ala Leu Arg His Tyr Tyr Asn Trp Leu Thr Arg Gln Arg
            20                  25                  30

Tyr


<210> SEQ ID NO 156
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 156
```

-continued

Ala Pro Glu Lys Pro Glu Glu Asp Ala Thr Pro Glu Glu Thr Gln Arg
1 5 10 15

Tyr Tyr Val Ser Leu Arg His Tyr Tyr Asn Trp Leu Thr Arg Gln Arg
20 25 30

Tyr

<210> SEQ ID NO 157
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 157

Ala Pro Glu Lys Pro Glu Glu Leu Ala Thr Pro Glu Glu Leu Gln Arg
1 5 10 15

Tyr Tyr Val Ser Leu Arg His Tyr Tyr Asn Trp Leu Thr Arg Gln Arg
20 25 30

Tyr

<210> SEQ ID NO 158
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 158

Ala Pro Glu Lys Pro Glu Glu Ala Ala Thr Pro Glu Glu Ile Gln Arg
1 5 10 15

Tyr Tyr Val Ala Leu Arg His Tyr Tyr Asn Trp Leu Thr Arg Gln Arg
20 25 30

Tyr

<210> SEQ ID NO 159

<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 159

Ala Pro Glu Lys Pro Glu Glu Asp Ala Thr Pro Glu Glu Leu Gln Arg
1               5                   10                  15

Tyr Tyr Val Ser Leu Arg His Tyr Tyr Asn Trp Leu Ser Arg Gln Arg
            20                  25                  30

Tyr

<210> SEQ ID NO 160
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 160

Ala Pro Glu Lys Pro Glu Glu Ala Ala Glu Pro Glu Glu Ile Gln Arg
1               5                   10                  15

Tyr Tyr Val Ala Leu Arg His Tyr Tyr Asn Trp Leu Thr Arg Gln Arg
            20                  25                  30

Tyr

<210> SEQ ID NO 161
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:

<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 161

```
Ala Pro Ala Lys Pro Glu Glu Ala Ala Ser Pro Glu Glu Leu Gln Arg
1               5                   10                  15

Tyr Tyr Val Ala Leu Arg His Tyr Tyr Asn Trp Leu Thr Arg Gln Arg
            20                  25                  30

Tyr
```

<210> SEQ ID NO 162
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 162

```
Ala Pro Glu Lys Pro Pro Glu Ala Ala Ser Pro Glu Glu Ile Gln Arg
1               5                   10                  15

Tyr Tyr Val Ala Leu Arg His Tyr Tyr Asn Trp Leu Thr Arg Gln Arg
            20                  25                  30

Tyr
```

<210> SEQ ID NO 163
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 163

Ala Pro Glu Lys Pro Glu Ala Asp Ala Glu Pro Glu Glu Leu Gln Arg
1 5 10 15

Tyr Tyr Ile Ser Leu Arg His Tyr Tyr Asn Trp Leu Thr Arg Gln Arg
20 25 30

Tyr

<210> SEQ ID NO 164
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 164

Ala Pro Ala Lys Pro Glu Glu Asp Ala Ser Pro Glu Glu Leu Gln Arg
1 5 10 15

Tyr Tyr Ile Ala Leu Arg His Tyr Tyr Asn Trp Leu Thr Arg Gln Arg
20 25 30

Tyr

<210> SEQ ID NO 165
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 165

Ala Pro Ala Lys Pro Glu Glu Ala Ala Glu Pro Glu Glu Leu Gln Arg
1 5 10 15

Tyr Tyr Val Ala Leu Arg His Tyr Tyr Asn Trp Leu Thr Arg Gln Arg
20 25 30

Tyr

<210> SEQ ID NO 166
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 166

```
Ala Pro Glu Lys Pro Glu Glu Asp Ala Thr Pro Glu Glu Glu Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 167
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 167

```
Ala Pro Glu Lys Pro Glu Ala Asp Ala Ser Pro Glu Glu Leu Gln Arg
1               5                   10                  15

Tyr Tyr Val Ala Leu Arg His Tyr Tyr Asn Trp Leu Thr Arg Gln Arg
            20                  25                  30

Tyr
```

<210> SEQ ID NO 168
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 168

```
Ala Pro Glu Lys Pro Glu Glu Asp Ala Thr Pro Glu Glu Ile Gln Arg
1               5                   10                  15

Tyr Tyr Gln Ser Leu Arg His Tyr Tyr Asn Trp Leu Thr Arg Gln Arg
            20                  25                  30

Tyr
```

<210> SEQ ID NO 169
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 169

```
Ala Pro Ala Lys Pro Pro Glu Asp Ala Glu Pro Glu Glu Leu Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 170
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 170

Ala Pro Ala Lys Pro Glu Glu Asp Ala Ser Pro Glu Glu Leu Gln Arg
1 5 10 15

Tyr Tyr Val Glu Leu Arg His Tyr Tyr Asn Trp Leu Thr Arg Gln Arg
20 25 30

Tyr

<210> SEQ ID NO 171
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 171

Ala Pro Ala Lys Pro Glu Glu Ala Ala Glu Pro Glu Glu Ile Gln Arg
1 5 10 15

Tyr Tyr Val Ala Leu Arg His Tyr Tyr Asn Trp Leu Thr Arg Gln Arg
20 25 30

Tyr

<210> SEQ ID NO 172
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 172

Ala Pro Glu Lys Pro Glu Glu Asp Ala Thr Pro Glu Glu Ile Gln Arg
1 5 10 15

Tyr Tyr Ser Ser Leu Arg His Tyr Tyr Asn Trp Leu Thr Arg Gln Arg
20 25 30

Tyr

<210> SEQ ID NO 173
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 173

```
Ala Pro Glu Lys Pro Glu Glu Asp Ala Glu Pro Glu Glu Leu Gln Ala
1               5                   10                  15

Tyr Tyr Val Ser Leu Arg His Tyr Tyr Asn Trp Leu Thr Arg Gln Arg
            20                  25                  30

Tyr
```

<210> SEQ ID NO 174
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 174

```
Ala Pro Glu Lys Pro Glu Glu Asp Ala Ala Pro Glu Glu Ile Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 175
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:

<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 175

Ala Pro Glu Lys Pro Glu Ala Asp Ala Ser Pro Glu Glu Leu Gln Arg
1 5 10 15

Tyr Tyr Val Glu Leu Arg His Tyr Tyr Asn Trp Leu Thr Arg Gln Arg
20 25 30

Tyr

<210> SEQ ID NO 176
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 176

Ala Pro Glu Lys Pro Pro Glu Asp Ala Ser Pro Glu Glu Ile Gln Arg
1 5 10 15

Tyr Tyr Val Ser Leu Arg His Tyr Tyr Asn Trp Leu Thr Arg Gln Arg
20 25 30

Tyr

<210> SEQ ID NO 177
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 177

Ala Pro Glu Lys Pro Glu Glu Asp Ala Thr Pro Glu Glu Leu Gln Arg
1 5 10 15

Tyr Tyr Val Ser Leu Arg His Tyr Tyr Asn Trp Leu Thr Arg Gln Arg
20 25 30

Tyr

<210> SEQ ID NO 178
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 178

Ala Pro Glu Lys Pro Gly Ala Asp Ala Ser Pro Glu Lys Leu Gln Arg
1 5 10 15

Tyr Tyr Val Ser Leu Arg His Tyr Tyr His Lys Leu Thr Arg Gln Arg
20 25 30

Tyr

<210> SEQ ID NO 179
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 179

Ala Pro Ala Lys Pro Glu Glu Asp Ala Glu Pro Glu Glu Leu Gln Arg
1 5 10 15

Tyr Tyr Ile Ala Leu Arg His Tyr Tyr Asn Trp Leu Thr Arg Gln Arg
20 25 30

Tyr

<210> SEQ ID NO 180
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 180

```
Ala Pro Glu Lys Pro Glu Glu Asp Ala Thr Pro Glu Glu Ile Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 181
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 181

```
Ala Pro Glu Lys Pro Glu Glu Asp Ala Thr Pro Glu Glu Leu Gln Gln
1               5                   10                  15

Tyr Tyr Val Ser Leu Arg His Tyr Tyr Asn Trp Leu Thr Arg Gln Arg
            20                  25                  30

Tyr
```

<210> SEQ ID NO 182
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 182

Ala Pro Glu Lys Pro Glu Ala Ala Ala Thr Pro Glu Glu Ile Gln Arg
1 5 10 15

Tyr Tyr Val Ala Leu Arg His Tyr Tyr Asn Trp Leu Thr Arg Gln Arg
20 25 30

Tyr

<210> SEQ ID NO 183
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 183

Ala Pro Glu Lys Pro Glu Ala Asp Ala Ser Pro Glu Glu Thr Gln Arg
1 5 10 15

Tyr Tyr Val Ala Leu Arg His Tyr Tyr Asn Trp Leu Thr Arg Gln Arg
20 25 30

Tyr

<210> SEQ ID NO 184
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:

```
<223> OTHER INFORMATION: See specification as filed for detailed
      description of substitutions and preferred embodiments

<400> SEQUENCE: 184

Ala Pro Glu Lys Pro Glu Glu Asp Ala Thr Pro Glu Glu Leu Gln Arg
1               5                   10                  15

Tyr Tyr Val Ser Leu Arg His Tyr Tyr Asn Trp Leu Thr Lys Gln Arg
            20                  25                  30

Tyr


<210> SEQ ID NO 185
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 185

Ala Pro Ala Lys Pro Glu Ala Asp Ala Glu Pro Glu Glu Ile Gln Arg
1               5                   10                  15

Tyr Tyr Val Ala Leu Arg His Tyr Tyr Asn Trp Leu Thr Arg Gln Arg
            20                  25                  30

Tyr


<210> SEQ ID NO 186
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 186

Ala Pro Ala Lys Pro Glu Glu Asp Ala Ser Pro Glu Glu Ala Gln Arg
1               5                   10                  15

Tyr Tyr Val Ala Leu Arg His Tyr Tyr Asn Trp Leu Thr Arg Gln Arg
            20                  25                  30
```

Tyr

<210> SEQ ID NO 187
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 187

```
Ala Pro Glu Lys Ala Glu Glu Asp Ala Ser Pro Glu Glu Ile Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 188
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 188

```
Ala Pro Glu Lys Pro Glu Ala Asp Ala Thr Pro Glu Glu Ile Gln Arg
1               5                   10                  15

Tyr Tyr Val Ala Leu Arg His Tyr Tyr Asn Trp Leu Thr Arg Gln Arg
            20                  25                  30

Tyr
```

<210> SEQ ID NO 189
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:

<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 189

Ala Pro Ala Lys Pro Glu Glu Asp Ala Ser Glu Glu Glu Leu Gln Arg
1 5 10 15

Tyr Tyr Val Ser Leu Arg His Tyr Tyr Asn Trp Leu Thr Arg Gln Arg
20 25 30

Tyr

<210> SEQ ID NO 190
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 190

Ala Pro Glu Lys Pro Glu Glu Asp Ala Glu Pro Glu Glu Ala Gln Arg
1 5 10 15

Tyr Tyr Val Ser Leu Arg His Tyr Tyr Asn Trp Leu Thr Arg Gln Arg
20 25 30

Tyr

<210> SEQ ID NO 191
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 191

```
Ala Pro Glu Lys Pro Glu Glu Asp Ala Thr Pro Glu Glu Pro Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 192
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 192

```
Ala Pro Glu Lys Pro Glu Glu Asp Ala Thr Pro Glu Glu Leu Gln Arg
1               5                   10                  15

Tyr Tyr Val Ser Leu Arg His Tyr Tyr Asn Trp Leu Gln Arg Gln Arg
            20                  25                  30

Tyr
```

<210> SEQ ID NO 193
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 193

```
Ala Pro Ala Lys Pro Glu Glu Asp Ala Ser Pro Glu Glu Thr Gln Arg
1               5                   10                  15

Tyr Tyr Val Ala Leu Arg His Tyr Tyr Asn Trp Leu Thr Arg Gln Arg
            20                  25                  30
```

Tyr

<210> SEQ ID NO 194
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 194

```
Ala Pro Ala Lys Pro Glu Glu Asp Ala Thr Pro Glu Glu Leu Gln Arg
1               5                   10                  15

Tyr Tyr Ile Ser Leu Arg His Tyr Tyr Asn Trp Leu Thr Arg Gln Arg
            20                  25                  30

Tyr
```

<210> SEQ ID NO 195
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 195

```
Ala Pro Glu Lys Pro Glu Glu Asp Ala Thr Pro Glu Glu Ile Gln Arg
1               5                   10                  15

Tyr Tyr Glu Ser Leu Arg His Tyr Tyr Asn Trp Leu Thr Arg Gln Arg
            20                  25                  30

Tyr
```

<210> SEQ ID NO 196
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 196

Ala Pro Glu Lys Pro Glu Ala Pro Ala Ser Pro Glu Glu Leu Gln Arg
1 5 10 15

Tyr Tyr Val Ser Leu Arg His Tyr Tyr Asn Trp Leu Thr Arg Gln Arg
20 25 30

Tyr

<210> SEQ ID NO 197
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 197

Ala Pro Glu Lys Pro Glu Glu Glu Ala Ser Pro Glu Glu Ile Gln Arg
1 5 10 15

Tyr Tyr Val Ser Leu Arg His Tyr Tyr Asn Trp Leu Thr Arg Gln Arg
20 25 30

Tyr

<210> SEQ ID NO 198
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:

<223> OTHER INFORMATION: C-term amidation
<220> FEATURE:
<223> OTHER INFORMATION: See specification as filed for detailed description of substitutions and preferred embodiments

<400> SEQUENCE: 198

Ala Pro Ala Lys Pro Glu Glu Asp Ala Glu Pro Glu Glu Ile Gln Arg
1 5 10 15

Tyr Tyr Val Ala Leu Arg His Tyr Tyr Asn Trp Leu Thr Arg Gln Arg
20 25 30

Tyr

<210> SEQ ID NO 199
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 199

Ala Pro Ala Lys Pro Glu Glu Asp Ala Ser Pro Glu Glu Ile Gln Arg
1 5 10 15

Tyr Tyr Ile Ser Leu Arg His Tyr Tyr Asn Trp Leu Thr Arg Gln Arg
20 25 30

Tyr

<210> SEQ ID NO 200
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 200

Ala Pro Glu Lys Pro Glu Ala Asp Ala Ser Pro Glu Glu Leu Gln Arg
1 5 10 15

Tyr Tyr Val Ser Leu Arg His Tyr Tyr Asn Trp Leu Thr Arg Gln Arg

-continued

```
20 25 30

Tyr


<210> SEQ ID NO 201
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 201

Ala Pro Glu Lys Pro Glu Glu Asp Ala Ser Pro Glu Glu Ile Gln Arg
1               5                   10                  15

Tyr Tyr Val Ala Leu Arg His Tyr Tyr Asn Trp Leu Thr Arg Gln Arg
            20                  25                  30

Tyr


<210> SEQ ID NO 202
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is
      connected to (6- [(4S)-4-carboxy-4-(17-carboxyheptadecanamido)
      butanamido] hexanoyl
<220> FEATURE:
<223> OTHER INFORMATION: C-term amidation
<220> FEATURE:
<223> OTHER INFORMATION: See specification as filed for detailed
      description of substitutions and preferred embodiments

<400> SEQUENCE: 202

Ala Pro Ala Lys Pro Glu Ala Asp Ala Glu Pro Glu Glu Ile Gln Arg
1               5                   10                  15

Tyr Tyr Val Ser Leu Arg His Tyr Tyr Asn Trp Leu Thr Arg Gln Arg
            20                  25                  30

Tyr


<210> SEQ ID NO 203
<211> LENGTH: 33
<212> TYPE: PRT
<213> ORGANISM: Artificial Sequence
<220> FEATURE:
<223> OTHER INFORMATION: Description of Artificial Sequence: Synthetic
```

polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 203

```
Ala Pro Ala Lys Pro Glu Glu Glu Ala Ser Pro Glu Glu Leu Gln Arg
1               5                   10                  15

Tyr Tyr Val Ser Leu Arg His Tyr Tyr Asn Trp Leu Thr Arg Gln Arg
            20                  25                  30

Tyr
```

<210> SEQ ID NO 204
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 204

```
Arg Pro Glu Lys Pro Gly Glu Asp Ala Ser Pro Glu Glu Leu Gln Arg
1               5                   10                  15

Tyr Tyr Ile Ser Leu Arg His Tyr Tyr Asn Trp Leu Thr Arg Gln Arg
            20                  25                  30

Tyr
```

<210> SEQ ID NO 205
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 205

Arg Pro Glu Lys Pro Gly Glu Asp Ala Ser Pro Glu Glu Leu Gln Arg
1 5 10 15

Tyr Tyr Ile Ser Leu Ala His Tyr Tyr Asn Trp Leu Thr Arg Gln Arg
20 25 30

Tyr

<210> SEQ ID NO 206
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 206

Arg Pro Glu Lys Pro Gly Glu Asp Ala Ser Pro Glu Glu Leu Gln Arg
1 5 10 15

Tyr Tyr Ile Ser Leu Arg His Tyr Tyr Asn Trp Leu Thr Ala Gln Arg
20 25 30

Tyr

<210> SEQ ID NO 207
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PYY analogue
<220> FEATURE:
<223> OTHER INFORMATION: N-term 3-methylbutanoyl
<220> FEATURE:
<221> NAME/KEY: MOD_RES
<222> LOCATION: (4)..(4)
<223> OTHER INFORMATION: Lys, wherein the epsilon amino group of Lys is connected to (6- [(4S)-4-carboxy-4-(17-carboxyheptadecanamido) butanamido] hexanoyl
<220> FEATURE:
<223> OTHER INFORMATION: C-term amidation
<220> FEATURE:
<223> OTHER INFORMATION: See specification as filed for detailed description of substitutions and preferred embodiments

<400> SEQUENCE: 207

Arg Pro Glu Lys Pro Gly Glu Asp Ala Ser Pro Glu Glu Leu Gln Arg
1 5 10 15

-continued

Tyr Tyr Ile Ser Leu Arg His Tyr Tyr Asn Trp Leu Thr Arg Gln Ala
20 25 30

Tyr

<210> SEQ ID NO 208
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Amino acid sequence of formula Ib
<220> FEATURE:
<221> NAME/KEY: MOD_RES
<222> LOCATION: (3)..(3)
<223> OTHER INFORMATION: Ala, Glu or absent
<220> FEATURE:
<221> NAME/KEY: MOD_RES
<222> LOCATION: (4)..(4)
<223> OTHER INFORMATION: Lys, wherein the epsilon amino group of Lys is connected to a half-life extending group
<220> FEATURE:
<221> NAME/KEY: MOD_RES
<222> LOCATION: (5)..(5)
<223> OTHER INFORMATION: Ala, Pro or absent
<220> FEATURE:
<221> NAME/KEY: MOD_RES
<222> LOCATION: (6)..(6)
<223> OTHER INFORMATION: Glu, Gly, Pro or absent
<220> FEATURE:
<221> NAME/KEY: MOD_RES
<222> LOCATION: (7)..(7)
<223> OTHER INFORMATION: Ala, Glu or absent
<220> FEATURE:
<221> NAME/KEY: MOD_RES
<222> LOCATION: (8)..(8)
<223> OTHER INFORMATION: Ala, Asp, Glu, Ile, Leu, Pro, Gln, Ser or absent
<220> FEATURE:
<221> NAME/KEY: MOD_RES
<222> LOCATION: (9)..(9)
<223> OTHER INFORMATION: Ala, Glu, Leu, Pro, Gln, Ser or absent
<220> FEATURE:
<221> NAME/KEY: MOD_RES
<222> LOCATION: (10)..(10)
<223> OTHER INFORMATION: Ala, Glu, Leu, Ser, Gln, Thr, Pro or absent
<220> FEATURE:
<221> NAME/KEY: MOD_RES
<222> LOCATION: (11)..(11)
<223> OTHER INFORMATION: Ala, Glu, Leu, Pro, Gln, Ser or absent
<220> FEATURE:
<221> NAME/KEY: MOD_RES
<222> LOCATION: (12)..(12)
<223> OTHER INFORMATION: Ala, Glu or absent
<220> FEATURE:
<221> NAME/KEY: MOD_RES
<222> LOCATION: (13)..(13)
<223> OTHER INFORMATION: Ala, Glu, Lys or absent
<220> FEATURE:
<221> NAME/KEY: MOD_RES
<222> LOCATION: (14)..(14)
<223> OTHER INFORMATION: Ala, Glu, Ile, Leu, Pro, Gln, Ser, Thr, Val or absent
<220> FEATURE:
<221> NAME/KEY: MOD_RES
<222> LOCATION: (16)..(16)
<223> OTHER INFORMATION: Ala, Glu, Leu, Arg, Lys, Pro, Ser, Gln or absent
<220> FEATURE:
<221> NAME/KEY: MOD_RES
<222> LOCATION: (17)..(17)
<223> OTHER INFORMATION: Gln or Tyr
<220> FEATURE:
<221> NAME/KEY: MOD_RES
<222> LOCATION: (18)..(18)
<223> OTHER INFORMATION: Gln, Tyr or absent

```
<220> FEATURE:
<221> NAME/KEY: MOD_RES
<222> LOCATION: (19)..(19)
<223> OTHER INFORMATION: Ala, Glu, Ile, Leu, Pro, Gln, Ser, Thr, Val or
      absent
<220> FEATURE:
<221> NAME/KEY: MOD_RES
<222> LOCATION: (20)..(20)
<223> OTHER INFORMATION: Ala, Glu, Gly, Leu, Pro, Gln, Ser, Thr, Val or
      absent
<220> FEATURE:
<221> NAME/KEY: MOD_RES
<222> LOCATION: (24)..(24)
<223> OTHER INFORMATION: Gln, Tyr or absent
<220> FEATURE:
<221> NAME/KEY: MOD_RES
<222> LOCATION: (25)..(25)
<223> OTHER INFORMATION: Gln, Tyr or absent
<220> FEATURE:
<221> NAME/KEY: MOD_RES
<222> LOCATION: (26)..(26)
<223> OTHER INFORMATION: His, Asn, Gln or absent
<220> FEATURE:
<221> NAME/KEY: MOD_RES
<222> LOCATION: (27)..(27)
<223> OTHER INFORMATION: Trp, Lys or absent
<220> FEATURE:
<221> NAME/KEY: MOD_RES
<222> LOCATION: (29)..(29)
<223> OTHER INFORMATION: Gln, Leu, Ser, Thr or absent
<220> FEATURE:
<221> NAME/KEY: MOD_RES
<222> LOCATION: (30)..(30)
<223> OTHER INFORMATION: Lys or Arg
<220> FEATURE:
<223> OTHER INFORMATION: See specification as filed for detailed
      description of substitutions and preferred embodiments

<400> SEQUENCE: 208

Ala Pro Xaa Lys Xaa Xaa Xaa Xaa Xaa Xaa Xaa Xaa Xaa Xaa Gln Xaa
1               5                   10                  15

Xaa Xaa Xaa Xaa Leu Arg His Xaa Xaa Xaa Xaa Leu Xaa Xaa Gln Arg
            20                  25                  30

Tyr


<210> SEQ ID NO 209
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of formula IIb
<220> FEATURE:
<221> NAME/KEY: MOD_RES
<222> LOCATION: (3)..(3)
<223> OTHER INFORMATION: Ala or Glu
<220> FEATURE:
<221> NAME/KEY: MOD_RES
<222> LOCATION: (4)..(4)
<223> OTHER INFORMATION: Lys, wherein the epsilon amino group of Lys is
      connected to a half-life extending group
<220> FEATURE:
<221> NAME/KEY: MOD_RES
<222> LOCATION: (5)..(5)
<223> OTHER INFORMATION: Ala or Pro
<220> FEATURE:
<221> NAME/KEY: MOD_RES
<222> LOCATION: (6)..(6)
<223> OTHER INFORMATION: Glu or Pro
<220> FEATURE:
<221> NAME/KEY: MOD_RES
<222> LOCATION: (7)..(7)
<223> OTHER INFORMATION: Ala or Glu
```

<220> FEATURE:
<221> NAME/KEY: MOD_RES
<222> LOCATION: (8)..(8)
<223> OTHER INFORMATION: Ala, Asp or Glu
<220> FEATURE:
<221> NAME/KEY: MOD_RES
<222> LOCATION: (10)..(10)
<223> OTHER INFORMATION: Glu, Ser or Thr
<220> FEATURE:
<221> NAME/KEY: MOD_RES
<222> LOCATION: (11)..(11)
<223> OTHER INFORMATION: Ala, Glu or Pro
<220> FEATURE:
<221> NAME/KEY: MOD_RES
<222> LOCATION: (14)..(14)
<223> OTHER INFORMATION: Ala, Ile, Leu, Ser or Thr
<220> FEATURE:
<221> NAME/KEY: MOD_RES
<222> LOCATION: (16)..(16)
<223> OTHER INFORMATION: Arg or Gln
<220> FEATURE:
<221> NAME/KEY: MOD_RES
<222> LOCATION: (19)..(19)
<223> OTHER INFORMATION: Ile, Thr or Val
<220> FEATURE:
<221> NAME/KEY: MOD_RES
<222> LOCATION: (20)..(20)
<223> OTHER INFORMATION: Ala, Glu, Gln or Ser
<220> FEATURE:
<221> NAME/KEY: MOD_RES
<222> LOCATION: (26)..(26)
<223> OTHER INFORMATION: Asn or Gln
<220> FEATURE:
<223> OTHER INFORMATION: See specification as filed for detailed
      description of substitutions and preferred embodiments

<400> SEQUENCE: 209

```
Ala Pro Xaa Lys Xaa Xaa Xaa Xaa Ala Xaa Xaa Glu Glu Xaa Gln Xaa
1               5                   10                  15

Tyr Tyr Xaa Xaa Leu Arg His Tyr Tyr Xaa Trp Leu Thr Arg Gln Arg
            20                  25                  30

Tyr
```

<210> SEQ ID NO 210
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of formula IIIb
<220> FEATURE:
<221> NAME/KEY: MOD_RES
<222> LOCATION: (3)..(3)
<223> OTHER INFORMATION: Ala or Glu
<220> FEATURE:
<221> NAME/KEY: MOD_RES
<222> LOCATION: (4)..(4)
<223> OTHER INFORMATION: Lys, wherein the epsilon amino group of Lys is
      connected to a half-life extending group
<220> FEATURE:
<221> NAME/KEY: MOD_RES
<222> LOCATION: (6)..(6)
<223> OTHER INFORMATION: Glu, Gly or Pro
<220> FEATURE:
<221> NAME/KEY: MOD_RES
<222> LOCATION: (7)..(7)
<223> OTHER INFORMATION: Ala or Glu
<220> FEATURE:
<221> NAME/KEY: MOD_RES
<222> LOCATION: (8)..(8)
<223> OTHER INFORMATION: Ala, Asp, Glu or Pro
<220> FEATURE:
<221> NAME/KEY: MOD_RES
<222> LOCATION: (9)..(9)
<223> OTHER INFORMATION: Ala or Ser
<220> FEATURE:
<221> NAME/KEY: MOD_RES
<222> LOCATION: (10)..(10)
<223> OTHER INFORMATION: Ala, Glu, Ser, Thr or Pro
<220> FEATURE:
<221> NAME/KEY: MOD_RES
<222> LOCATION: (11)..(11)
<223> OTHER INFORMATION: Ala, Glu or Pro
<220> FEATURE:
<221> NAME/KEY: MOD_RES
<222> LOCATION: (12)..(12)
<223> OTHER INFORMATION: Ala or Glu
<220> FEATURE:
<221> NAME/KEY: MOD_RES
<222> LOCATION: (13)..(13)
<223> OTHER INFORMATION: Ala or Glu
<220> FEATURE:
<221> NAME/KEY: MOD_RES
<222> LOCATION: (14)..(14)
<223> OTHER INFORMATION: Ile, Leu, Thr or Val
<220> FEATURE:
<221> NAME/KEY: MOD_RES
<222> LOCATION: (15)..(15)
<223> OTHER INFORMATION: Glu or Gln
<220> FEATURE:
<221> NAME/KEY: MOD_RES
<222> LOCATION: (16)..(16)
<223> OTHER INFORMATION: Ala, Glu, Arg, Lys, or Gln
<220> FEATURE:
<221> NAME/KEY: MOD_RES
<222> LOCATION: (18)..(18)
<223> OTHER INFORMATION: Glu or Tyr
<220> FEATURE:
<221> NAME/KEY: MOD_RES
<222> LOCATION: (19)..(19)
<223> OTHER INFORMATION: Ile or Val
<220> FEATURE:
<221> NAME/KEY: MOD_RES
<222> LOCATION: (20)..(20)
<223> OTHER INFORMATION: Ala, Glu, Ser or Thr
<220> FEATURE:
<223> OTHER INFORMATION: See specification as filed for detailed
      description of substitutions and preferred embodiments

<400> SEQUENCE: 210

```
Ala Pro Xaa Lys Pro Xaa Xaa Xaa Xaa Xaa Xaa Xaa Xaa Xaa Xaa Xaa
1               5                   10                  15

Tyr Xaa Xaa Xaa Leu Arg His Tyr Tyr Asn Trp Leu Thr Arg Gln Arg
            20                  25                  30

Tyr
```

<210> SEQ ID NO 211
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of formula IVb
<220> FEATURE:
<221> NAME/KEY: MOD_RES
<222> LOCATION: (3)..(3)
<223> OTHER INFORMATION: Ala or Glu
<220> FEATURE:
<221> NAME/KEY: MOD_RES
<222> LOCATION: (6)..(6)
<223> OTHER INFORMATION: Glu or Pro
<220> FEATURE:
<221> NAME/KEY: MOD_RES
<222> LOCATION: (7)..(7)
<223> OTHER INFORMATION: Ala or Glu
<220> FEATURE:

-continued

```
<221> NAME/KEY: MOD_RES
<222> LOCATION: (8)..(8)
<223> OTHER INFORMATION: Ala, Asp or Glu
<220> FEATURE:
<221> NAME/KEY: MOD_RES
<222> LOCATION: (10)..(10)
<223> OTHER INFORMATION: Glu, Ser or Thr
<220> FEATURE:
<221> NAME/KEY: MOD_RES
<222> LOCATION: (14)..(14)
<223> OTHER INFORMATION: Ile or Leu
<220> FEATURE:
<221> NAME/KEY: MOD_RES
<222> LOCATION: (19)..(19)
<223> OTHER INFORMATION: Ile or Val
<220> FEATURE:
<221> NAME/KEY: MOD_RES
<222> LOCATION: (20)..(20)
<223> OTHER INFORMATION: Ala or Ser
<220> FEATURE:
<223> OTHER INFORMATION: See specification as filed for detailed
      description of substitutions and preferred embodiments

<400> SEQUENCE: 211

Ala Pro Xaa Lys Pro Xaa Xaa Xaa Ala Xaa Pro Glu Glu Xaa Gln Arg
1               5                   10                  15

Tyr Tyr Xaa Xaa Leu Arg His Tyr Tyr Asn Trp Leu Thr Arg Gln Arg
            20                  25                  30

Tyr


<210> SEQ ID NO 212
<211> LENGTH: 4
<212> TYPE: PRT
<213> ORGANISM: Homo sapiens

<400> SEQUENCE: 212

Arg Gln Arg Tyr
1
```

SOLUBLE NPY2 RECEPTOR AGONISTS

SEQUENCE LISTING

The instant application contains a Sequence Listing which has been submitted electronically in ASCII format and is hereby incorporated by reference in its entirety. Said ASCII copy, created on Aug. 4, 2021, is named 01-3446-US-1_SL.txt and is 182,619 bytes in size.

FIELD OF THE INVENTION

The present invention relates to PYY analogues that are neuropeptide Y2 (NPY2) receptor agonists, and to their medical use in the treatment and/or prevention of a variety of diseases, conditions or disorders, such as treatment and/or prevention of excess food intake, excess body weight, obesity, metabolic diseases, and other conditions or disorders related to excess body weight or obesity, e.g. diabetes and cardiovascular diseases.

BACKGROUND INFORMATION

Overweight and obesity are defined as abnormal or excessive fat accumulation that presents a risk to health. In this regard, overweight and obesity are major risk factors for a number of chronic diseases, including type 2 diabetes, cardiovascular diseases and cancer. According to the WHO overweight and obesity are no longer considered a problem limited to high income countries but are now dramatically on the rise in low- and middle-income countries. WHO's Global Health Observatory indicate that, in 2016, 39% of women or men aged 18 and over were overweight and 11% of men and 15% of women were obese.

Despite long-standing efforts, the number of overweight and obese patients is still growing. First line therapy for overweight and obese patients comprise diet and exercise but often are not sufficiently efficacious. Second line treatment options are bariatric surgery and pharmacotherapy. Available pharmacological treatments seem to lack in efficacy and/or safety, and only a limited number of approved therapies are available in the US and in Europe.

Therefore, there is still a high medical need for more efficacious and safe treatment options.

NPY (Neuropeptide Y; SEQ ID No:1—human sequence), PYY (Peptide YY; SEQ ID No: 2—human sequence), and PP (Pancreatic Polypeptide; SEQ ID No:3—human sequence) are naturally secreted homologous, 36 amino acid, C-terminally amidated peptides and belong to the PP-fold family of peptides.

```
Sequence of hPYY (3-36):
                                        (SEQ ID No: 4)
Ile Lys Pro Glu Ala Pro Gly Glu Asp Ala Ser Pro

Glu Glu Leu Asn Arg Tyr Tyr Ala Ser Leu Arg His

Tyr Leu Asn Leu Val Thr Arg Gln Arg Tyr
```

PYY is cleaved to PYY(3-36) by dipeptidyl peptidase IV (DPP IV). PYY(3-36) displays increased selectivity for the neuropeptide Y2 receptor over neuropeptide Y1, Y4 and Y5 receptors as compared to PYY(1-36), albeit some Y1 and Y5 affinity is retained. It is believed that PYY or PYY(3-36) exhibits the feeding suppressive action via activation of the neuropeptide Y2 receptor (*Inhibition of Food Intake in Obese Subjects by Peptide* $YY_{3-36}$, N Engl J Med 2003; 349; 941-8).

However, PYY and also PYY(3-36) have a short half-life in the body and show undesirable chemical or physical properties, e.g. low stability. Further, the pharmacologic effect, e.g. its efficacy as body weight lowering agent, seems limited.

WO2014/178018 discloses PYY analogues and their ability to reduce food intake in mice. WO2011/033068 and WO2011/058165 disclose long acting Y2 receptor agonists. WO2015/071355, WO2016/198682 and WO2020/092191 relate to PYY compounds, which are selective Y2 receptor agonists. PYY compounds are disclosed comprising a covalently attached substituent or modifying group also referred therein as a protracting moiety.

There is a need in the art for further (long acting) PYY analogues selectively acting on the NPY2 receptor. For example, it would be desirable to increase further the solubility of PYY analogues, preferably to increase the solubility around pH 7 and/or around pH 6. This would increase the formulation options for a ready-to-use application and potentially allow combinations with other (peptide) therapeutics to improve their efficacy.

It has been found that the PYY analogues of the present invention generally are soluble around pH 6 and pH 7.

BRIEF SUMMARY OF THE INVENTION

In a first aspect, the invention provides a PYY analogue, wherein the analogue comprises i) alanine at the position corresponding to position 4 of hPYY(3-36)

ii) lysine at the position corresponding to position 7 of hPYY(3-36)

iii) the sequence QRY at its C-terminal end, and wherein a half-life extending group is attached to the epsilon amino group of the lysine at position 7 or of a lysine at positions 6, 10, 11, 14, 17, 21, 22 or 30, or to the carboxylic acid group of the side chain of a aspartate or a glutamate at positions 14 or 30.

In some embodiments, the PYY analogue comprises i) alanine at the position corresponding to position 4 of hPYY(3-36)

ii) lysine at the position corresponding to position 7 of hPYY(3-36)

iii) proline at the position corresponding to position 5 of hPYY(3-36)

iv) glutamine at the position corresponding to position 18 of hPYY(3-36)

v) leucine at the position corresponding to position 24 of hPYY(3-36)

vi) arginine at the position corresponding to position 25 of hPYY(3-36)

vii) histidine at the position corresponding to position 26 of hPYY(3-36)

viii) leucine at the position corresponding to position 31 of hPYY(3-36)

ix) the sequence QRY at its C-terminal end, and wherein a half-life extending group is attached to the epsilon amino group of the lysine at position 7 or of a lysine at positions 6, 10, 11, 14, 17, 21 or 22, or to the carboxylic acid group of the side chain of a aspartate or a glutamate at position 14.

In some embodiments of the present invention, the PYY analogue is a compound having the formula:

$$R^1—Z—R^2,$$

wherein $R^1$ is hydrogen, —C(O)$C_{1-6}$ alkyl, —C(O)$C_6H_6$, —C(O)$C_{3-6}$ cycloalkyl, —C(O)$C_{1-6}$ alkyl-$C_{3-6}$ cycloalkyl, $C_{1-6}$ alkyl or $C_{1-6}$ alkyl-$C_{3-6}$ cycloalkyl:

$R^2$ is OH or $NHR^3$, wherein $R^3$ is hydrogen or $C_{1-3}$ alkyl; and

Z is a peptide comprising an amino acid sequence of formula Ib:

```
                                    (SEQ ID NO: 208)
Ala-Pro-X6-Lys-X8-X9-X10-X11-X12-X13-X14-X15-X16-

X17-Gln-X19-X20-X21-X22-X23-Leu-Arg-His-X27-X28-

X29-X30-Leu-X32-X33-Gln-Arg-Tyr
(Ib)
```

wherein

X6 is selected from the group consisting of Ala and Glu;

X8 is selected from the group consisting of Ala and Pro;

X9 is selected from the group consisting of Glu, Gly and Pro;

X10 is selected from the group consisting of Ala and Glu;

X11 is selected from the group consisting of Ala, Asp, Glu, Ile, Leu, Pro, Gln and Ser;

X12 is selected from the group consisting of Ala, Glu, Leu, Pro, Gln and Ser;

X13 is selected from the group consisting of Ala, Glu, Leu, Ser, Gln, Thr and Pro;

X14 is selected from the group consisting of Ala, Glu, Leu, Pro, Gln and Ser;

X15 is selected from the group consisting of Ala and Glu;

X16 is selected from the group consisting of Ala, Glu and Lys;

X17 is selected from the group consisting of Ala, Glu, Ile, Leu, Pro, Gln, Ser, Thr and Val;

X19 is selected from the group consisting of Ala, Glu, Leu, Arg, Lys, Pro, Ser and Gln;

X20 is selected from the group consisting of Gln and Tyr;

X21 is selected from the group consisting of Gln and Tyr;

X22 is selected from the group consisting of Ala, Glu, Ile, Leu, Pro, Gln, Ser, Thr and Val;

X23 is selected from the group consisting of Ala, Glu, Gly, Leu, Pro, Gln, Ser, Thr and Val;

X27 is selected from the group consisting of Gln and Tyr;

X28 is selected from the group consisting of Gln and Tyr;

X29 is selected from the group consisting of His, Asn and Gln;

X30 is selected from the group consisting of Trp and Lys;

X32 is selected from the group consisting of Gln, Leu, Ser and Thr;

X33 is selected from the group consisting of Lys and Arg;

wherein one to three amino acids of X6, X8-17, X19-X23 and X27-X32 may be absent, and wherein a half-life extending group is attached to the epsilon amino group of the lysine at position 7.

In some embodiments, the half-life extending group consists of a lipophilic substituent X and a linker U, wherein the linker U is attached to the amino acid side chain and X is attached to U, and the linker U consists of one, two or three sub-moieties (U1, U2, U3), wherein at least one sub-moiety is Ahx.

In some embodiments, the lipophilic substituent X is selected from the group consisting of 15-carboxy-pentadecanoyl, 17-carboxy-heptadecanoyl (C18DA) and 19-carboxynonadecanoyl, and the linker U consists of one, two or three sub-moieties independently selected from the group consisting of Gly, Glu, γ-Glu, ε-Lys, Ser, Ahx and OEG, or independently selected from the group consisting of γ-Glu, Ahx and OEG.

In some embodiment the PYY analogue is selected from the compounds 245 to 443 described herein.

In some embodiments the PYY analogue is in the form of a salt, preferably in the form of a pharmaceutically acceptable salt.

The invention further provides a composition comprising a PYY analogue as described herein.

The present invention further provides a PYY analogue for use in a method of medical treatment, e.g. for use in the treatment of obesity and various obesity-related conditions, diseases, or disorders such as type 2 diabetes, NAFLD or NASH.

The invention provides a PYY analogue of the invention for use in a method of treating, inhibiting or reducing weight gain, promoting weight loss and/or reducing excess body weight.

DETAILED DESCRIPTION OF THE INVENTION

Terms, Definitions and Conventions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

Throughout this specification, amino acid positions of the PYY analogues are numbered according to the corresponding position in native human PYY having the sequence shown above.

PYY Analogues

A PYY analogue is a peptide comprising an amino acid sequence corresponding to the amino acid sequence of hPYY(3-36). In other words a PYY analogue is a peptide, whose structure is related to PYY, in which one or more amino acid residues have been modified when compared to hPYY(3-36). Possible modifications are substitutions, insertions, or deletions of amino acids at specific positions. A PYY analogue of the invention relates to a peptide that has retained a certain binding affinity (Ki) towards the hNPY2 receptor.

The term "PYY analogue" comprises the peptide itself, i.e., in a non-ionized state, as well as the peptide in ionized state (e.g. when one or more side chains of its amino acids are ionized, i.e. (de)protonated). A PYY analogue in a non-ionized state is also referred to herein as a non-salt form of the PYY analogue.

The term "PYY analogue" may also refer to peptides, in which a half-life extending group is attached to one or more amino acids of the peptide. In such cases, a side chain of an amino acid bears a covalently attached half-life extending group.

As used herein, the term "pharmaceutically acceptable salt" is intended to indicate a salt which is not harmful to a patient or subject to which the salt in question is administered. It may suitably be a salt chosen, e.g., among acid addition salts and basic salts. As used herein, "pharmaceutically acceptable salt" refer to derivatives of the disclosed analogues or compounds wherein the parent analogue or compound is modified by making acid or base salts thereof. Examples of acid addition salts include chloride salts, citrate salts and acetate salts. Examples of basic salts include salts, where the cation is selected among alkali metal cations, such as sodium or potassium ions, alkaline earth metal cations, such as calcium or magnesium ions, as well as substituted ammonium ions, such as ions of the type $N(R^1)(R^2)(R^3)(R^4)^+$, where $R^1$, $R^2$, $R^3$ and $R^4$ independently will typically designate hydrogen or optionally substituted $C_{1-6}$-alkyl. Other examples of pharmaceutically acceptable salts are described in "Remington's Pharmaceutical Sciences", 17th edition, Alfonso R. Gennaro (Ed.), Mark Publishing Company, Easton, PA, USA, 1985 (and more recent editions thereof), in the "Encyclopaedia of Pharmaceutical Technology", 3$^{rd}$ edition, James Swarbrick (Ed.), Informa Healthcare USA (Inc.), NY, USA, 2007, Vol. 5, p. 3177, and in *J. Pharm. Sci.* 66: 2 (1977).

The term "agonist" as employed in the context of the invention refers to a substance that activates the receptor type in question, typically by binding to it (i.e. as a ligand).

Each embodiment of the invention described herein may be taken alone or in combination with one or more other embodiments of the invention.

Throughout the present specification, unless naturally occurring amino acids are referred to by their full name (e.g. alanine, arginine, etc.), they are designated by their conventional three-letter or single-letter abbreviations (e.g. Ala or A for alanine, Arg or R for arginine, etc.).

Unless otherwise indicated, reference is made to the L-isomeric forms of the amino acids in question.

Additional abbreviations include the following:

Hyp: 4-hydroxyproline, e.g. (2S,4R)-4-hydroxyproline [also denoted (4R)-4-hydroxy-L-proline]

γ-Glu: γ-glutamic acid [also denoted gGlu]

The term "$C_{1-n}$ alkyl", wherein n is an integer selected from 2, 3, 4, 5 or 6, either alone or in combination with another radical, denotes an acyclic, saturated, branched or linear hydrocarbon radical with 1 to n C atoms. For example the term $C_{1-5}$-alkyl embraces the radicals $H_3C-$, $H_3C-CH_2-$, $H_3C-CH_2-CH_2-$, $H_3C-CH(CH_3)-$, $H_3C-CH_2-CH_2-CH_2-$, $H_3C-CH_2-CH(CH_3)-$, $H_3C-CH(CH_3)-CH_2-$, $H_3C-C(CH_3)_2-$, $H_3C-CH_2-CH_2-CH_2-CH_2-$, $H_3C-CH_2-CH_2-CH(CH_3)-$, $H_3C-CH_2-CH(CH_3)-CH_2-$, $H_3C-CH(CH_3)-CH_2-CH_2-$, $H_3C-CH_2-C(CH_3)_2-$, $H_3C-C(CH_3)_2-CH_2-$, $H_3C-CH(CH_3)-CH(CH_3)-$ and $H_3C-CH_2-CH(CH_2CH_3)-$.

The term "$C_{3-n}$-cycloalkyl", wherein n is an integer from 4 to n, either alone or in combination with another radical denotes a cyclic, saturated, unbranched hydrocarbon radical with 3 to n C atoms. For example, the term $C_{3-6}$-cycloalkyl includes cyclopropyl, cyclobutyl, cyclopentyl and cyclohexyl.

"C(O)" or "C(=O)" refers to a carbonyl group.

Nomenclature of Compounds:

As an example, (SEQ ID NO: 66)
iVal-APAK(C18DA-gGlu-Ahx)PPEDASPEELQRYYVELRHYYNWLT

RQRY-NH2, wherein iVal represents 3-methylbutanoyl (—C(O) CH$_2$CH(CH$_3$)$_2$), C18DA represents 17-carboxyheptadecanoyl, gGlu represents L-γ-glutamyl, connected via its amino-group to C18DA and via its γ-carboxy-group to Ahx, and Ahx represents 6-amino-hexanoyl, connected via its amino-group to gGlu and via its carboxy-group to ε-amino-group of lysine (K), completely defines the PYY analogue of the following structure (SEQ ID NO: 66):

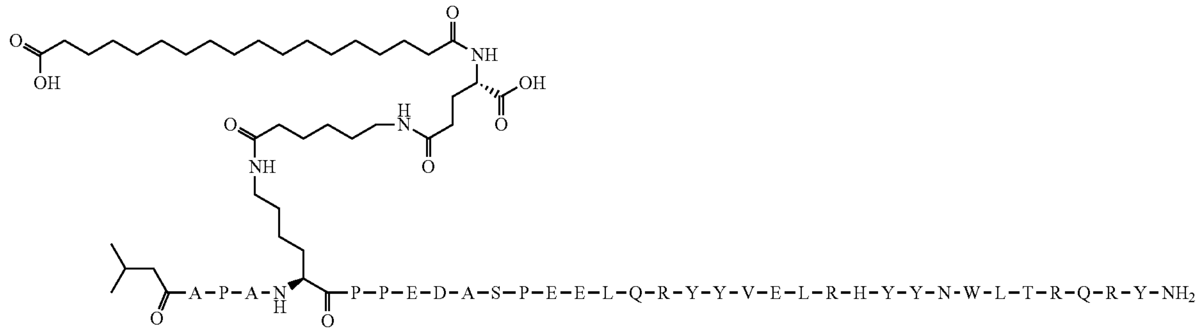

Alternatively, the same compound can be defined in the following way:

N{alpha-4}-(3-methylbutanoyl)-N{epsilon-7}-(6-[(4S)-4-carboxy-4-(17-carboxyheptadecanamido)butanamido]hexanoyl)[4A,6A,7K,9P,18Q,22V,23E,28Y,30W,31L]-hPYY(4-36).

The terms "treatment" and grammatical variants thereof (e.g. "treated", "treating", "treat") as employed in the present context refer to an approach for obtaining beneficial or desired clinical results. For the purposes of this invention, beneficial or desired clinical results include, but are not limited to, alleviation of symptoms, diminishment of extent of disease, stabilization (i.e. not worsening) of state of disease, delay or slowing of disease progression, amelioration or palliation of the disease state, and remission (whether partial or total), whether detectable or undetectable. "Treatment" can also mean prolonging survival relative to expected survival time if not receiving treatment. A subject (e.g. a human) in need of treatment may thus be a subject already afflicted with the disease or disorder in question. The term "treatment" includes inhibition or reduction of an increase in severity of a pathological state or symptoms (e.g. weight gain or hyperglycemia) relative to the absence of treatment and is not necessarily meant to imply complete cessation of the relevant disease, disorder or condition.

The terms "prevention" and grammatical variants thereof (e.g., "prevented", "preventing", "prevent") as employed in the present context refer to an approach for hindering or preventing the development of, or altering the pathology of, a condition, disease or disorder. Accordingly, "prevention" may refer to prophylactic or preventive measures. For the purposes of this invention, beneficial or desired clinical results include, but are not limited to, prevention or slowing of symptoms, progression or development of a disease, whether detectable or undetectable. A subject (e.g. a human) in need of "prevention" may thus be a subject not yet afflicted with the disease or disorder in question. The term "prevention" thus includes inhibiting or slowing the onset of disease relative to the absence of treatment and is not necessarily meant to imply permanent prevention of the relevant disease, disorder or condition.

Half-Life Extending Group

As described herein, a half-life extending group is covalently attached to a functional group of a side chain of an amino acid of the PYY analogue. The half-life extending group comprises or consists of a lipophilic substituent (X) and optionally a linker (U), wherein one end of the linker U (if present) is attached to an amino acid of the PYY analogue and the other end is connected to the lipophilic substituent (—U—X).

Without wishing to be bound by any particular theory, it is thought that such lipophilic substituents (and other classes of half-life extending moieties) bind albumin and other plasma components in the blood stream, thereby shielding the compound of the invention from renal filtration as well as enzymatic degradation and thus possibly enhancing the half-life of the compound in vivo. The lipophilic substituent may also modulate the potency of the compound as an agonist to the NPY2 receptor or other receptors of the NPY receptor family.

The lipophilic substituent X is attached to the linker U via an ester, ether, a sulfonyl ester, a thioester, an amide, an amine, triazole or a sulfonamide. Accordingly, it will be understood that preferably the lipophilic substituent X includes an acyl group, a sulfonyl group, an alkyne, an azide, an N atom, an O atom or an S atom, which forms part of the ester, sulfonyl ester, thioester, triazole, amide, amine or sulfonamide. Preferably, an acyl group, or an O or N atom in the lipophilic substituent X forms part of an amide or ester with the linker U.

The half-life extending group (the linker U thereof, if present) is attached to an amino acid residue of the PYY analogue via an ester, a sulfonyl ester, a thioester, an amide, an amine or a sulfonamide. Accordingly, it will be understood that preferably the half-life extending group (the linker U thereof, if present) includes an acyl group, a sulfonyl group, an N atom, an O atom or an S atom, which forms part of the ester, sulfonyl ester, thioester, amide, amine or sulfonamide. Preferably, an acyl group, or an O or N atom in the linker U forms part of an amide or ester with the amino acid residue.

The lipophilic substituent X may comprise a hydrocarbon chain having from 10 to 24 C atoms, e.g. from 14 to 22 C atoms, e.g. from 16 to 20 C atoms. Preferably, it has at least 14 C atoms, and preferably has 20 C atoms or fewer. For example, the hydrocarbon chain may contain 14, 15, 16, 17, 18, 19 or 20 carbon atoms. The hydrocarbon chain may be linear or branched and may be saturated or unsaturated. Furthermore, it can include a functional group at the end of the hydrocarbon chain, e.g. a carboxylic acid group, a sulphonic acid group, or a tetrazole group. From the discussion above it will also be understood that the hydrocarbon chain is preferably substituted with a moiety, which forms part of the attachment to an amino acid residue of the PYY analogue or to the linker U, for example an acyl group, a sulfonyl group, an N atom, an O atom or an S atom.

Most preferably, the hydrocarbon chain is substituted with an acyl group (for the attachment to the linker U), and accordingly the hydrocarbon chain may be part of an alkanoyl group, for example a dodecanoyl, 2-butyloctanoyl, tetradecanoyl, hexadecanoyl, heptadecanoyl, octadecanoyl, nonadecanoyl or eicosanoyl group. These hydrocarbon chains substituted with an acyl group at one end may further be functionalized with a carboxylic acid group at the other end of the chain. Examples of functionalized hydrocarbon chains (e.g. lipophilic substituents X) are 15-carboxy-pentadecanoyl, 17-carboxy-heptadecanoyl and 19-carboxy-nonadecanoyl.

In certain embodiments, the linker moiety U may itself comprise one, two, three or more linked sub-moieties ($U^1$, $U^2$, $U^3$, etc). In some of these embodiments the linker may comprise one or more (e.g. one, two or three) linked amino acid residues, which may each independently be a residue of any naturally occurring or non-naturally occurring amino acid. For example, the linker may comprise one, two or three linked amino acid residues, each of which may independently be a residue of Gly, Pro, Ala, Val, Leu, Ile, Cys, Phe, Tyr, His, Lys, Arg, Gln, Asn, α-Glu, γ-Glu, ε-Lys, Asp, β-Asp, Ser, Thr, Aib, AEA (2-(2-aminoethoxy)acetic acid), Ahx (6-aminohexanoic acid), AEEEA (2-{2-[2-(2-aminoethoxy)ethoxy]ethoxy}acetic acid), $H_2N$-dPEG(4)-COOH (15-amino-4,7,10,13-tetraoxa-pentadecanoic acid), $H_2N$-dPEG(6)-COOH (1-amino-3,6,9,12,15,18-hexaoxahenicosan-21-oic acid), $H_2N$-dPEG(12)-COOH (1-amino-3,6,9,12,15,18,21,24,27,30,33,36-dodecaoxanonatriacontan-39-oic acid), OEG-OEG (2-[2-(2-{2-[2-(2-aminoethoxy)ethoxy]acetamido}ethoxy)ethoxy]acetic acid), H-Ebes (3-({2-[2-(2-aminoethoxy)ethoxy]ethyl}carbamoyl)propanoic acid), H-DOOA-DIG-OH (2-[({2-[2-(2-aminoethoxy)ethoxy]ethyl}carbamoyl)methoxy]acetic acid), H-TTD-DIG-OH (2-{[(3-{2-[2-(3-aminopropoxy)ethoxy]ethoxy}propyl)carbamoyl]methoxy} acetic acid), H-TTDS-OH (3-[(3-{2-[2-(3-aminopropoxy)ethoxy]ethoxy}propyl)-carbamoyl]propanoic acid), or 8Ado (i.e. 8-amino-3,6-dioxaoctanoyl also denoted OEG herein).

References to γ-Glu, ε-Lys, and β-Asp indicate residues of amino acids which participate in bonds via their side chain carboxyl or amine functional groups. Thus γ-Glu, and β-Asp participate in bonds via their alpha amino and side chain carboxyl groups, while ε-Lys participates via its carboxyl and side chain amino groups. In the context of the present invention, γ-Glu, gGlu and isoGlu are used interchangeably.

In certain embodiments, the linker U consists of one, two or three independently selected sub-moieties ($U^1$, $U^2$, $U^3$) selected from the group consisting of Ala, Glu, γ-Glu, Gly, ε-Lys, Ser, Ahx, Ahx-Ahx, OEG and OEG-OEG.

Linkers comprising Ahx as sub-moiety (e.g. γ-Glu-Ahx, Ahx-γ-Glu, Ahx-Ahx, γ-Glu-γ-Glu-Ahx, Ahx-γ-Glu-γ-Glu) may be preferred.

Synthesis of PYY Analogues

The invention provides a method of synthesis of a PYY analogue of the invention. The PYY analogues may be manufactured by standard synthetic methods, including standard solid-phase or liquid-phase methodology. Peptides are assembled either stepwise or by merging fragments, and optionally isolated and purified yielding the final peptide product. Synthesis examples are described in numerous publications, including Fields, G. B. et al., "Principles and Practice of Solid-Phase Peptide Synthesis" in Synthetic Peptides, Grant G. A. (ed.), Oxford University Press ($2^{nd}$ edition, 2002).

Embodiments

In a first aspect, the invention provides a PYY analogue, wherein the analogue comprises i) alanine at the position corresponding to position 4 of hPYY(3-36)

ii) lysine at the position corresponding to position 7 of hPYY(3-36)

iii) the sequence QRY at its C-terminal end, and wherein a half-life extending group is attached to the epsilon amino group of the lysine at position 7 or of a lysine at positions 6, 10, 11, 14, 17, 21, 22 or 30, or to the carboxylic acid group of the side chain of a aspartate or a glutamate at positions 14 or 30.

In some embodiments, the PYY analogue comprises proline at the position corresponding to position 5 of hPYY (3-36).

In some embodiments, the PYY analogue comprises glutamine at the position corresponding to position 18 of hPYY(3-36).

In some embodiment, the PYY analogue comprises leucine at the position corresponding to position 24 of hPYY (3-36).

In some embodiments, the PYY analogue comprises arginine at the position corresponding to position 25 of hPYY(3-36).

In some embodiments, the PYY analogue comprises histidine at the position corresponding to position 26 of hPYY(3-36).

In some embodiments, the PYY analogue comprises leucine at the position corresponding to position 31 of hPYY(3-36).

In some embodiments, the PYY analogue comprises arginine or lysine at the position corresponding to position 33 of hPYY(3-36).

In some embodiments, the PYY analogue bears a half-life extending group, which is attached to the epsilon amino group of the lysine at position 7.

In some embodiments of the present invention, the half-life extending group consists of a lipophilic substituent X and a linker U, wherein the linker U is attached to the amino acid side chain, and X is attached to U.

In some embodiments the linker U consists of one, two or three sub-moieties (U1, U2, U3), wherein at least one sub-moiety is Ahx.

In some embodiments, the PYY analogue comprises i) alanine at the position corresponding to position 4 of hPYY(3-36)

ii) lysine at the position corresponding to position 7 of hPYY(3-36)

iii) proline at the position corresponding to position 5 of hPYY(3-36)

iv) glutamine at the position corresponding to position 18 of hPYY(3-36)

v) leucine at the position corresponding to position 24 of hPYY(3-36)

vi) arginine at the position corresponding to position 25 of hPYY(3-36)

vii) histidine at the position corresponding to position 26 of hPYY(3-36) viii leucine at the position corresponding to position 31 of hPYY(3-36)

ix) the sequence QRY at its C-terminal end, and wherein a half-life extending group is attached to the epsilon amino group of the lysine at position 7 or of a lysine at positions 6, 10, 11, 14, 17, 21 or 22, or to the carboxylic acid group of the side chain of a aspartate or a glutamate at position 14.

In some embodiments, the PYY analogue comprises arginine at the position corresponding to position 33 of hPYY(3-36).

In some embodiments, the PYY analogue comprises tryptophan or lysine at the position corresponding to position 30 of hPYY(3-36).

In some embodiments, the PYY analogue comprises glutamine or tyrosine at the position corresponding to position 28 of hPYY(3-36).

In some embodiments, the PYY analogue comprises glutamine or tyrosine at the position corresponding to position 27 of hPYY(3-36).

In some embodiments, the PYY analogue comprises glutamine or tyrosine at the position corresponding to position 21 of hPYY(3-36).

In some embodiments, the PYY analogue comprises glutamine or tyrosine at the position corresponding to position 20 of hPYY(3-36).

In some embodiments, the PYY analogue comprises alanine or glutamic acid at the position corresponding to position 15 of hPYY(3-36).

In some embodiments, the PYY analogue comprises alanine or glutamic acid at the position corresponding to position 10 of hPYY(3-36).

In some embodiments, the PYY analogue comprises alanine or proline at the position corresponding to position 8 of hPYY(3-36).

In some embodiments, the PYY analogue comprises alanine or glutamic acid at the position corresponding to position 6 of hPYY(3-36).

In some embodiments, the PYY analogue bears a half-life extending group, which is attached to the epsilon amino group of the lysine at position 7.

In some embodiments, the PYY analogue comprises i) alanine at the position corresponding to position 4 of hPYY(3-36)

iii) proline at the position corresponding to position 5 of hPYY(3-36)

iv) alanine or glutamic acid at the position corresponding to position 6 of hPYY(3-36)

v) lysine at the position corresponding to position 7 of hPYY(3-36)

vi) alanine or proline at the position corresponding to position 8 of hPYY(3-36)

vii) alanine or glutamic acid at the position corresponding to position 10 of hPYY(3-36)

viii) alanine or glutamic acid at the position corresponding to position 15 of hPYY(3-36)

ix) glutamine at the position corresponding to position 18 of hPYY(3-36)

x) glutamine or tyrosine at the position corresponding to position 20 of hPYY(3-36)

xi) glutamine or tyrosine at the position corresponding to position 21 of hPYY(3-36)

xii) leucine at the position corresponding to position 24 of hPYY(3-36)

xiii) arginine at the position corresponding to position 25 of hPYY(3-36)

xiv) histidine at the position corresponding to position 26 of hPYY(3-36)

xv) glutamine or tyrosine at the position corresponding to position 27 of hPYY(3-36)

xvi) glutamine or tyrosine at the position corresponding to position 28 of hPYY(3-36)

xvii) tryptophan or lysine at the position corresponding to position 30 of hPYY(3-36)

xviii) leucine at the position corresponding to position 31 of hPYY(3-36)

xix) the sequence RQRY (SEQ ID NO: 212) at its C-terminal end, and wherein a half-life extending group is attached to the epsilon amino group of the lysine at position 7 or of a lysine at positions 11, 14, 17, or 22, or to the carboxylic acid group of the side chain of a aspartate or a glutamate at position 14.

In some embodiments, exactly one half-life extending group is attached to the PYY analogue, said half-life extending group being attached to the epsilon amino group of the lysine at position 7.

In some embodiments according the previous paragraph, the linker U of the half-life extending group consists of one, two or three sub-moieties (U1, U2, U3), wherein at least one sub-moiety is Ahx.

In some embodiments of the present invention, the PYY analogue is a compound having the formula:

$R^1$—Z—$R^2$, wherein $R^1$ is hydrogen, —C(O)$C_{1-6}$ alkyl, —C(O)$C_6H_6$, —C(O)$C_{3-6}$ cycloalkyl, —C(O)$C_{1-6}$ alkyl-$C_{3-6}$ cycloalkyl, $C_{1-6}$ alkyl or $C_{1-6}$ alkyl-$C_{3-6}$ cycloalkyl:

$R^2$ is OH or $NHR^3$, wherein $R^3$ is hydrogen or $C_{1-3}$ alkyl; and

Z is a peptide comprising an amino acid sequence of formula Ib:

```
                                        (SEQ ID NO: 208)
Ala-Pro-X6-Lys-X8-X9-X10-X11-X12-X13-X14-X15-X16-

X17-Gln-X19-X20-X21-X22-X23-Leu-Arg-His-X27-X28-

X29-X30-Leu-X32-X33-Gln-Arg-Tyr
(Ib)
```

wherein

X6 is selected from the group consisting of Ala and Glu;

X8 is selected from the group consisting of Ala and Pro;

X9 is selected from the group consisting of Glu, Gly and Pro;

X10 is selected from the group consisting of Ala and Glu;

X11 is selected from the group consisting of Ala, Asp, Glu, Ile, Leu, Pro, Gln and Ser;

X12 is selected from the group consisting of Ala, Glu, Leu, Pro, Gln and Ser;

X13 is selected from the group consisting of Ala, Glu, Leu, Ser, Gln, Thr and Pro;

X14 is selected from the group consisting of Ala, Glu, Leu, Pro, Gln and Ser;

X15 is selected from the group consisting of Ala, and Glu;

X16 is selected from the group consisting of Ala, Glu and Lys;

X17 is selected from the group consisting of Ala, Glu, Ile, Leu, Pro, Gln, Ser, Thr and Val;

X19 is selected from the group consisting of Ala, Glu, Leu, Arg, Lys, Pro, Ser and Gln;

X20 is selected from the group consisting of Gln and Tyr;

X21 is selected from the group consisting of Gln and Tyr;

X22 is selected from the group consisting of Ala, Glu, Ile, Leu, Pro, Gln, Ser, Thr and Val;

X23 is selected from the group consisting of Ala, Glu, Gly, Leu, Pro, Gln, Ser, Thr and Val;

X27 is selected from the group consisting of Gln and Tyr;

X28 is selected from the group consisting of Gln and Tyr;

X29 is selected from the group consisting of His, Asn and Gln;

X30 is selected from the group consisting of Trp and Lys;

X32 is selected from the group consisting of Gln, Leu, Ser and Thr;

X33 is selected from the group consisting of Lys and Arg;

wherein one to three amino acids of X6, X8-X19, X21-X23 and X27-X32 may be absent, and wherein a half-life extending group is attached to the epsilon amino group of the lysine at position 7.

In a further embodiment the PYY analogue is according to the previous embodiment, wherein one of X6, X8-17, X19-X23 and X27-X32 is absent is absent.

In a further embodiment the PYY analogue is according to the previous embodiment, wherein none of X6, X8-17, X19-X23 and X27-X32 is absent.

In a further embodiment $R^1$ is —C(O)$C_{1-4}$ alkyl, —C(O) $C_{3-5}$ cycloalkyl, —C(O)$C_{1-3}$ alkyl$C_{3-4}$ cycloalkyl, $C_{1-4}$ alkyl or $C_{1-3}$ alkyl-$C_{3-4}$ cycloalkyl.

In a further embodiment $R^1$ is —C(O)$CH_2CH(CH_3)_2$, —C(O)$CH_2$-cyclobutyl, —C(O)$CH_2$-cyclopropyl.

It has been found that the PYY analogues of the present invention—bearing alanine at position 4 and lysine at position 7—generally are soluble around pH 6 and pH 7.

Peptide therapeutics are usually provided as pharmaceutical liquid formulation in a prefilled ready-to-use injection device. These peptide formulations for subcutaneous administration have limited application volumes. Therefore, good solubility of the peptides is a requirement for the application in a ready-to-use injection device.

A further important aspect is the long-term stability and solubility of the peptides in the liquid formulation. A property of fundamental importance for physical stability is the intrinsic solubility (at a given pH value).

A broad pH range, within which a peptide therapeutic is reasonably soluble (solubility window), is also desirable as it allows more flexibility for pharmaceutical formulation development. This flexibility might be desirable as other factors, such as chemical stability, are also pH dependent. In general, a peptide formulation around pH 6.0 is believed to show reduced rates of oxidation (e.g. Cys oxidation, disulphide crosslinking, and oxidation of Trp residues), deamination and aspartate isomerization as compared to a formulation at pH 7. For instance, Bak et al. (A. Bak, D. Leung, S. E. Barrett, S. Forster, E. D. Minnihan, A. W. Leithead, J. Cunningham, N. Toussaint, L. S. Crocker, The AAPS Journal, Vol. 17, No. 1, 2015, p. 144-155) states that oxidation propensity generally lessens at lower pH and suggests maintenance at pH <7 as a strategy for mitigation risks related to oxidation. Therefore, it might be desirable to have the option to formulate around pH 6 in case chemical stability of peptides containing asparagine, aspartate or glutamine, tryptophan, cysteine or methionine is an issue.

Efficacy of obesity therapeutics is limited. However, efficacy might be improved by combining different therapeutic principles. NPY2 receptor agonists seem attractive partners for combination with other weight reducing therapeutics. For example, NPY2 receptor agonists show enhanced weight loss efficacy with GLP-1 receptor agonists (e.g. WO2005/077072, WO2014/178018, WO2018/081370) or amylin (e.g. WO2006/066024, WO2009/064298). Native amylin and many amylin (or calcitonin) analogues comprise a disulphide bridge. Therefore, a fix-dose combination of a PYY analogue with an amylin analogue might benefit from the opportunity to formulate at a lower pH where the disulphide bridge of the amylin analogue potentially shows improved stability (e.g. due to reduced intramolecular disulphide bond crosslinking reactions). This illustrates that the advantage to be able to formulate at a pH below 7 may not (only) be due to a higher stability of the NPY analogue but may lie therein that the combination partner shows improved stability (or solubility) at a lower pH.

Therefore, to enable co-formulation development with a diverse range of partners, it is highly desirable to identify NPY2 receptor agonists with a wide solubility window.

Increased solubility, however, should not come at the cost of reduced activity or potency. It was surprisingly found that the alanine at position 4 increases solubility around pH 6 in the PYY analogues of the invention with no or only small negative effects on activity or potency or other important properties (e.g. chemical or physical stability).

Long in-vivo half-life is also a beneficial property for agents to reduce food intake in overweight or obese patients. Compounds with a long-acting profile (as compared to the very short in-vivo half-life of native (human) PYY) reducing the frequency of administration are desirable.

In one aspect, the invention relates to PYY analogues being NPY2 receptor agonists.

In one aspect, the invention relates to PYY analogues showing selectivity towards the NPY receptor subtype Y2 as compared to Y receptor subtypes Y1, Y4 and Y5.

In one aspect, the invention relates to PYY analogues with extended half-live, e.g. with longer half-life than the half-life of hPYY(3-36). For example, the PYY analogues of the invention are suitable for once weekly administration.

Additionally or alternatively, the invention relates to PYY analogues having high chemical and/or physical stability, e.g. around pH 6 or pH 7.

Further, more specific embodiments are defined below:

In an embodiment of the present invention, the PYY analogue is a compound having the formula:

$R^1$—Z—$R^2$, wherein $R^1$ and $R^2$ are as defined above;

Z is an amino acid sequence of formula Ib; and wherein a half-life extending group is attached to the epsilon amino group of the lysine at position 7 and consists of a lipophilic substituent X and a linker U, wherein the linker U is attached to the amino acid side chain and X is attached to U, and the linker U consists of one, two or three sub-moieties (U1, U2, U3), wherein at least one sub-moiety is Ahx.

In a further embodiment of the present invention, the PYY analogue is a compound having the formula:

$R^1$—Z—$R^2$, wherein $R^1$ is hydrogen, —$C(O)C_{1-6}$ alkyl, —$C(O)C_6H_6$, —$C(O)C_{3-6}$ cycloalkyl, —$C(O)C_{1-6}$ alkyl-$C_{3-6}$ cycloalkyl, or $C_{1-6}$ alkyl or $C_{1-6}$ alkyl-$C_{3-6}$ cycloalkyl:

$R^2$ is OH or $NHR^3$, wherein $R^3$ is hydrogen or $C_{1-3}$ alkyl; and

Z is an amino acid sequence of formula IIb:

```
                                    (SEQ ID NO: 209)
Ala-Pro-X6-Lys-X8-X9-X10-X11-Ala-X13-X14-Glu-Glu-

X17-Gln-X19-Tyr-Tyr-X22-X23-Leu-Arg-His-Tyr-Tyr-

X29-Trp-Leu-Thr-Arg-Gln-Arg-Tyr
(IIb)
```

wherein

X6 is selected from the group consisting of Ala and Glu;

X8 is selected from the group consisting of Ala and Pro;

X9 is selected from the group consisting of Glu and Pro;

X10 is selected from the group consisting of Ala and Glu;

X11 is selected from the group consisting of Ala, Asp and Glu;

X13 is selected from the group consisting of Glu, Ser and Thr;

X14 is selected from the group consisting of Ala, Glu and Pro;

X17 is selected from the group consisting of Ala, Ile, Leu, Ser and Thr;

X19 is selected from the group consisting of Arg and Gln;

X22 is selected from the group consisting of Ile, Thr and Val;

X23 is selected from the group consisting of Ala, Glu, Gln and Ser;

X29 is selected from the group consisting of Asn and Gln;

and wherein a half-life extending group is attached to the epsilon amino group of the lysine at position 4.

According to a further embodiment, up to three residues of X6 to X23 are Ala. According to a further embodiment, at least four residues of X6 to X23 are Glu. In a further embodiment, at least four residues of X6, X9, X10, X13, X15, X16 and X23 are Glu.

According to a further embodiment, up to three residues of X6 to X23 are Ala, and at least four residues of X6, X9, X10, X13, X15, X16 and X23 are Glu.

In an embodiment of the present invention, the PYY analogue is a compound having the formula:

$R^1$—Z—$R^2$,

Wherein $R^1$ and $R^2$ are as defined above;

Z is an amino acid sequence of formula IIb; and wherein a half-life extending group is attached to the epsilon amino group of the lysine at position 7 and consists of a lipophilic substituent X and a linker U, wherein the linker U is attached to the amino acid side chain and X is attached to U, and the linker U consists of one, two or three sub-moieties (U1, U2, U3), wherein at least one sub-moiety is Ahx.

In some embodiments of the present invention, the PYY analogue is a compound having the formula:

$R^1$—Z—$R^2$, wherein $R^1$ is hydrogen, —$C(O)C_{1-6}$ alkyl, —$C(O)C_6H_6$, —$C(O)C_{3-6}$ cycloalkyl, —$C(O)C_{1-6}$ alkyl-$C_{3-6}$ cycloalkyl, or $C_{1-6}$ alkyl or $C_{1-6}$ alkyl-$C_{3-6}$ cycloalkyl:

$R^2$ is OH or $NHR^3$, wherein $R^3$ is hydrogen or $C_{1-3}$ alkyl; and

Z is an amino acid sequence of formula IIIb:

```
                                    (SEQ ID NO: 210)
Ala-Pro-X6-Lys-Pro-X9-X10-X11-X12-X13-X14-X15-X16-

X17-X18-X19-Tyr-X21-X22-X23-Leu-Arg-His-Tyr-Tyr-

Asn-Trp-Leu-Thr-Arg-Gln-Arg-Tyr
(IIIb)
```

wherein

X6 is selected from the group consisting of Ala and Glu;

X9 is selected from the group consisting of Glu, Gly and Pro;

X10 is selected from the group consisting of Ala and Glu;

X11 is selected from the group consisting of Ala, Asp, Glu and Pro;

X12 is selected from the group consisting of Ala and Ser;

X13 is selected from the group consisting of Ala, Glu, Ser, Thr and Pro;

X14 is selected from the group consisting of Ala, Glu and Pro;

X15 is selected from the group consisting of Ala and Glu;
X16 is selected from the group consisting of Ala and Glu;
X17 is selected from the group consisting of Ile, Leu, Thr and Val;
X18 is selected from the group consisting of Glu and Gln;
X19 is selected from the group consisting of Ala, Glu, Arg, Lys, and Gln;
X21 is selected from the group consisting of Glu and Tyr;
X22 is selected from the group consisting of Ile and Val;
X23 is selected from the group consisting of Ala, Glu, Ser and Thr;
and wherein a half-life extending group is attached to the epsilon amino group of the lysine at position 4.

In a further embodiment Z is an amino acid sequence of formula IVb:

```
                                        (SEQ ID NO: 211)
Ala-Pro-X6-Lys-Pro-X9-X10-X11-Ala-X13-Pro-Glu-Glu-

X17-Gln-Arg-Tyr-Tyr-X22-X23-Leu-Arg-His-Tyr-Tyr-

Asn-Trp-Leu-Thr-Arg-Gln-Arg-Tyr
(IVb)
```

wherein
X6 is selected from the group consisting of Ala and Glu;
X9 is selected from the group consisting of Glu and Pro;
X10 is selected from the group consisting of Ala and Glu;
X11 is selected from the group consisting of Ala, Asp and Glu;
X13 is selected from the group consisting of Glu, Ser and Thr;
X17 is selected from the group consisting of Ile and Leu;
X22 is selected from the group consisting of Ile and Val;
X23 is selected from the group consisting of Ala and Ser;

In an embodiment of the present invention, the PYY analogue is a compound having the formula:

$R^1—Z—R^2$,

Wherein $R^1$ and $R^2$ are as defined above;
Z is an amino acid sequence of formula IVb; and
wherein a half-life extending group is attached to the epsilon amino group of the lysine at position 7 and consists of a lipophilic substituent X and a linker U, wherein the linker U is attached to the amino acid side chain and X is attached to U, and the linker U consists of one, two or three sub-moieties (U1, U2, U3), wherein at least one sub-moiety is Ahx.

In further embodiments, the PYY analogue is a compound according to formula Ib, IIb, IIIb, or IVb, wherein up to three residues of X6 to X23 are Ala.

In further embodiments, the PYY analogue is a compound according to formula Ib, IIb, IIIb, or IVb, wherein at least four residues of X6, X9, X10, X13, X15, X16 and X23 are Glu.

In further embodiments, $R^1$ is hydrogen, $—C(O)C_{1-6}$ alkyl, $—C(O)C_{3-6}$ cycloalkyl, or $C_{1-6}$ alkyl.

In further embodiments, $R^1$ is hydrogen or $—C(O)C_{1-6}$ alkyl.

In further embodiments, $R^1$ is hydrogen or $—C(O)C_{1-4}$ alkyl.

In more specific embodiments, $R^1$ is $—C(O)CH_2CH(CH_3)_2$.

In more specific embodiments, $R^2$ is $NH_2$.

In some embodiments of the present invention, the PYY analogue is a compound having the formula:

$R^1—Z—R^2$, wherein $R^1$ and $R^2$ are as defined in any of the definition above; and Z is an amino acid sequence selected from Table 1:

TABLE 1

| cf. compound No | Sequence | SEQ ID NO |
|---|---|---|
| 1 | APEKPEADAEPEELQRYYIALRHYYNWLTRQRY | 5 |
| 2 | APEKPEEDASPEELQRYYIALRHYYNWLTRQRY | 6 |
| 3 | APAKPEADAEPEELQRYYVALRHYYNWLTRQRY | 7 |
| 4 | APEKPEEAAEPEELQRYYVSLRHYYNWLTRQRY | 8 |
| 5 | APAKPEEDASPEELQRQYVSLRHYYNWLTRQRY | 9 |
| 6 | APEKPEADAEPEELQRYYVALRHYYNWLTRQRY | 10 |
| 7 | APEKPEADATPEEIQRYYVSLRHYYNWLTRQRY | 11 |
| 8 | APEKPEEDETPEELQRYYVSLRHYYNWLTRQRY | 12 |
| 9 | APEKPEEQATPEELQRYYVSLRHYYNWLTRQRY | 13 |
| 10 | APAKPEAAAEPEELQRYYVALRHYYNWLTRQRY | 14 |
| 11 | APEKPEADASPEEIQRYYISLRHYYNWLTRQRY | 15 |
| 12 | APEKPEEDASPEELQQYYVSLRHYYHWLTRQRY | 16 |
| 13 | APEKPEADASPEETQRYYVSLRHYYNWLTRQRY | 17 |
| 14 | APEKPPEDASPEELQRYYVSLRHYYNWLTRQRY | 18 |
| 15 | APEKPEEDASPEEIQQYYVSLRHYYNWLTRQRY | 19 |
| 16 | APEKPEEDATPEELQKYYVSLRHYYNWLTRQRY | 20 |
| 17 | APEKPEEDATPEEIQRYYPSLRHYYNWLTRQRY | 21 |
| 18 | APEKPEEDASPEELQRYYVALRHYYNWLTRQRY | 22 |
| 19 | APEKPEEDATEEELQRYYVSLRHYYNWLTRQRY | 23 |
| 20 | APAKPEEDASPEELQRYQVSLRHYYNWLTRQRY | 24 |
| 21 | APEKPEEDAEPEELQRYYVALRHYYNWLTRQRY | 25 |
| 22 | APEKPEEDPTPEELQRYYVSLRHYYNWLTRQRY | 26 |
| 23 | APEKPEEEASPEELQRYYVSLRHYYNWLTRQRY | 27 |
| 24 | APEKPEEDSSPEELQRYYVALRHYYNWLTRQRY | 28 |
| 25 | APEKPEADATPEELQRYYISLRHYYNWLTRQRY | 29 |
| 26 | APAKPEEDATPEELQRYYVSLRHYYNWLTRQRY | 30 |
| 27 | APEKPEEDAEPEESQRYYVSLRHYYNWLTRQRY | 31 |
| 28 | APEKPPEDATPEEIQRYYVSLRHYYNWLTRQRY | 32 |
| 29 | APEKPEADSSPEELQRYYVSLRHYYNWLTRQRY | 33 |
| 30 | APEKPPADATPEELQRYYVSLRHYYNWLTRQRY | 34 |
| 31 | APEKPEEDATPEELQPYYVSLRHYYNWLTRQRY | 35 |
| 32 | APAKPEEDASPEELQRYYVSLRHQYNWLTRQRY | 36 |
| 33 | APAKPEEDAEPEELQRYYISLRHYYNWLTRQRY | 37 |
| 34 | APEKPEEDASAEELQQYYVSLRHYYNWLTRQRY | 38 |
| 35 | APAKPEEAATPEELQRYYVSLRHYYNWLTRQRY | 39 |
| 36 | APAKPEEAATPEEIQRYYVSLRHYYNWLTRQRY | 40 |

TABLE 1-continued

| cf. compound No | Sequence | SEQ ID NO |
|---|---|---|
| 37 | APEKPEEDAEPEELQRYYTSLRHYYNWLTRQRY | 41 |
| 38 | APEKPEEDATPEELQEYYVSLRHYYNWLTRQRY | 42 |
| 39 | APEKPEEDASPEALQEYYVSLRHYYNWLTRQRY | 43 |
| 40 | APEKPEADASPEEIQRYYIALRHYYNWLTRQRY | 44 |
| 41 | APEKPEEDAEPEELQRYYTSLRHYYQWLTRQRY | 45 |
| 42 | APEKPEEPATPEELQRYYVSLRHYYNWLTRQRY | 46 |
| 43 | APAKPEAAAEPEELQRYYVSLRHYYNWLTRQRY | 47 |
| 44 | APEKPEEDATPEELQRYYVGLRHYYNWLTRQRY | 48 |
| 45 | APEKPEEIATPEELQRYYVSLRHYYNWLTRQRY | 49 |
| 46 | APEKPEEDAEPEELQRYYASLRHYYNWLTRQRY | 50 |
| 47 | APEKPPEDASPEEIQRYYVALRHYYNWLTRQRY | 51 |
| 48 | APAKPEEAATPEELQRYYISLRHYYNWLTRQRY | 52 |
| 49 | APEKPEEDATPEELQRYYVLLRHYYNWLTRQRY | 53 |
| 50 | APEKPEEDATPEEIQRYYVALRHYYNWLTRQRY | 54 |
| 51 | APEKPEEDATPEELQRYYVQLRHYYNWLTRQRY | 55 |
| 52 | APEKPEEDASPEEIQRYYVELRHYYNWLTRQRY | 56 |
| 53 | APEKPEEDAEPEEVQRYYVSLRHYYNWLTRQRY | 57 |
| 54 | APEKPEEDATPEEAQRYYVSLRHYYNWLTRQRY | 58 |
| 55 | APEKPEEDASEEEIQRYYVSLRHYYNWLTRQRY | 59 |
| 56 | APEKPEEDATAEELQRYYVSLRHYYNWLTRQRY | 60 |
| 57 | APAKPEEDATPEEAQRYYVSLRHYYNWLTRQRY | 61 |
| 58 | APEKPEEDATPEEVQRYYVSLRHYYNWLTRQRY | 62 |
| 59 | APAKPEEDASPEELQRYYVQLRHYYNWLTRQRY | 63 |
| 60 | APEKPEEDASPEELQRYYVSLRHYYQWLTRQRY | 64 |
| 61 | APEKPPADASPEEIQRYYVSLRHYYNWLTRQRY | 65 |
| 62 | APAKPPEDASPEELQRYYVELRHYYNWLTRQRY | 66 |
| 63 | APAKPEEDASPEEIQRYYVSLRHYYNWLTRQRY | 67 |
| 64 | APEKPPEDATPEEIQRYYVALRHYYNWLTRQRY | 68 |
| 65 | APAKPEEDASPEEIQRYYIALRHYYNWLTRQRY | 69 |
| 66 | APEKPEEDATPEELQRYYISLRHYYNWLTRQRY | 70 |
| 67 | APEKPEEDASPEETQRYYVALRHYYNWLTRQRY | 71 |
| 68 | APEKPEEDAEPEELQRYYVSLRHYYQWLTRQRY | 72 |
| 69 | APEKPPADASPEETQRYYVSLRHYYNWLTRQRY | 73 |
| 70 | APAKPEEDATPEELQRYYIALRHYYNWLTRQRY | 74 |
| 71 | APAKPEEDAEPEELQRYYVALRHYYNWLTRQRY | 75 |
| 72 | APEKPEADAEPEELQRYYVSLRHYYNWLTRQRY | 76 |
| 73 | APEKPEEAASPEELQRYYVALRHYYNWLTRQRY | 77 |
| 74 | APEKPEEDATPEELQRYYVALRHYYNWLTRQRY | 78 |
| 75 | APEKPEEDAPPEEIQRYYVSLRHYYNWLTRQRY | 79 |
| 76 | APEKPEEDASPEELQRYYISLRHYYNWLTRQRY | 80 |
| 77 | APAKPEEDASPEELQRYYVSLRHYQNWLTRQRY | 81 |
| 78 | APAKPEEDASPEELQRYYVSLRHYYQWLTRQRY | 82 |
| 79 | APEKPEEDASPEELQRYYVSLRHYYNWLTRQRY | 83 |
| 80 | APEKPEEDASEAELQRYYVSLRHYYNWLTRQRY | 84 |
| 81 | APEKPEEDAQPEEIQRYYVSLRHYYNWLTRQRY | 85 |
| 82 | APAKPPEDASPEEIQRYYVSLRHYYNWLTRQRY | 86 |
| 83 | APEKPEEDATSEELQRYYVSLRHYYNWLTRQRY | 87 |
| 84 | APEKPEEDATPEEIQRYYVALRHYYNWLTRQRY | 88 |
| 85 | APAKPEEDASPEETQRYYVSLRHYYNWLTRQRY | 89 |
| 86 | APEKPEEDATPEEIQRYYASLRHYYNWLTRQRY | 90 |
| 87 | APEKPEEDATPEELQRYYVPLRHYYNWLTRQRY | 91 |
| 88 | APEKPEEDATPEELQRQYVSLRHYYNWLTRQRY | 92 |
| 89 | APAKPPEDASPEELQRYYVALRHYYNWLTRQRY | 93 |
| 90 | APEKPEEDATPEELQRYYVVLRHYYNWLTRQRY | 94 |
| 91 | APEKPEEDAEPEELQRYYTSLRHYYHWLTRQRY | 95 |
| 92 | APEKPGEDASPEELQRYYISLRHYYNWLTRQRY | 96 |
| 93 | APEKPEEDASPEEIQRYYVQLRHYYNWLTRQRY | 97 |
| 94 | APAKPEADASPEELQRYYVELRHYYNWLTRQRY | 98 |
| 95 | APEKPEEDATPEELQAYYVSLRHYYNWLTRQRY | 99 |
| 96 | APEKPEESATPEELQRYYVSLRHYYNWLTRQRY | 100 |
| 97 | APEKPEEDATPEEIQRYYLSLRHYYNWLTRQRY | 101 |
| 98 | APEKPEADATPEEIQRYYVSLRHYYNWLTRQRY | 102 |
| 99 | APAKPEEDATPEEIQRYYVALRHYYNWLTRQRY | 103 |
| 100 | APEKPEADATPEELQRYYIALRHYYNWLTRQRY | 104 |
| 101 | APAKPEEDATPEELQRYYVALRHYYNWLTRQRY | 105 |
| 102 | APEKPEEDATLEELQRYYVSLRHYYNWLTRQRY | 106 |
| 103 | APEKPEEDASAEELQRYYVALRHYYNWLTRQRY | 107 |
| 104 | APEKPEEDAEPEEAQRYYVSLRHYYNWLTRQRY | 108 |
| 105 | APEKPEEDATQEELQRYYVSLRHYYNWLTRQRY | 109 |
| 106 | APAKPEEDASPEELQRYYVALRHYYNWLTRQRY | 110 |
| 107 | APEKPEEDAEPEETQRYYVSLRHYYNWLTRQRY | 111 |
| 108 | APEKPEADASEEELQRYYVSLRHYYNWLTRQRY | 112 |
| 109 | APEKPEEDLTPEELQRYYVSLRHYYNWLTRQRY | 113 |
| 110 | APEKPEEDATPEELQRYYVELRHYYNWLTRQRY | 114 |
| 111 | APAKPEAAAEPEEIQRYYVSLRHYYNWLTRQRY | 115 |
| 112 | APEKPEEDAEPEEIQRYYVSLRHYYNWLTRQRY | 116 |

TABLE 1-continued

| cf. compound No | Sequence | SEQ ID NO |
|---|---|---|
| 113 | APEKPEEDATPEEIQRYYVSLRHYQNWLTRQRY | 117 |
| 114 | APAKPEEDATPEEIQRYYVSLRHYYNWLTRQRY | 118 |
| 115 | APEKPEEDATPEELQRYQVSLRHYYNWLTRQRY | 119 |
| 116 | APAKPEAAAEPEEIQRYYVALRHYYNWLTRQRY | 120 |
| 117 | APEKPEEDASPEEAQRYYVALRHYYNWLTRQRY | 121 |
| 118 | APEKPPEDAEPEEIQRYYVSLRHYYNWLTRQRY | 122 |
| 119 | APEKPEEDATPEESQRYYVSLRHYYNWLTRQRY | 123 |
| 120 | APAKPEEAATPEEIQRYYVALRHYYNWLTRQRY | 124 |
| 121 | APEKPEADASPEELQRYYVQLRHYYNWLTRQRY | 125 |
| 122 | APEKPEAEASPEELQRYYVSLRHYYNWLTRQRY | 126 |
| 123 | APEKPEEDAAPEELQKYYVSLRHYYNWLTRQRY | 127 |
| 124 | APEKPEAAAEPEEIQRYYVSLRHYYNWLTRQRY | 128 |
| 125 | APEKPEEDASPEELQRYYVELRHYYNWLTRQRY | 129 |
| 126 | APEKPEEDAEPEELQRYYVSLRHYYNWLTRQRY | 130 |
| 127 | APEKPEAAAEPEELQRYYVALRHYYNWLTRQRY | 131 |
| 128 | APEKPEEAATPEELQRYYVSLRHYYNWLTRQRY | 132 |
| 129 | APEKPEEDASAEEIQRYYVSLRHYYNWLTRQRY | 133 |
| 130 | APEKPEEDATPEELQLYYVSLRHYYNWLTRQRY | 134 |
| 131 | APEKPEADAEPEEIQRYYVALRHYYNWLTRQRY | 135 |
| 132 | APEKPEADATPEELQRYYVSLRHYYNWLTRQRY | 136 |
| 133 | APAKPEEDAEPEELQRYYVSLRHYYNWLTRQRY | 137 |
| 134 | APEKPEEDATPEEQQRYYVSLRHYYNWLTRQRY | 138 |
| 135 | APEKPEAAAEPEEIQRYYVALRHYYNWLTRQRY | 139 |
| 136 | APEKPEADATPEELQRYYVALRHYYNWLTRQRY | 140 |
| 137 | APEKPEEDATPEELQRYYVSLRHYYNWLLRQRY | 141 |
| 138 | APEKPEEDAEPEELQEYYVSLRHYYNWLTRQRY | 142 |
| 139 | APEKPEEEASPAELQRYYVSLRHYYNWLTRQRY | 143 |
| 140 | APEKPEADASPEEIQRYYVSLRHYYNWLTRQRY | 144 |
| 141 | APEKPEEDATPEELQSYYVSLRHYYNWLTRQRY | 145 |
| 142 | APEKPEEDALPEEIQRYYVSLRHYYNWLTRQRY | 146 |
| 143 | APEKPEEDSTPEELQRYYVSLRHYYNWLTRQRY | 147 |
| 144 | APEKPEEDQTPEELQRYYVSLRHYYNWLTRQRY | 148 |
| 145 | APAKPEEDASPEELQRYYVSLRHYYNWLTRQRY | 149 |
| 146 | APEKPEEEATPEELQRYYVSLRHYYNWLTRQRY | 150 |
| 147 | APEKPEEDASPEEIQRYYVSLRHYYNWLTRQRY | 151 |
| 148 | APEKPEEDATPEELQRYYVTLRHYYNWLTRQRY | 152 |
| 149 | APAKPEEDASPEESQRYYVSLRHYYNWLTRQRY | 153 |
| 150 | APEKPEEAASPEEIQRYYVSLRHYYNWLTRQRY | 154 |
| 151 | APEKPEEDSSPEELQRYYVALRHYYNWLTRQRY | 155 |
| 152 | APEKPEEDATPEETQRYYVSLRHYYNWLTRQRY | 156 |
| 153 | APEKPEELATPEELQRYYVSLRHYYNWLTRQRY | 157 |
| 154 | APEKPEEAATPEEIQRYYVALRHYYNWLTRQRY | 158 |
| 155 | APEKPEEDATPEELQRYYVSLRHYYNWLSRQRY | 159 |
| 156 | APEKPEEAAEPEEIQRYYVALRHYYNWLTRQRY | 160 |
| 157 | APAKPEEAASPEELQRYYVALRHYYNWLTRQRY | 161 |
| 158 | APEKPPEAASPEEIQRYYVALRHYYNWLTRQRY | 162 |
| 159 | APEKPEADAEPEELQRYYISLRHYYNWLTRQRY | 163 |
| 160 | APAKPEEDASPEELQRYYIALRHYYNWLTRQRY | 164 |
| 161 | APAKPEEAAEPEELQRYYVALRHYYNWLTRQRY | 165 |
| 162 | APEKPEEDATPEEEQRYYVSLRHYYNWLTRQRY | 166 |
| 163 | APEKPEADASPEELQRYYVALRHYYNWLTRQRY | 167 |
| 164 | APEKPEEDATPEEIQRYYQSLRHYYNWLTRQRY | 168 |
| 165 | APAKPPEDAEPEELQRYYVSLRHYYNWLTRQRY | 169 |
| 166 | APAKPEEDASPEELQRYYVELRHYYNWLTRQRY | 170 |
| 167 | APAKPEEAAEPEEIQRYYVALRHYYNWLTRQRY | 171 |
| 168 | APEKPEEDATPEEIQRYYSSLRHYYNWLTRQRY | 172 |
| 169 | APEKPEEDAEPEELQAYYVSLRHYYNWLTRQRY | 173 |
| 170 | APEKPEEDAAPEEIQRYYVSLRHYYNWLTRQRY | 174 |
| 171 | APEKPEADASPEELQRYYVELRHYYNWLTRQRY | 175 |
| 172 | APEKPPEDASPEEIQRYYVSLRHYYNWLTRQRY | 176 |
| 173 | APEKPEEDATPEELQRYYVSLRHYYNWLTRQRY | 177 |
| 174 | APEKPGADASPEKLQRYYVSLRHYYHKLTRQRY | 178 |
| 175 | APAKPEEDAEPEELQRYYIALRHYYNWLTRQRY | 179 |
| 176 | APEKPEEDATPEEIQRYYVSLRHYYNWLTRQRY | 180 |
| 177 | APEKPEEDATPEELQQYYVSLRHYYNWLTRQRY | 181 |
| 178 | APEKPEAAATPEEIQRYYVALRHYYNWLTRQRY | 182 |
| 179 | APEKPEADASPEETQRYYVALRHYYNWLTRQRY | 183 |
| 180 | APEKPEEDATPEELQRYYVSLRHYYNWLTKQRY | 184 |
| 181 | APAKPEADAEPEEIQRYYVALRHYYNWLTRQRY | 185 |
| 182 | APAKPEEDASPEEAQRYYVALRHYYNWLTRQRY | 186 |
| 183 | APEKAEEDASPEEIQRYYVSLRHYYNWLTRQRY | 187 |
| 184 | APEKPEADATPEEIQRYYVALRHYYNWLTRQRY | 188 |
| 185 | APAKPEEDASEEELQRYYVSLRHYYNWLTRQRY | 189 |
| 186 | APEKPEEDAEPEEAQRYYVSLRHYYNWLTRQRY | 190 |
| 187 | APEKPEEDATPEEPQRYYVSLRHYYNWLTRQRY | 191 |
| 188 | APEKPEEDATPEELQRYYVSLRHYYNWLQRQRY | 192 |

TABLE 1-continued

| cf. compound No | Sequence | SEQ ID NO |
|---|---|---|
| 189 | APAKPEEDASPEETQRYYVALRHYYNWLTRQRY | 193 |
| 190 | APAKPEEDATPEELQRYYISLRHYYNWLTRQRY | 194 |
| 191 | APEKPEEDATPEEIQRYYESLRHYYNWLTRQRY | 195 |
| 192 | APEKPEAPASPEELQRYYVSLRHYYNWLTRQRY | 196 |
| 193 | APEKPEEEASPEEIQRYYVSLRHYYNWLTRQRY | 197 |
| 194 | APAKPEEDAEPEEIQRYYVALRHYYNWLTRQRY | 198 |
| 195 | APAKPEEDASPEEIQRYYISLRHYYNWLTRQRY | 199 |
| 196 | APEKPEADASPEELQRYYVSLRHYYNWLTRQRY | 200 |

TABLE 1-continued

| cf. compound No | Sequence | SEQ ID NO |
|---|---|---|
| 197 | APEKPEEDASPEEIQRYYVALRHYYNWLTRQRY | 201 |
| 198 | APAKPEADAEPEEIQRYYVSLRHYYNWLTRQRY | 202 |
| 199 | APAKPEEEASPEELQRYYVSLRHYYNWLTRQRY | 203 |

and wherein a half-life extending group is attached to the epsilon amino group of the lysine at position 7 or of a lysine at positions 6, 10, 11, 14, 17, 21 or 22, or to the carboxylic acid group of the side chain of an aspartate or a glutamate at position 14.

In an embodiment of the present invention, the PYY analogue is a compound having the formula:

$R^1$—Z—$R^2$,

Wherein $R^1$ and $R^2$ are as defined above;

Z is an amino acid sequence of selected from Table 1; and wherein a half-life extending group is attached to the epsilon amino group of the lysine at position 7 and consists of a lipophilic substituent X and a linker U, wherein the linker U is attached to the amino acid side chain and X is attached to U, and the linker U consists of one, two or three sub-moieties (U1, U2, U3), wherein at least one sub-moiety is Ahx.

In some embodiments, the lipophilic substituent X is selected from the group consisting of 15-carboxy-pentadecanoyl, 17-carboxy-heptadecanoyl (C18DA) and 19-carboxynonadecanoyl.

In some embodiments the linker U consists of one, two or three sub-moieties ($U^1$, $U^2$, $U^3$) independently selected from the group consisting of Gly, Glu, γ-Glu, ε-Lys, Ser, Ahx and OEG, or independently selected from the group consisting of γ-Glu, Ahx and OEG.

In some embodiments the linker U comprises one or more Ahx as (sub-)moiety.

In certain embodiments, the linker U is selected from the group consisting of γ-Glu, γ-Gluγ-Glu, γ-Glu-OEG, OEG-γ-Glu, γ-Glu-Ahx, Ahx-γ-Glu, OEG-OEG, Ahx-Ahx, γ-Glu-γ-Glu-OEG, OEG-γ-Glu-γ-Glu, γ-Glu-γ-Glu-Ahx, Ahx-γ-Glu-γ-Glu, γ-Glu-OEG-OEG, OEG-OEG-γ-Glu, γ-Glu-Ahx-Ahx and Ahx-Ahx-γ-Glu.

In certain embodiments, the linker U is selected from the group consisting of γ-Glu-Ahx, Ahx-γ-Glu, Ahx-Ahx, γ-Glu-γ-Glu-Ahx, Ahx-γ-Glu-γ-Glu, γ-Glu-Ahx-Ahx and Ahx-Ahxγ-Glu.

In specific embodiments, the half-life extending group is C18DA-γ-Glu-Ahx-, i.e.

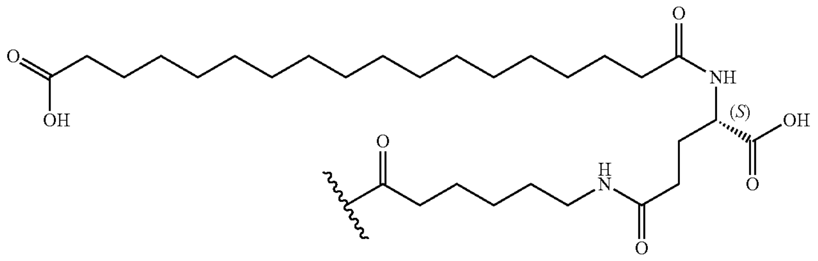

In some embodiments of the present invention, the PYY analogue is a compound selected from the group consisting of compound 1 to compound 199 as defined below.

In some embodiments, the PYY analogue has a maximum of 15 amino acid modifications as compared to hPYY(3-36).

In some embodiments, the PYY analogue has a maximum of 14 amino acid modifications as compared to hPYY(3-36).

In some embodiments, the PYY analogue has a maximum of 13 amino acid modifications as compared to hPYY(3-36).

In some embodiments, the PYY analogue has a maximum of 12 amino acid modifications as compared to hPYY(3-36).

In some embodiments, the PYY analogue has a maximum of 11 amino acid modifications as compared to hPYY(3-36).

In some embodiments, the PYY analogue has between 7 and 15 (i.e. 7, 8, 9, 10, 11, 12, 13, 14 or 15) amino acid modifications as compared to hPYY(3-36).

In some embodiments, the PYY analogue has between 8 and 14 (i.e. 8, 9, 10, 11, 12, 13 or 14) amino acid modifications as compared to hPYY(3-36).

In some embodiments, the PYY analogue has between 5 and 13 (i.e. 5, 6, 7, 8, 9, 10, 11, 12 or 13) amino acid modifications as compared to hPYY(3-36).

In some embodiments, the PYY analogue has between 7 and 13 (i.e. 7, 8, 9, 10, 11, 12 or 13) amino acid modifications as compared to hPYY(3-36).

In some embodiments, the PYY analogue has between 8 and 13 (i.e. 8, 9, 10, 11, 12 or 13) amino acid modifications as compared to hPYY(3-36).

In some embodiments, the PYY analogue has between 9 and 13 (i.e. 9, 10, 11, 12 or 13) amino acid modifications as compared to hPYY(3-36).

In some embodiments, the PYY analogue has between 10 and 13 (i.e. 10, 11, 12 or 13) amino acid modifications as compared to hPYY(3-36).

In some embodiments, the PYY analogue has between 8 and 12 (i.e. 8, 9, 10, 11 or 12) amino acid modifications as compared to hPYY(3-36).

In some embodiments, the PYY analogue has between 9 and 12 (i.e. 9, 10, 11 or 12) amino acid modifications as compared to hPYY(3-36).

In some embodiments, the PYY analogue has between 10 and 12 (i.e. 10, 11 or 12) amino acid modifications as compared to hPYY(3-36).

In some embodiments, the PYY analogue has between 11 and 12 (i.e. 11 or 12) amino acid modifications as compared to hPYY(3-36).

In some embodiments, the PYY analogue has between 9 and 11 (i.e. 9, 10 or 11) amino acid modifications as compared to hPYY(3-36).

In some embodiments, the PYY analogue or compound of the above-mentioned embodiments is in the form of a salt, preferably in the form of a pharmaceutically acceptable salt.

The PYY analogues of the invention are able to bind to the human NPY2 receptor (hNPY2-R).

Binding to biological receptors can be measured by appropriate assays known in the art. For instance, binding of PYY analogues to the NPY2 receptor can be evaluated by radio-ligand binding competition assays as described in Example 1, below.

In some embodiments of compounds of the present invention, the binding affinity (Ki) towards hNPY2 receptor is below 100 nM (e.g. 0.01 to 100 nM).

In some embodiments of compounds of the present invention, the binding affinity (Ki) towards hNPY2 receptor is below 50 nM (e.g. 0.01 to 50 nM).

In some embodiments of compounds of the present invention, the binding affinity (Ki) towards hNPY2 receptor is below 10 nM (e.g. 0.01 to 10 nM).

In some embodiments of compounds of the present invention, the binding affinity (Ki) towards hNPY2 receptor is below 5 nM (e.g. 0.01 to 5 nM).

In some embodiments of compounds of the present invention, the binding affinity (Ki) towards hNPY2 receptor is below 2 nM (e.g. 0.01 to 2 nM).

The PYY analogues of the invention activate the human NPY2 receptor, i.e. they are NPY2 agonists.

In general, it is preferred to use a biological assay, which measures intracellular signalling caused by binding of the compound to the relevant receptor. Activation of the NPY2 receptor by compounds of the invention (which behave as agonists of the receptor) reduces cAMP concentrations effecting intracellular signalling pathways. Thus, reduction of cAMP or any other suitable parameter in cells expressing the receptor can be used to monitor agonist activity towards the receptor. The skilled person will be aware of suitable assay formats, and examples are provided below.

$EC_{50}$ values may be used as a numerical measure of agonist potency at a given receptor. An $EC_{50}$ value is a measure of the concentration of a compound required to achieve half of that compound's maximal activity in a particular assay, e.g. in the assay as described in Example 2, below.

In some embodiments of compounds of the present invention, the $EC_{50}$ towards hNPY2 receptor is below 100 nM (e.g. 0.001 to 100 nM).

In some embodiments of compounds of the present invention, the $EC_{50}$ towards hNPY2 receptor is below 50 nM (e.g. 0.001 to 50 nM).

In some embodiments of compounds of the present invention, the $EC_{50}$ towards hNPY2 receptor is below 10 nM (e.g. 0.001 to 10 nM).

In some embodiments of compounds of the present invention, the $EC_{50}$ towards hNPY2 receptor is below 5 nM (e.g. 0.001 to 5 nM).

In some embodiments of compounds of the present invention, the $EC_{50}$ towards hNPY2 receptor is below 2 nM (e.g. 0.001 to 2 nM).

As mentioned above the PYY analogues or compounds of the present invention are generally soluble around pH 7 and 6. There are several techniques known to the skilled person in the art how to determine solubility. One such experiment is described below under Example 3. If specific solubility in mg/ml is provided herein, it is referred to the solubility determination as in Example 3.

In some embodiments, the solubility of the PYY analogues or compounds of the invention is greater than 1.0 mg/ml around pH 6 (e.g. at pH 6.1±0.2).

In some embodiments, the solubility of the PYY analogues or compounds of the invention is greater than 3.0 mg/ml around pH 6 (e.g. at pH 6.1±0.2).

In some embodiments, the solubility of the PYY analogues or compounds of the invention is greater than 5.0 mg/ml around pH 6 (e.g. at pH 6.1±0.2).

In some embodiments, the solubility of the PYY analogues or compounds of the invention is equal to or greater than 7.0 mg/ml around pH 6 (e.g. at pH 6.1±0.2).

In some embodiments, the solubility of the PYY analogues or compounds of the invention is equal to or greater than 8.0 mg/ml around pH 6 (e.g. at pH 6.1±0.2).

In some embodiments, the solubility of the PYY analogues or compounds of the invention is greater than 1.0 mg/ml around pH 7 (e.g. at pH 6.8±0.2).

In some embodiments, the solubility of the PYY analogues or compounds of the invention is greater than 5.0 mg/ml around pH 7 (e.g. at pH 6.8±0.2).

In some embodiments, the solubility of the PYY analogues or compounds of the invention is greater than 7.0 mg/ml around pH 7 (e.g. at pH 6.8±0.2).

In some embodiments, the solubility of the PYY analogues or compounds of the invention is equal to or greater than 8.0 mg/ml around pH 7 (e.g. at pH 6.8±0.2).

In some embodiments, the solubility of the PYY analogues or compounds of the invention is greater than 1.0 mg/ml around pH 6 (e.g. at pH 6.1±0.2) and around pH 7 (e.g. at pH 6.8±0.2).

In some embodiments, the solubility of the PYY analogues or compounds of the invention is greater than 3.0 mg/ml around pH 6 (e.g. at pH 6.1±0.2) and around pH 7 (e.g. at pH 6.8±0.2).

In some embodiments, the solubility of the PYY analogues or compounds of the invention is greater than 5.0 mg/ml around pH 6 (e.g. at pH 6.1±0.2) and around pH 7 (e.g. at pH 6.8±0.2).

In some embodiments, the solubility of the PYY analogues or compounds of the invention is greater than 6.0 mg/ml around pH 6 (e.g. at pH 6.1±0.2) and around pH 7 (e.g. at pH 6.8±0.2).

In some embodiments, the solubility of the PYY analogues or compounds of the invention is greater than 7.0 mg/ml around pH 6 (e.g. at pH 6.1±0.2) and around pH 7 (e.g. at pH 6.8±0.2).

In some embodiments the PYY analogues or compounds of the invention have favourable pharmacokinetic properties. In this regard, in some embodiments of the invention, the in-vivo half-life of the PYY analogues or compounds is at least 3 hours in the mouse (NMRI mice, see measurement described in Example 5). In some embodiments, the in-vivo half-life is at least 5 hours in the mouse. In some embodiments, the in-vivo half-life is at least 7 hours in the mouse. In some embodiments, the in-vivo half-life is at least 10 hours in the mouse.

The invention further provides a composition comprising a PYY analogue as described above. The composition may be a pharmaceutical composition, and may comprise a pharmaceutically acceptable carrier, excipient or vehicle.

The invention further provides a method for the synthesis of a PYY analogue as described above. The method may comprise the steps of synthesising the peptide by solid-phase or liquid-phase methodology, and optionally isolating and/or purifying the final product.

Method of Treatment

The present invention is directed to PYY analogues or a compound according to the above-mentioned embodiments, which are useful in the prevention and/or treatment of a disease and/or condition associated with or modulated by NPY2 receptor activity, including but not limited to the treatment and/or prevention of obesity and various obesity-related conditions, diseases, or co-morbidities, such as type 2 diabetes and NASH (non-alcoholic steatohepatitis).

The compounds described herein find use, inter alia, in preventing weight gain or promoting weight loss. By "preventing" is meant inhibiting or reducing when compared to the absence of treatment, and is not necessarily meant to imply complete cessation of weight gain. The peptides may cause a decrease in food intake and/or increased energy expenditure, and may have a beneficial effect on glucose control and/or on circulating cholesterol levels, being capable of lowering circulating LDL levels and increasing HDL/LDL ratio. Thus, the compounds of the invention can be used for direct or indirect therapy of any condition caused or characterised by excess body weight, such as the treatment and/or prevention of obesity, morbid obesity, obesity linked inflammation, obesity linked gallbladder disease, and obesity related sleep apnea. They may also be used for the prevention of conditions or treatment of obesity associated co-comorbidities caused or characterised by inadequate glucose control or dyslipidaemia (e.g. elevated LDL levels or reduced HDL/LDL ratio), Type 2 diabetes, metabolic syndrome, hypertension, atherogenic dyslipidemia, and cardiovascular diseases such as atherosclerosis, coronary heart disease, peripheral artery disease, stroke or microvascular disease, and cancer. Their effects in these diseases may be as a result of or associated with their effect on body weight, or may be independent thereof.

As mentioned above the PYY analogues or compounds according to the above mentioned embodiments are useful in the reduction of food intake, promotion of weight loss, and inhibition or reduction of weight gain. As a result, they may be used for treatment of a variety of conditions, diseases, or disorders in a subject, including, but not limited to, obesity and various obesity-related conditions, diseases, or co-morbidities, such as type 2 diabetes, hypertension, dyslipidemia, sleep apnea, cardiovascular disease, hepatic steatosis, non-alcoholic fatty liver disease (NAFLD), non-alcoholic steatohepatitis (NASH) and cancer. The subject may be affected by obesity accompanied by at least one weight-related comorbid condition, such as type 2 diabetes, hypertension, dyslipidemia, sleep apnea, cardiovascular disease, hepatic steatosis, NAFLD and NASH. It will be understood that the PYY analogues may thus be administered to subjects affected by conditions or diseases characterised by inadequate control of appetite or otherwise over-feeding, such as binge-eating disorder and Prader-Willi syndrome. It will be clear that the analogues can be used for treatment of combinations of the conditions or diseases described.

Thus, the invention provides a PYY analogue for use in a method of medical treatment, e.g. for treating, inhibiting or reducing weight gain, promoting weight loss and/or reducing excess body weight. Treatment may be achieved, for example, by control of appetite, feeding, food intake, caloric intake and/or energy expenditure.

The invention also provides a PYY analogue of the invention for use in a method of treating obesity as well as associated diseases, disorders and health conditions, including, but not limited to, morbid obesity, obesity prior to surgery, obesity-linked inflammation, obesity-linked gallbladder disease and obesity related sleep apnea and respiratory problems, degeneration of cartilage, osteoarthritis, and reproductive health complications of obesity or overweight such as infertility. The subject may be affected by obesity accompanied by at least one weight-related comorbidity, such as type 2 diabetes, hypertension, dyslipidemia, sleep apnea, cardiovascular disease, cancer, hepatic steatosis, NAFLD and NASH.

The invention also provides a PYY analogue of the invention for use in a method of prevention or treatment of conditions or diseases mentioned above.

Accordingly, the present invention relates to a PYY analogue or a compound according to the above-mentioned embodiments for use as a medicament.

Furthermore, the present invention relates to the use of a PYY analogue or a compound according to the above-mentioned embodiments for the treatment and/or prevention of a disease and/or condition associated with or modulated by NPY2 receptor activation. Furthermore, the present invention relates to the use of a PYY analogue or a compound according to the above mentioned embodiments for the treatment and/or prevention of obesity and various obesity-related conditions, diseases, or co-morbidities, such as type 2 diabetes and NASH (non-alcoholic steatohepatitis) and others as mentioned above.

In a further aspect the present invention relates to the use of a PYY analogue or a compound according to the above mentioned embodiments for the preparation of a medicament for the treatment and/or prevention of above-mentioned diseases and conditions.

In a further aspect the present invention relates to methods for the treatment or prevention of above mentioned diseases and conditions, which method comprises the administration of an effective amount of a PYY analogue or a compound according to the above-mentioned embodiments to a human being.

The dose range of the compounds of general formula 1 applicable per week is usually from 0.01 to 100 mg for humans (subcutaneous administration).

The actual pharmaceutically effective amount or therapeutic dosage will usually depend on factors known by those skilled in the art such as age and weight of the patient, route of administration and severity of disease. In any case, the compounds will be administered at dosages and in a manner, which allows a pharmaceutically effective amount to be delivered based upon patient's unique condition.

Combination Therapy

A PYY analogue of the invention may be administered as part of a combination therapy together with another active agent for the treatment of the disease or disorder in question, e.g. an anti-obesity agent, an anti-diabetic agent, an agent for treatment of metabolic syndrome, an anti-dyslipidemia agent, an anti-hypertensive agent, a proton pump inhibitor, or an anti-inflammatory agent. In such cases, the two active agents may be given together or separately, e.g. as constituents in the same pharmaceutical composition or formulation, or as separate formulations.

Thus, a peptide of the invention may be used in combination with an anti-obesity agent of known type. The anti-obesity agent may be a GIP or GLP-1 receptor agonist (including GLP-1 or a GLP-1 analogue, exendin-4 or an exendin-4 analogue, any other GLP-1 receptor agonist including Liraglutide (Saxenda™), Semaglutide, Dulaglutide, Albiglutide, MK-8521, or a glucagon-GLP-1 dual agonist (e.g. HM-12525, SAR-425899, MEDI-0382, NN-9277 or as described in WO2008/101017, WO2008/152403, WO2010/070252, WO2010/070253, WO2010/070255, WO2010/070251, WO2011/006497, WO2011/160630, WO2011/160633, WO2013/092703, WO2014/041195, WO2015/055801, WO2015/055802, WO2016/166289), oxyntomodulin or an oxyntomodulin analog (e.g. TT-401) or a GLP-1/GIP dual agonist (e.g. Tirzepatide or as described in WO2013/164483), or a GLP-1/GIP/glucagon triple agonists (e.g. NN-9423 or as described in WO2015/067716, WO2016/198624, WO2017/116204, WO2017/116205, WO2018/100134, WO2018/100135).

The anti-obesity agent may be amylin or an amylin analogue, e.g. pramlintide, NN-9838, or an amylin (or calcitonin) analogue disclosed in WO2012/168430, WO2012/168431, WO2012/168432, WO2015/040182, WO2015/071229, WO2016/146739, WO2018/046719, or WO2018/172390.

Alternatively, the anti-obesity agent may be Orlistat™, Sibutramine™, phentermine, a melanin concentrating hormone receptor 1 antagonist, CCK, leptin analogue, a GOAT inhibitor, a ghrelin-receptor antagonist, a further neuropeptide Y (NPY) analogue, a NPY4 receptor agonist, a NPY5 receptor antagonist, a cannabinoid receptor 1 antagonist, a beta-3 agonist, a lipase inhibitor, Human proIslet Peptide (HIP), a melanocortin receptor 4 agonist, as well as analogues thereof.

Moreover, a peptide of the invention may have some benefit if administered in combination with an anti-diabetic agent of known type, including, but not limited to, metformin, a sulfonylurea, a glinide, a DPP-IV inhibitor, a glitazone, a GLP-1 receptor agonist (including GLP-1 or a GLP-1 analogue, an exendin-4 or an exendin-4 analogue, any other GLP-1 receptor agonist including Liraglutide (Victoza™), Semaglutide, Dulaglutide, Albiglutide, MK-8521, or a glucagon-GLP-1 dual agonist (e.g. HM-12525, SAR-425899, MEDI-0382, NN-9277 or as described in WO2008/101017, WO2008/152403, WO2010/070252, WO2010/070253, WO2010/070255, WO2010/070251, WO2011/006497, WO2011/160630, WO2011/160633, WO2013/092703, WO2014/041195, WO2015/055801, WO2015/055802, WO2016/166289), oxyntomodulin, or an oxyntomodulin analog (e.g. TT-401), or a SGLT2 inhibitor (i.e. an inhibitor of sodium-glucose transport, e.g. a gliflozin such as empagliflozin, canagliflozin, dapagliflozin or ipragliflozin), a GPR40 agonist (FFAR1/FFA1 agonist, e.g. fasiglifam), or an insulin or an insulin analogue. Examples of appropriate insulin analogues include, but are not limited to, Lantus™, Novorapid™, Humalog™, Novomix™, Actraphane™ HM, Levemir™ Degludec™ and Apidra™. Other relevant anti-diabetic agents in this connection include GLP-1 receptor agonists, such as exenatide (Byetta™ and Bydureon™ exendin-4) and Byetta LAR™, and lixisenatide (Lyxumia™).

According to more specific embodiments, the PYY analogue of the present invention is administered as part of a combination therapy together with

- a GLP-1 receptor agonist selected from the group consisting of Liraglutide, Semaglutide, Dulaglutide and Albiglutide or a glucagon-GLP-1 dual agonist described in WO2011/006497, WO2014/041195, WO2015/055801, WO2015/055802, WO2016/166289 or
- an amylin receptor agonist selected from the group consisting of pramlintide or an amylin analogue disclosed in WO2012/168430, WO2012/168431, WO2012/168432, WO2015/040182, WO2016/146739, or WO2018/046719.

A peptide of the invention may further be used in combination with medications targeting cardiovascular diseases treating hypertension, dyslipidemia, inflammation and platelet function. The medication treating hypertension can be selected from the group including, but not limited to, an angiotensin-converting enzyme inhibitor, an angiotensin II receptor blocker, a diuretic, a beta-blocker or a calcium channel blocker.

A peptide of the invention may still further be used in combination with an anti-dyslipidemia agent of known type, including, but not limited to, a statin, a fibrate, a niacin, a PSCK9 (Proprotein convertase subtilisin/kexin type 9) inhibitor, or a cholesterol absorption inhibitor.

A peptide of the invention may also be used in combination with a proton pump inhibitor (i.e. a pharmaceutical agent possessing pharmacological activity as an inhibitor of $H^+/K^+$-ATPase) of known type, including, but not limited to, an agent of the benzimidazole derivative type or of the imidazopyridine derivative type, such as Omeprazole™, Lansoprazole™, Dexlansoprazole™, Esomeprazole™, Pantoprazole™, Rabeprazole™, Zolpidem™, Alpidem™, Saripidem™ or Necopidem™.

In addition, with regard to anti-inflammatory treatment, a peptide of the invention may be beneficial if administered in combination with an anti-inflammatory agent of known type, including, but not limited to:

- steroids and corticosteroids, such as beclomethasone, methylprednisolone, betamethasone, prednisone, dexamethasone, and hydrocortisone;
- non-steroidal anti-inflammatory agents (NSAIDs), such as propionic acid derivatives (e.g. alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen); acetic acid derivatives (e.g. indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac); fenamic acid derivatives (e.g. flufenamic acid, meclofenamic acid, mefenamic acid, niflumic acid and tolfenamic acid); biphenylcarboxylic acid derivatives (e.g. diflunisal and flufenisal); oxicams (e.g. isoxicam, piroxicam, sudoxicam and tenoxicam); salicylates (e.g. acetylsalicylic acid and sulfasalazine); and pyrazolones (e.g. apazone, bezpiperylon, feprazone, mofebutazone, oxyphenbutazone and phenylbutazone);
- COX II inhibitors, such as rofecoxib and celecoxib; preparations of interferon beta (e.g. interferon beta-1a or interferon beta-1b);
- and certain other compounds, such as 5-aminosalicylic acid and prodrugs and pharmaceutically acceptable salts thereof.

Preparation

General Procedure for Solid Phase Synthesis of Peptides

All peptides were synthesized by standard Fmoc-based solid phase peptide chemistry on a Tentagel S RAM resin (loading 0.23-0.25 mmol/g, bead size 90 μm) supplied by Iris Biotech GmbH or Rapp Polymere GmbH.

The following protected amino acids were used: Fmoc-Ala-OH, Fmoc-Arg(Pbf)-OH, Fmoc-Asn(Trt)-OH, Fmoc-Asp(tBu)-OH, Fmoc-Gln(Trt)-OH, Fmoc-Glu(tBu)-OH, Fmoc-Glu-OtBu, Fmoc-Gly-OH, Fmoc-His(Trt)-OH, Fmoc-Ile-OH, Fmoc-Leu-OH, Fmoc-Lys(Boc)-OH, Fmoc-Lys(Dde)-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, Fmoc-Val-OH. The L-form of the amino acid building blocks was utilized if not specified otherwise. The modular half-life extending group was built up by solid-phase peptide synthesis (SPPS) using protected building blocks such as, but not limited to, 18-(tert-butoxy)-18-oxooctadecanoic acid (C18DA(tBu)), 2-[2-[2-[[2-[2-[2-(9H-fluoren-9-ylmethoxycarbonylamino)ethoxy]ethoxy]acetyl]amino]ethoxy]ethoxy]acetic acid (Fmoc-OEG-OEG-OH), 2-[2-[2-(9H-fluoren-9-ylmethoxycarbonylamino)ethoxy]ethoxy] acetic acid (Fmoc-OEG-OH), 6-{[(9H-fluoren-9-ylmethoxy)carbonyl]amino}hexanoic acid (Fmoc-Ahx) and Fmoc-Glu-OtBu.

The amino acids, Fmoc-Glu-OtBu, Oxyma and DIC, were purchased from standard suppliers, e.g. Bachem, Novabiochem, ABCR, Iris Biotech GmbH, Sigma-Aldrich. 18-(Tert-butoxy)-18-oxooctadecanoic acid (C18DA(tBu)) was supplied by Cool Pharm Ltd. or AstraTech, 2-[2-[2-[[2-[2-[2-(9H-Fluoren-9-ylmethoxycarbonylamino)ethoxy]ethoxy]acetyl]amino]ethoxy]ethoxy]acetic acid (Fmoc-OEG-OEG-OH) was supplied by ABCR GmbH & CO. KG or Iris Biotech GmbH, 2-[2-[2-(9H-fluoren-9-ylmethoxycarbonylamino)ethoxy]ethoxy] acetic acid (Fmoc-OEG-OH) was supplied by Combi Blocks Inc., Iris Biotech GmbH or Hangzhou APIChem Technology Co., Ltd. 6 6-{[(9H-fluoren-9-ylmethoxy)carbonyl]amino}hexanoic acid (Fmoc-Ahx) was purchased by Activate Scientific GmbH, 3-Methylbutanoic acid was supplied by Sigma-Aldrich GmbH.

Assembly of peptides started from the C-terminus by stepwise chain elongation towards the N-terminus according to the respective sequences until the N-terminal capping group was reached. Deprotection of the side chain of the branching amino acid, e.g. Lys(Dde), was followed by assembly of the half-life extending group.

The PYY analogues were obtained as TFA salts from the cleavage/deprotection or from the HPLC purification. The trifluoroacetate can be exchanged by common procedures, such as resin-ion exchange procedures, e.g. as disclosed in Roux, St. et al. *J. Pept. Sci.* 2008; 14: 354-359.

Synthesis Method 1 (S01)

Peptides were synthesized by microwave-assisted solid-phase peptide synthesis (SPPS) on a CEM Liberty Blue Peptide Synthesizer at 0.25 mmol scale on Tentagel S RAM resin using the Fmoc strategy.

Standard coupling of amino acids was performed with 4 eq of suitably protected amino acid in DMF (0.2 mol/l, 5 ml) or 4 eq Fmoc-Ahx (0.2 mol/l)/Oxyma (0.2 mol/1) in DMF (5 ml), 4 eq of Oxyma in DMF (1 mol/l, 1 ml) and 8 eq DIC in DMF (1 mol/l, 2 ml) at 90° C. for 4 min. Fmoc-Arg(Pbf)-OH was coupled 2 times at 90° C. for 4 min, Fmoc-His(Trt)-OH was coupled 2 times at 50° C. for 12 min and Fmoc-Glu-OtBu was coupled 4 times at 50° C. for 12 min. Fmoc-OEG-OH, Fmoc-OEG-OEG-OH, Fmoc-Ahx and C18DA(tBu) were coupled 2 times for 4 min at 90° C. Capping of the N-terminus was achieved by coupling 3-methylbutanoic acid 3 times at 90° C. for 4 min.

$N^{\alpha}$ Fmoc deprotection was performed with 20% piperidine/DMF (10 ml) for 1 min at 90° C. Deprotection of the Lys(Dde)-group was carried out 2 times with 5% hydrazine hydrate in DMF (10 ml) for 3 min at 90° C.

Raw products were washed on resin with DCM and dried prior to cleavage. Cleavage from resin and deprotection was performed with a mixture of 95% TFA/water (10 ml) and triisopropylsilane (250 μl) for 40 min at 42° C. Crude peptides were precipitated with cold tertbutyl-methyl ether, dissolved in 50% acetonitrile/water and purified by preparative HPLC (P01).

Purification Method 1 (P01)

Crude peptides were purified by reversed phase chromatography using an Agilent preparative HPLC-MS System with preparative pumps G1361A, a diode array detector G1315B, a mass-spectrometer G1956B and a fraction collector CTC PAL IFC. A Waters XSelect CSH Prep C18 column (130 Å, 5 μm, OBD, 30 mm×150 mm) served as stationary phase. The mobile phase was run with a gradient of buffer A (0.1% TFA in $H_2O$) and buffer B (0.1% TFA in ACN, gradient: 20-42% over 44 min) at a flow rate of 50 ml/min at 40° C. The relevant fractions were pooled and lyophilized. The final product was characterized by analytical HPLC-MS (A01).

Purification Method 2 (P02)

Crude peptides were purified by reversed phase HPLC using a Gilson preparative HPLC System with XSelect CSH Phenyl-Hexyl column (Waters 130 Å, 5 μm, 30 mm×150 mm), preparative pumps (Gilson AP-Mod-250 and Gilson 305), UV/VIS detector (Ecom UV10 DAD 800) and a Gilson fraction collector (GX281). The mobile phase was run with a gradient of buffer A (0.1% TFA in $H_2O$) and buffer B (0.1% TFA in ACN, gradient: 22-35% B over 66 min) at a flow rate of 50 ml/min at 40° C. Relevant fractions were analysed, pooled and lyophilized. The final product was characterized by analytical UPLC-MS (A01).

Analytical Method 1 (A01)

Peptide purity and mass were determined by analytical HPLC-MS on a Kinetex C8 column (Phenomenex, 100 Å, 2.6 μm, 4.6 mm×150 mm) using a Waters Acquity HPLC System equipped with 3100 Mass Detector. Analysis was performed by gradient elution with buffer A (0.3% TFA in $H_2O$) and buffer B (0.24% TFA in ACN) at a temperature of 40° C. Details of the gradient and flow rates are summarized in the table below. Retention times and masses were recorded.

| Method Name: | A01 | Gradient/ Solvent Time [min] | % Sol [Water 0.3% TFA (v/v)] | % Sol [ACN 0.24% TFA (v/v)] | Flow [ml/min] | Temp [° C.] |
|---|---|---|---|---|---|---|
| Device description: | Waters Acquity with 3100 MS | 0.0 | 65.0 | 35.0 | 0.5 | 40.0 |
| Column. | Kinetex C8_4.6 × 150 mm_2.6 μm | 15.0 | 45.0 | 55.0 | 0.5 | 40.0 |

-continued

| Method Name: | A01 | Gradient/ Solvent Time [min] | % Sol [Water 0.3% TFA (v/v)] | % Sol [ACN 0.24% TFA (v/v)] | Flow [ml/min] | Temp [° C.] |
|---|---|---|---|---|---|---|
| Column producer: | Phenomenex | 16.0 | 10.0 | 90.0 | 1.0 | 40.0 |
| | | 17.01 | 65.0 | 35.0 | 1.0 | 40.0 |
| | | 18.0 | 65.0 | 35.0 | 1.0 | 40.0 |

List of Abbreviations

ACN: acetonitrile
Ahx: 6-aminohexanoic acid
Boc: tert-butyloxycarbonyl
C18DA(tBu): 18-(tert-butoxy)-18-oxooctadecanoic acid
DPBS: Dulbecco's phosphate-buffered saline
DCM: dichloromethane
DIC: diisopropylcarbodiimide
DIPEA: diisopropylethylamine
Dde: (4,4-dimethyl-2,6-dioxocyclohex-1-ylidene)ethyl
DMF: N,N-dimethylformamid
DODT: 3,6-dioxa-1,8-octanedithiol
Fmoc: 9H-fluoren-9-ylmethoxycarbonyl
Fmoc-Ahx: 6-{[(9H-fluoren-9-ylmethoxy)carbonyl]amino}hexanoic acid
Fmoc-OEG-OH: 2-[2-[2-(9H-fluoren-9-ylmethoxycarbonylamino)ethoxy]ethoxy] acetic acid
Fmoc-OEG-OEG-OH: 2-[2-[2-[[2-[2-[2-(9H-fluoren-9-ylmethoxycarbonylamino)ethoxy]ethoxy]acetyl]amino]ethoxy]ethoxy]acetic acid
HTRF: homogeneous time resolved fluorescence
IBMX: 3-isobutyl-1-methylxanthine
iVal: 3-methylbutanoyl (isovalerianoyl)
MRT: mean residence time
NMP: 1-methyl-pyrrolidine-2-one
Oxyma: 2-cyano-2-(hydroxyimino)acetic acid ethyl ester
OEG: 2-[2-(2-aminoethoxy)ethoxy]acetic acid
Pbf: 2,2,4,6,7-pentamethyldihydrobenzofuran-5-sulfonyl
Rt: retention time
RT: room temperature
SPPS: solid-phase peptide synthesis
tBu: tert-butyl
Trt: trityl
TES: triethylsilane
TFA: trifluoroacetic acid The following compounds were synthesised. All compounds were obtained as TFA salts:

Compound 1

N{alpha-4}-(3-methylbutanoyl)-N{epsilon-7}-(6-[(4S)-4-carboxy-4-(17-carboxyheptadecanamido) butanamido]hexanoyl)[4A,7K,9E,10A,13E,18Q,22I,23A,28Y,30W,31L]-hPYY(4-36)

iVal-APEK(C18DA-gGlu-Ahx)PEADAEPEELQRYYIALRHYYNWLTRQRY-NH2 (SEQ ID NO: 5)

MW (calculated): 4792.5 Da

Synthesis and purification methods: S01; P01

LCMS: 010_CA07; Rt: 12.30 min; m/3: 1598.0 m/4: m/5:

Compound 2

N{alpha-4}-(3-methylbutanoyl)-N{epsilon-7}-(6-[(4S)-4-carboxy-4-(17-carboxyheptadecanamido) butanamido]hexanoyl)[4A,7K,9E,18Q,22I,23A,28Y,30W,31L]-hPYY(4-36)

iVal-APEK(C18DA-gGlu-Ahx)PEEDASPEELQRYYIALRHYYNWLTRQRY-NH2 (SEQ ID NO: 6)

MW (calculated): 4808.5 Da

Synthesis and purification methods: S01; P01

LCMS: 010_CA07; Rt: 13.07 min; m/3: 1603.8 m/4: m/5:

Compound 3

N{alpha-4}-(3-methylbutanoyl)-N{epsilon-7}-(6-[(4S)-4-carboxy-4-(17-carboxyheptadecanamido) butanamido]hexanoyl)[4A,6A,7K,9E,10A,13E,18Q,22V,23A,28Y,30W,31L]-hPYY(4-36)

iVal-APAK(C18DA-gGlu-Ahx)PEADAEPEELQRYYVALRHYYNWLTRQRY-NH2 (SEQ ID NO: 7)

MW (calculated): 4720.4 Da

Synthesis and purification methods: S01; P02

LCMS: 010_CA07; Rt: 11.00 min; m/3: m/4: 1180.9 m/5:

Compound 4

N{alpha-4}-(3-methylbutanoyl)-N{epsilon-7}-(6-[(4S)-4-carboxy-4-(17-carboxyheptadecanamido) butanamido]hexanoyl)[4A,7K,9E,11A,13E,18Q,22V,28Y,30W,31L]-hPYY(4-36)

iVal-APEK(C18DA-gGlu-Ahx)PEEAAEPEELQRYYVSLRHYYNWLTRQRY-NH2 (SEQ ID NO: 8)

MW (calculated): 4808.5 Da

Synthesis and purification methods: S01; P01

LCMS: 010_CA07; Rt: 12.10 min; m/3: 1604.1 m/4: m/5:

Compound 5

N{alpha-4}-(3-methylbutanoyl)-N{epsilon-7}-(6-[(4S)-4-carboxy-4-(17-carboxyheptadecanamido) butanamido]hexanoyl)[4A,6A,7K,9E,18Q,20Q,22V,28Y,30W,31L]-hPYY(4-36)

iVal-APAK(C18DA-gGlu-Ahx)PEEDASPEELQRQYVSLRHYYNWLTRQRY-NH2 (SEQ ID NO: 9)

MW (calculated): 4717.4 Da

Synthesis and purification methods: S01; P02

LCMS: 010_CA07; Rt: 9.77 min; m/3: 1572.4 m/4: 1180.2 m/5:

Compound 6

N{alpha-4}-(3-methylbutanoyl)-N{epsilon-7}-(6-[(4S)-4-carboxy-4-(17-carboxyheptadecanamido) butanamido]hexanoyl)[4A,7K,9E,10A,13E,18Q,22V,23A,28Y,30W,31L]-hPYY(4-36)

iVal-APEK(C18DA-gGlu-Ahx)PEADAEPEELQRYYVALRHYYNWLTRQRY-NH2 (SEQ ID NO: 10)

MW (calculated): 4778.5 Da

Synthesis and purification methods: S01; P01

LCMS: 010_CA07; Rt: 13.50 min; m/3: 1592.9 m/4: m/5:

Compound 7

N{alpha-4}-(3-methylbutanoyl)-N{epsilon-7}-(6-[(4S)-4-carboxy-4-(17-carboxyheptadecanamido) butanamido]hexanoyl)[4A,7K,9E,10A,13T,17I,18Q,22V,28Y,30W,31L]-hPYY(4-36)

iVal-APEK(C18DA-gGlu-Ahx)PEADATPEEIQRYYVSLRHYYNWLTRQRY-NH2 (SEQ ID NO: 11)

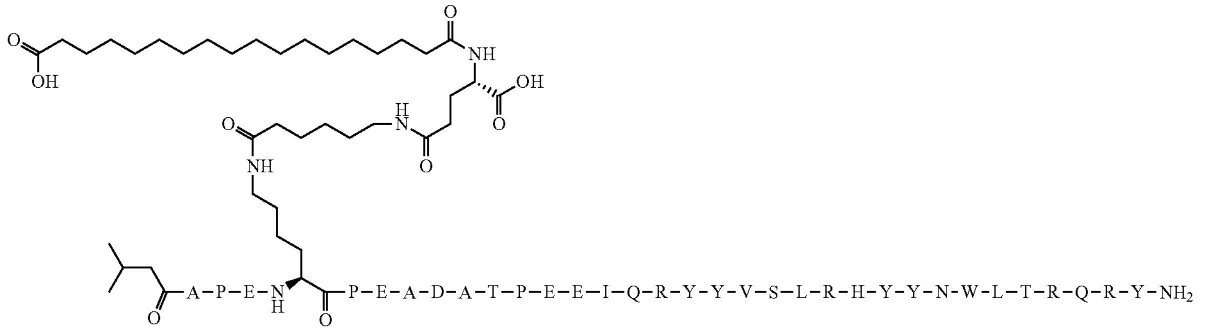

MW (calculated): 4766.4 Da

Synthesis and purification methods: S01; P01

LCMS: 010_CA07; Rt: 13.50 min; m/3: m/4: 1192.2 m/5:

Compound 8

N{alpha-4}-(3-methylbutanoyl)-N{epsilon-7}-(6-[(4S)-4-carboxy-4-(17-carboxyheptadecanamido) butanamido] hexanoyl)[4A,7K,9E,12E,13T,18Q,22V,28Y,30W,31L]-hPYY(4-36)

iVal-APEK(C18DA-gGlu-Ahx)PEEDET-PEELQRYYVSLRHYYNWLTRQRY-NH2 (SEQ ID NO: 12)

MW (calculated): 4676.4 Da

Synthesis and purification methods: S01; P02

LCMS: 010_CA07; Rt: 11.46 min; m/3: 1560.1 m/4: 1170.2 m/5:

Compound 11

N{alpha-4}-(3-methylbutanoyl)-N{epsilon-7}-(6-[(4S)-4-carboxy-4-(17-carboxyheptadecanamido) butanamido] hexanoyl)[4A,7K,9E,10A,17I,18Q,22I,28Y,30W,31L]-hPYY(4-36)

iVal-APEK(C18DA-gGlu-Ahx)PEADASPEEIQRYYIS-LRHYYNWLTRQRY-NH2 (SEQ ID NO: 15)

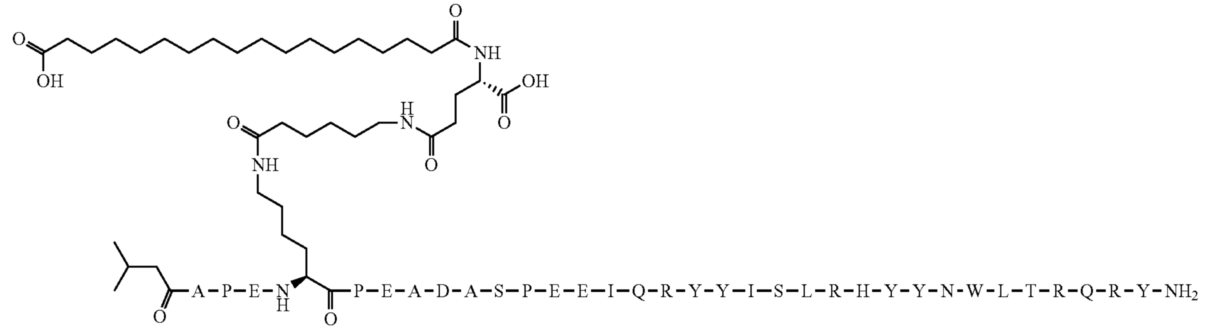

MW (calculated): 4882.5 Da

Synthesis and purification methods: S01; P02

LCMS: 010_CA07; Rt: 9.94 min; m/3: 1628.0 m/4: 1221.2 m/5:

Compound 9

N{alpha-4}-(3-methylbutanoyl)-N{epsilon-7}-(6-[(4S)-4-carboxy-4-(17-carboxyheptadecanamido) butanamido] hexanoyl)[4A,7K,9E,11Q,13T,18Q,22V,28Y,30W,31L]-hPYY(4-36)

iVal-APEK(C18DA-gGlu-Ahx)PEEQAT-PEELQRYYVSLRHYYNWLTRQRY-NH2 (SEQ ID NO: 13)

MW (calculated): 4837.5 Da

Synthesis and purification methods: S01; P01

LCMS: 010_CA07; Rt: 11.52 min; m/3: 1613.3 m/4: m/5:

Compound 10

N{alpha-4}-(3-methylbutanoyl)-N{epsilon-7}-(6-[(4S)-4-carboxy-4-(17-carboxyheptadecanamido) butanamido] hexanoyl)[4A,6A,7K,9E,10A,11A,13E,18Q,22V,23A,28Y,30W,31L]-hPYY(4-36)

iVal-APAK(C18DA-gGlu-Ahx)PEAAAEPEELQRYY-VALRHYYNWLTRQRY-NH2 (SEQ ID NO: 14)

MW (calculated): 4766.4 Da

Synthesis and purification methods: S01; P01

LCMS: 010_CA07; Rt: 10.29 min; m/3: 1589.8 m/4: m/5:

Compound 12

N{alpha-4}-(3-methylbutanoyl)-N{epsilon-7}-(6-[(4S)-4-carboxy-4-(17-carboxyheptadecanamido) butanamido] hexanoyl)[4A,7K,9E,18Q,19Q,22V,28Y,29H,30W,31L]-hPYY(4-36)

iVal-APEK(C18DA-gGlu-Ahx)PEE-DASPEELQQYYVSLRHYYHWLTRQRY-NH2 (SEQ ID NO: 16)

MW (calculated): 4805.4 Da

Synthesis and purification methods: S01; P01

LCMS: 010_CA07; Rt: 10.11 min; m/3: 1603.0 m/4: m/5:

Compound 13

N{alpha-4}-(3-methylbutanoyl)-N{epsilon-7}-(6-[(4S)-4-carboxy-4-(17-carboxyheptadecanamido) butanamido] hexanoyl)[4A,7K,9E,10A,17T,18Q,22V,28Y,30W,31L]-hPYY(4-36)

iVal-APEK(C18DA-gGlu-Ahx) PEADASPEETQRYYVSLRHYYNWLTRQRY-NH2 (SEQ ID NO: 17)

MW (calculated): 4740.4 Da

Synthesis and purification methods: S01; P02

LCMS: 010_CA07; Rt: 9.07 min; m/3: 1581.0 m/4: m/5:

Compound 14

N{alpha-4}-(3-methylbutanoyl)-N{epsilon-7}-(6-[(4S)-4-carboxy-4-(17-carboxyheptadecanamido) butanamido] hexanoyl)-[4A,7K,9P,18Q,22V,28Y,30W,31L]-hPYY(4-36)

iVal-APEK(C18DA-gGlu-Ahx)PPE-DASPEELQRYYVSLRHYYNWLTRQRY-NH2 (SEQ ID NO: 18)

MW (calculated): 4778.5 Da

Synthesis and purification methods: S01; P01

LCMS: 010_CA07; Rt: 9.97 min; m/3: m/4: 1195.0 m/5:

Compound 15

N{alpha-4}-(3-methylbutanoyl)-N{epsilon-7}-(6-[(4S)-4-carboxy-4-(17-carboxyheptadecanamido) butanamido] hexanoyl)[4A,7K,9E,17I,18Q,19Q,22V,28Y,30W,31L]-hPYY(4-36)

iVal-APEK(C18DA-gGlu-Ahx)PEEDASPEE-IQQYYVSLRHYYNWLTRQRY-NH2 (SEQ ID NO: 19)

MW (calculated): 4782.4 Da

Synthesis and purification methods: S01; P01

LCMS: 010_CA07; Rt: 10.28 min; m/3: 1595.5 m/4: m/5:

Compound 16

N{alpha-4}-(3-methylbutanoyl)-N{epsilon-7}-(6-[(4S)-4-carboxy-4-(17-carboxyheptadecanamido) butanamido] hexanoyl)[4A,7K,9E,13T,18Q,19K,22V,28Y,30W,31L]-hPYY(4-36)

iVal-APEK(C18DA-gGlu-Ahx)PEEDAT-PEELQKYYVSLRHYYNWLTRQRY-NH2 (SEQ ID NO: 20)

MW (calculated): 4796.5 Da

Synthesis and purification methods: S01; P01

LCMS: 010_CA07; Rt: 10.32 min; m/3: 1600.5 m/4: m/5:

Compound 17

N{alpha-4}-(3-methylbutanoyl)-N{epsilon-7}-(6-[(4S)-4-carboxy-4-(17-carboxyheptadecanamido) butanamido] hexanoyl)[4A,7K,9E,13T,17I,18Q,22P,28Y,30W,31L]-hPYY(4-36)

iVal-APEK(C18DA-gGlu-Ahx)PEEDATPEE-IQRYYPSLRHYYNWLTRQRY-NH2 (SEQ ID NO: 21)

MW (calculated): 4822.5 Da

Synthesis and purification methods: S01; P02

LCMS: 010_CA07; Rt: 9.35 min; m/3: 1608.2 m/4: m/5:

Compound 18

N{alpha-4}-(3-methylbutanoyl)-N{epsilon-7}-(6-[(4S)-4-carboxy-4-(17-carboxyheptadecanamido) butanamido] hexanoyl)[4A,7K,9E,18Q,22V,23A,28Y,30W,31L]-hPYY (4-36)

iVal-APEK(C18DA-gGlu-Ahx)PEEDASPEELQRYY-VALRHYYNWLTRQRY-NH2 (SEQ ID NO: 22)

MW (calculated): 4794.5 Da

Synthesis and purification methods: S01; P01

LCMS: 010_CA07; Rt: 10.50 min; m/3: m/4: 1199.4 m/5:

Compound 19

N{alpha-4}-(3-methylbutanoyl)-N{epsilon-7}-(6-[(4S)-4-carboxy-4-(17-carboxyheptadecanamido) butanamido] hexanoyl)[4A,7K,9E,13T,14E,18Q,22V,28Y,30W,31L]-hPYY(4-36)

iVal-APEK(C18DA-gGlu-Ahx)PEEDA-TEEELQRYYVSLRHYYNWLTRQRY-NH2 (SEQ ID NO: 23)

MW (calculated): 4856.5 Da

Synthesis and purification methods: S01; P02 LCMS: 010_CA07; Rt: 10.92 min; m/3: 1619.1 m/4: 1214.3 m/5:

Compound 20

N{alpha-4}-(3-methylbutanoyl)-N{epsilon-7}-(6-[(4S)-4-carboxy-4-(17-carboxyheptadecanamido) butanamido] hexanoyl)[4A,6A,7K,9E,18Q,21Q,22V,28Y,30W,31L]-hPYY(4-36)

iVal-APAK(C18DA-gGlu-Ahx)PEE-DASPEELQRYQVSLRHYYNWLTRQRY-NH2 (SEQ ID NO: 24)

MW (calculated): 4717.4 Da

Synthesis and purification methods: S01; P02

LCMS: 010_CA07; Rt: 9.67 min; m/3: 1572.9 m/4: 1180.1 m/5:

Compound 21

N{alpha-4}-(3-methylbutanoyl)-N{epsilon-7}-(6-[(4S)-4-carboxy-4-(17-carboxyheptadecanamido) butanamido] hexanoyl)[4A,7K,9E,13E,18Q,22V,23A,28Y,30W,31L]-hPYY(4-36)

iVal-APEK(C18DA-gGlu-Ahx)PEEDAEPEELQRYY-VALRHYYNWLTRQRY-NH2 (SEQ ID NO: 25)

MW (calculated): 4836.5 Da

Synthesis and purification methods: S01; P01

LCMS: 010_CA07; Rt: 13.50 min; m/3: m/4: 1209.8 m/5:

Compound 22

N{alpha-4}-(3-methylbutanoyl)-N{epsilon-7}-(6-[(4S)-4-carboxy-4-(17-carboxyheptadecanamido) butanamido] hexanoyl)[4A,7K,9E,12P,13T,18Q,22V,28Y,30W,31L]-hPYY(4-36)

iVal-APEK(C18DA-gGlu-Ahx)PEEDPT-PEELQRYYVSLRHYYNWLTRQRY-NH2 (SEQ ID NO: 26)

MW (calculated): 4850.5 Da

Synthesis and purification methods: S01; P02

LCMS: 010_CA07; Rt: 9.91 min; m/3: 1616.7 m/4: 1214.2 m/5:

Compound 23

N{alpha-4}-(3-methylbutanoyl)-N{epsilon-7}-(6-[(4S)-4-carboxy-4-(17-carboxyheptadecanamido) butanamido] hexanoyl)[4A,7K,9E,11E,18Q,22V,28Y,30W,31L]-hPYY (4-36)

iVal-APEK(C18DA-gGlu-Ahx)PEEE-ASPEELQRYYVSLRHYYNWLTRQRY-NH2 (SEQ ID NO: 27)

MW (calculated): 4824.5 Da

Synthesis and purification methods: S01; P01

LCMS: 010_CA07; Rt: 10.29 min; m/3: 1610.2 m/4: m/5:

Compound 24

N{alpha-4}-(3-methylbutanoyl)-N{epsilon-7}-(6-[(4S)-4-carboxy-4-(17-carboxyheptadecanamido) butanamido] hexanoyl)[4A,7K,9E,12S,18Q,22V,23A,28Y,30W,31L]-hPYY(4-36)

iVal-APEK(C18DA-gGlu-Ahx)PEEDSSPEELQRYY-VALRHYYNWLTRQRY-NH2 (SEQ ID NO: 28)

MW (calculated): 4810.5 Da

Synthesis and purification methods: S01; P01

LCMS: 010_CA07; Rt: 10.77 min; m/3: 1603.1 m/4: m/5:

Compound 25

N{alpha-4}-(3-methylbutanoyl)-N{epsilon-7}-(6-[(4S)-4-carboxy-4-(17-carboxyheptadecanamido) butanamido] hexanoyl)[4A,7K,9E,10A,13T,18Q,22I,28Y,30W,31L]-hPYY(4-36)

iVal-APEK(C18DA-gGlu-Ahx)PEADATPEELQRYYIS-LRHYYNWLTRQRY-NH2 (SEQ ID NO: 29)

MW (calculated): 4780.5 Da

Synthesis and purification methods: S01; P02

LCMS: 010_CA07; Rt: 10.39 min; m/3: m/4: 1195.1 m/5:

Compound 26

N{alpha-4}-(3-methylbutanoyl)-N{epsilon-7}-(6-[(4S)-4-carboxy-4-(17-carboxyheptadecanamido) butanamido] hexanoyl)[4A,6A,7K,9E,13T,18Q,22V,28Y,30W,31L]-hPYY(4-36)

iVal-APAK(C18DA-gGlu-Ahx)PEEDAT-PEELQRYYVSLRHYYNWLTRQRY-NH2 (SEQ ID NO: 30)

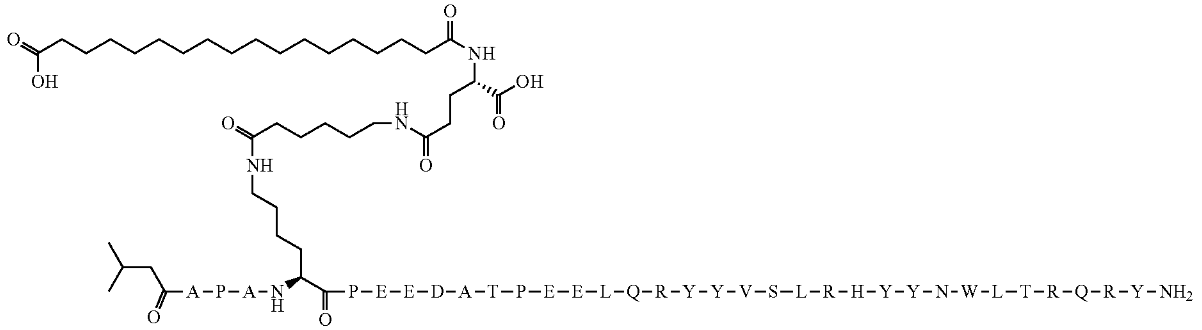

MW (calculated): 4766.4 Da

Synthesis and purification methods: S01; P02

LCMS: 010_CA07; Rt: 10.62 min; m/3: 1590.3 m/4: 1192.1 m/5: 954.2

Compound 27

N{alpha-4}-(3-methylbutanoyl)-N{epsilon-7}-(6-[(4S)-4-carboxy-4-(17-carboxyheptadecanamido) butanamido] hexanoyl)[4A,7K,9E,13E,17S,18Q,22V,28Y,30W,31L]-hPYY(4-36)

iVal-APEK(C18DA-gGlu-Ahx)PEEDAE-PEESQRYYVSLRHYYNWLTRQRY-NH2 (SEQ ID NO: 31)

MW (calculated): 4826.4 Da

Synthesis and purification methods: S01; P02

LCMS: 010_CA07; Rt: 9.31 min; m/3: 1609.1 m/4: m/5:

Compound 28

N{alpha-4}-(3-methylbutanoyl)-N{epsilon-7}-(6-[(4S)-4-carboxy-4-(17-carboxyheptadecanamido) butanamido] hexanoyl)[4A,7K,9P,13T,17I,18Q,22V,28Y,30W,31L]-hPYY(4-36)

iVal-APEK(C18DA-gGlu-Ahx)PPEDATPEE-IQRYYVSLRHYYNWLTRQRY-NH2 (SEQ ID NO: 32)

MW (calculated): 4792.5 Da

Synthesis and purification methods: S01; P02

LCMS: 010_CA07; Rt: 9.46 min; m/3: m/4: 1198.6 m/5:

Compound 29

N{alpha-4}-(3-methylbutanoyl)-N{epsilon-7}-(6-[(4S)-4-carboxy-4-(17-carboxyheptadecanamido) butanamido] hexanoyl)[4A,7K,9E,10A,12S,18Q,22V,28Y,30W,31L]-hPYY(4-36)

iVal-APEK(C18DA-gGlu-Ahx) PEADSSPEELQRYYVSLRHYYNWLTRQRY-NH2 (SEQ ID NO: 33)

MW (calculated): 4768.4 Da

Synthesis and purification methods: S01; P01

LCMS: 010_CA07; Rt: 10.22 min; m/3: 1589.1 m/4: m/5:

Compound 30

N{alpha-4}-(3-methylbutanoyl)-N{epsilon-7}-(6-[(4S)-4-carboxy-4-(17-carboxyheptadecanamido) butanamido] hexanoyl)[4A,7K,9P,10A,13T,18Q,22V,28Y,30W,31L]-hPYY(4-36)

iVal-APEK(C18DA-gGlu-Ahx)PPADAT-PEELQRYYVSLRHYYNWLTRQRY-NH2 (SEQ ID NO: 34)

MW (calculated): 4734.4 Da

Synthesis and purification methods: S01; P01

LCMS: 010_CA07; Rt: 10.10 min; m/3: m/4: 1184.1 m/5:

Compound 31

N{alpha-4}-(3-methylbutanoyl)-N{epsilon-7}-(6-[(4S)-4-carboxy-4-(17-carboxyheptadecanamido) butanamido] hexanoyl)[4A,7K,9E,13T,18Q,19P,22V,28Y,30W,31L]-hPYY(4-36)

iVal-APEK(C18DA-gGlu-Ahx)PEEDAT-PEELQPYYVSLRHYYNWLTRQRY-NH2 (SEQ ID NO: 35)

MW (calculated): 4765.4 Da

Synthesis and purification methods: S01; P01

LCMS: 010_CA07; Rt: 10.82 min; m/3: 1588.5 m/4: m/5:

Compound 32

N{alpha-4}-(3-methylbutanoyl)-N{epsilon-7}-(6-[(4S)-4-carboxy-4-(17-carboxyheptadecanamido) butanamido] hexanoyl)[4A,6A,7K,9E,18Q,22V,27Q,28Y,30W,31L]-hPYY(4-36)

iVal-APAK(C18DA-gGlu-Ahx)PEE-DASPEELQRYYVSLRHQYNWLTRQRY-NH2 (SEQ ID NO: 36)

MW (calculated): 4717.4 Da

Synthesis and purification methods: S01; P02

LCMS: 010_CA07; Rt: 9.65 min; m/3: 1573.1 m/4: 1181.1 m/5:

Compound 33

N{alpha-4}-(3-methylbutanoyl)-N{epsilon-7}-(6-[(4S)-4-carboxy-4-(17-carboxyheptadecanamido) butanamido] hexanoyl)[4A,6A,7K,9E,13E,18Q,22I,28Y,30W,31L]-hPYY(4-36)

iVal-APAK(C18DA-gGlu-Ahx)PEEDAEPEELQRYYIS-LRHYYNWLTRQRY-NH2 (SEQ ID NO: 37)

MW (calculated): 4808.5 Da

Synthesis and purification methods: S01; P02

LCMS: 010_CA07; Rt: 10.55 min; m/3: 1602.9 m/4: m/5:

Compound 34

N{alpha-4}-(3-methylbutanoyl)-N{epsilon-7}-(6-[(4S)-4-carboxy-4-(17-carboxyheptadecanamido) butanamido] hexanoyl)[4A,7K,9E,14A,18Q,19Q,22V,28Y,30W,31L]-hPYY(4-36)

iVal-APEK(C18DA-gGlu-Ahx)PEEDA-SAEELQQYYVSLRHYYNWLTRQRY-NH2 (SEQ ID NO: 38)

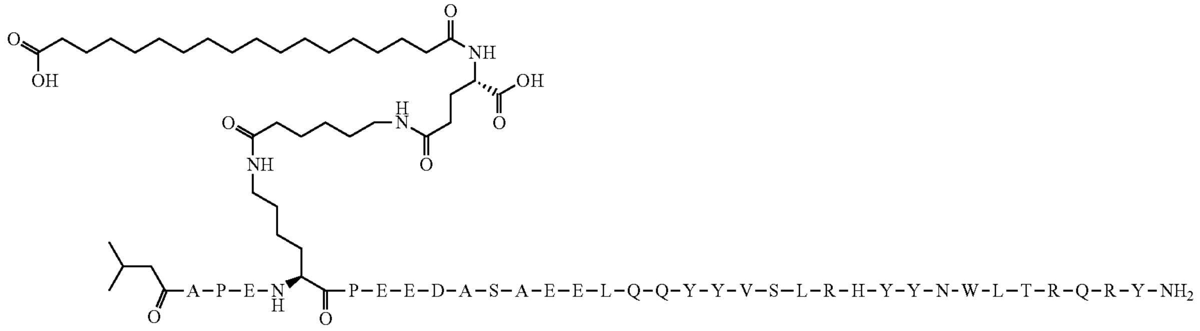

MW (calculated): 4756.4 Da

Synthesis and purification methods: S01; P02

LCMS: 010_CA07; Rt: 10.86 min; m/3: 1585.9 m/4: 1190.1 m/5:

Compound 35

N{alpha-4}-(3-methylbutanoyl)-N{epsilon-7}-(6-[(4S)-4-carboxy-4-(17-carboxyheptadecanamido) butanamido] hexanoyl)[4A,6A,7K,9E,11A,13T,18Q,22V,28Y,30W,31L]-hPYY(4-36)

iVal-APAK(C18DA-gGlu-Ahx)PEEAAT-PEELQRYYVSLRHYYNWLTRQRY-NH2 (SEQ ID NO: 39)

MW (calculated): 4722.4 Da

Synthesis and purification methods: S01; P01

LCMS: 010_CA07; Rt: 12.03 min; m/3: m/4: 1181.4 m/5:

Compound 36

N{alpha-4}-(3-methylbutanoyl)-N{epsilon-7}-(6-[(4S)-4-carboxy-4-(17-carboxyheptadecanamido) butanamido] hexanoyl)[4A,6A,7K,9E,11A,13T,17I,18Q,22V,28Y,30W, 31L]-hPYY(4-36)

iVal-APAK(C18DA-gGlu-Ahx)PEEAATPEE-IQRYYVSLRHYYNWLTRQRY-NH2 (SEQ ID NO: 40)

MW (calculated): 4722.4 Da

Synthesis and purification methods: S01; P02

LCMS: 010_CA07; Rt: 10.66 min; m/3: 1574.8 m/4: 1181.9 m/5:

Compound 37

N{alpha-4}-(3-methylbutanoyl)-N{epsilon-7}-(6-[(4S)-4-carboxy-4-(17-carboxyheptadecanamido) butanamido] hexanoyl)[4A,7K,9E,13E,18Q,22T,28Y,30W,31L]-hPYY (4-36)

iVal-APEK(C18DA-gGlu-Ahx)PEEDAEPEELQRYYT-SLRHYYNWLTRQRY-NH2 (SEQ ID NO: 41)

MW (calculated): 4854.5 Da

Synthesis and purification methods: S01; P01

LCMS: 010_CA07; Rt: 11.90 min; m/3: m/4: 1214.4 m/5:

Compound 38

N{alpha-4}-(3-methylbutanoyl)-N{epsilon-7}-(6-[(4S)-4-carboxy-4-(17-carboxyheptadecanamido) butanamido] hexanoyl)[4A,7K,9E,13T,18Q,19E,22V,28Y,30W,31L]-hPYY(4-36)

iVal-APEK(C18DA-gGlu-Ahx)PEEDAT-PEELQEYYVSLRHYYNWLTRQRY-NH2 (SEQ ID NO: 42)

MW (calculated): 4797.4 Da

Synthesis and purification methods: S01; P01

LCMS: 010_CA07; Rt: 10.38 min; m/3: 1600.9 m/4: m/5:

Compound 39

N{alpha-4}-(3-methylbutanoyl)-N{epsilon-7}-(6-[(4S)-4-carboxy-4-(17-carboxyheptadecanamido) butanamido] hexanoyl)[4A,7K,9E,16A,18Q,19E,22V,28Y,30W,31L]-hPYY(4-36)

iVal-APEK(C18DA-gGlu-Ahx)PEEDA-SPEALQEYYVSLRHYYNWLTRQRY-NH2 (SEQ ID NO: 43)

MW (calculated): 4725.3 Da

Synthesis and purification methods: S01; P02

LCMS: 010_CA07; Rt: 10.52 min; m/3: 1575.9 m/4: m/5:

Compound 40N{alpha-4}-(3-methylbutanoyl)-N{epsilon-7}-(6-[(4S)-4-carboxy-4-(17-carboxyheptade-canamido) butanamido]hexanoyl)[4A,7K,9E,10A,17I,18Q, 22I,23A,28Y,30W,31L]-hPYY(4-36)

iVal-APEK(C18DA-gGlu-Ahx)PEADASPEE-IQRYYIALRHYYNWLTRQRY-NH2 (SEQ ID NO: 44)

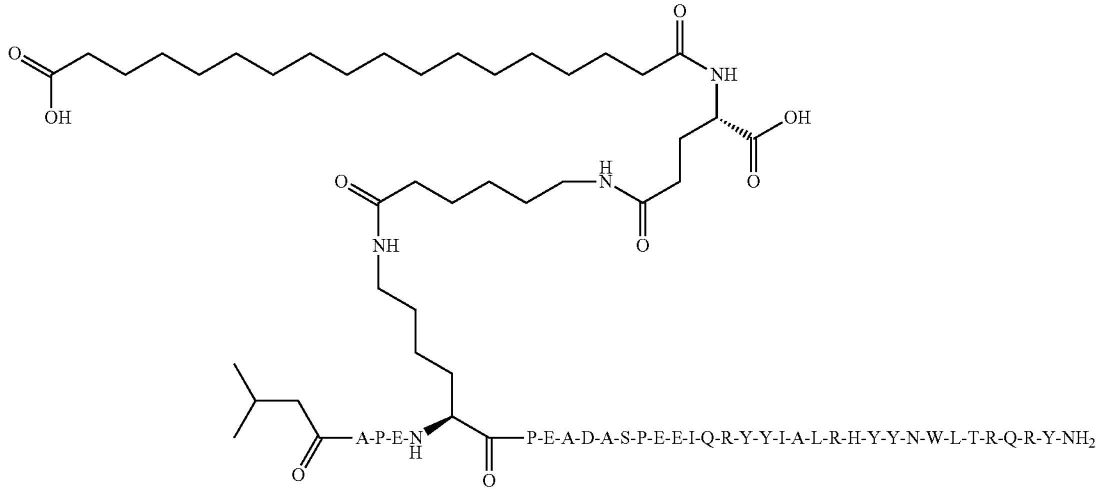

MW (calculated): 4750.4 Da

Synthesis and purification methods: S01; P01

LCMS: 010_CA07; Rt: 12.67 min; m/3: 1583.6 m/4: m/5:

Compound 41

N{alpha-4}-(3-methylbutanoyl)-N{epsilon-7}-(6-[(4S)-4-carboxy-4-(17-carboxyheptadecanamido) butanamido] hexanoyl)[4A,7K,9E,13E,18Q,22T,28Y,30W,31L]-hPYY (4-36)

iVal-APEK(C18DA-gGlu-Ahx)PEEDAEPEELQRYYT-SLRHYYQWLTRQRY-NH2 (SEQ ID NO: 45)

MW (calculated): 4868.5 Da

Synthesis and purification methods: S01; P02

LCMS: 010_CA07; Rt: 9.93 min; m/3: m/4: 1218.3 m/5:

Compound 42

N{alpha-4}-(3-methylbutanoyl)-N{epsilon-7}-(6-[(4S)-4-carboxy-4-(17-carboxyheptadecanamido) butanamido] hexanoyl)[4A,7K,9E,11P,13T,18Q,22V,28Y,30W,31L]-hPYY(4-36)

iVal-APEK(C18DA-gGlu-Ahx)PEEPAT-PEELQRYYVSLRHYYNWLTRQRY-NH2 (SEQ ID NO: 46)

MW (calculated): 4806.5 Da

Synthesis and purification methods: S01; P01

LCMS: 010_CA07; Rt: 11.57 min; m/3: 1603.0 m/4: m/5:

Compound 43

N{alpha-4}-(3-methylbutanoyl)-N{epsilon-7}-(6-[(4S)-4-carboxy-4-(17-carboxyheptadecanamido) butanamido] hexanoyl)[4A,6A,7K,9E,10A,11A,13E,18Q,22V,28Y,30W,31L]-hPYY(4-36)

iVal-APAK(C18DA-gGlu-Ahx)PEAAAE-PEELQRYYVSLRHYYNWLTRQRY-NH2 (SEQ ID NO: 47)

MW (calculated): 4692.4 Da

Synthesis and purification methods: S01; P02

LCMS: 010_CA07; Rt: 10.98 min; m/3: 1565.0 m/4: m/5:

Compound 44

N{alpha-4}-(3-methylbutanoyl)-N{epsilon-7}-(6-[(4S)-4-carboxy-4-(17-carboxyheptadecanamido) butanamido] hexanoyl)[4A,7K,9E,13T,18Q,22V,23G,28Y,30W,31L]-hPYY(4-36)

iVal-APEK(C18DA-gGlu-Ahx)PEEDAT-PEELQRYYVGLRHYYNWLTRQRY-NH2 (SEQ ID NO: 48)

MW (calculated): 4794.5 Da

Synthesis and purification methods: S01; P02

LCMS: 010_CA07; Rt: 10.20 min; m/3: m/4: 1199.3 m/5:

Compound 45

N{alpha-4}-(3-methylbutanoyl)-N{epsilon-7}-(6-[(4S)-4-carboxy-4-(17-carboxyheptadecanamido) butanamido] hexanoyl)-[4A,7K,9E,11I,13T,18Q,22V,28Y,30W,31L]-hPYY(4-36)

iVal-APEK(C18DA-gGlu-Ahx)PEEIAT-PEELQRYYVSLRHYYNWLTRQRY-NH2 (SEQ ID NO: 49)

MW (calculated): 4822.6 Da

Synthesis and purification methods: S01; P01

LCMS: 010_CA07; Rt: 12.49 min; m/3: 1608.4 m/4: m/5:

Compound 46

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13E,18Q,28Y,30W,31L]-hPYY(4-36)

iVal-APEK(C18DA-gGlu-Ahx)PEEDAE-PEELQRYYASLRHYYNWLTRQRY-NH2 (SEQ ID NO: 50)

MW (calculated): 4824.4 Da

Synthesis and purification methods: S01; P02

LCMS: 010_CA07; Rt: 13.52 min; m/3: 1609.4 m/4: 1206.3 m/5:

Compound 47

N{alpha-4}-(3-methylbutanoyl)-N{epsilon-7}-(6-[(4S)-4-carboxy-4-(17-carboxyheptadecanamido) butanamido] hexanoyl)-[4A,7K,9P,17I,18Q,22V,23A,28Y,30W,31L]-hPYY(4-36)

iVal-APEK(C18DA-gGlu-Ahx)PPEDASPEEIQRYY-VALRHYYNWLTRQRY-NH2 (SEQ ID NO: 51)

MW (calculated): 4762.5 Da

Synthesis and purification methods: S01; P02

LCMS: 010_CA07; Rt: 9.44 min; m/3: m/4: 1191.2 m/5:

Compound 48

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,11A,13T,18Q,22I,28Y,30W,31L]-hPYY(4-36)

iVal-APAK(C18DA-gGlu-Ahx)PEEAATPEELQRYYIS-LRHYYNWLTRQRY-NH2 (SEQ ID NO: 52)

MW (calculated): 4736.5 Da

Synthesis and purification methods: S01; P01

LCMS: 010_CA07; Rt: 12.10 min; m/3: m/4: 1185.0 m/5:

Compound 49

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,18Q,22V,23L,28Y,30W,31L]-hPYY(4-36)

iVal-APEK(C18DA-gGlu-Ahx)PEEDAT-PEELQRYYVLLRHYYNWLTRQRY-NH2 (SEQ ID NO: 53)

MW (calculated): 4850.6 Da

Synthesis and purification methods: S01; P02

LCMS: 010_CA07; Rt: 10.55 min; m/3: m/4: 1213.1 m/5:

Compound 50

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,17I,18Q,22V,23A,28Y,30W,31L]-hPYY(4-36)

iVal-APEK(C18DA-gGlu-Ahx)PEEDATPEEIQRYY-VALRHYYNWLTRQRY-NH2 (SEQ ID NO: 54)

MW (calculated): 4858.1 Da

Synthesis and purification methods: S01; P02

LCMS: 010_CA07; Rt: 13.00 min; m/3: m/4: 1215.5 m/5:

Compound 51

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,18Q,22V,23Q,28Y,30W,31L]-hPYY(4-36)

iVal-APEK(C18DA-gGlu-Ahx)PEEDAT-PEELQRYYVQLRHYYNWLTRQRY-NH2 (SEQ ID NO: 55)

MW (calculated): 4865.5 Da

Synthesis and purification methods: S01; P02

LCMS: 010_CA07; Rt: 9.86 min; m/3: m/4: 1217.2 m/5:

Compound 52

N{alpha-4}-(3-methylbutanoyl)-N{epsilon-7}-(6-[(4S)-4-carboxy-4-(17-carboxyheptadecanamido) butanamido] hexanoyl)-[4A,7K,9E,17I,18Q,22V,23E,28Y,30W,31L]-hPYY(4-36)

iVal-APEK(C18DA-gGlu-Ahx)PEEDASPEE-IQRYYVELRHYYNWLTRQRY-NH2 (SEQ ID NO: 56)

MW (calculated): 4852.5 Da

Synthesis and purification methods: S01; P01

LCMS: 010_CA07; Rt: 10.16 min; m/3: 1619.2 m/4: m/5:

Compound 53

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13E,17V,18Q,22V,28Y,30W,31L]-hPYY(4-36)

iVal-APEK(C18DA-gGlu-Ahx)PEEDAE-PEEVQRYYVSLRHYYNWLTRQRY-NH2 (SEQ ID NO: 57)

MW (calculated): 4838.5 Da

Synthesis and purification methods: S01; P02

LCMS: 010_CA07; Rt: 13.20 min; m/3: 1613.2 m/4: 1210.0 m/5:

Compound 54

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,17A,18Q,22V,28Y,30W,31L]-hPYY(4-36)

iVal-APEK(C18DA-gGlu-Ahx)PEEDATPEEA-QRYYVSLRHYYNWLTRQRY-NH2 (SEQ ID NO: 58)

MW (calculated): 4782.4 Da

Synthesis and purification methods: S01; P01

LCMS: 010_CA07; Rt: 9.71 min; m/3: 1594.9 m/4: m/5:

Compound 55

N{alpha-4}-(3-methylbutanoyl)-N{epsilon-7}-(6-[(4S)-4-carboxy-4-(17-carboxyheptadecanamido) butanamido] hexanoyl)-[4A,7K,9E,14E,17I,18Q,22V,28Y,30W,31L]-hPYY(4-36)

iVal-APEK(C18DA-gGlu-Ahx)PEEDASEEE-IQRYYVSLRHYYNWLTRQRY-NH2 (SEQ ID NO: 59)

MW (calculated): 4842.5 Da

Synthesis and purification methods: S01; P02

LCMS: 010_CA07; Rt: 10.23 min; m/3: 1614.8 m/4: m/5:

Compound 56

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,14A,18Q,22V,28Y,30W,31L]-hPYY(4-36)

iVal-APEK(C18DA-gGlu-Ahx)PEEDA-TAEELQRYYVSLRHYYNWLTRQRY-NH2 (SEQ ID NO: 60)

MW (calculated): 4798.4 Da

Synthesis and purification methods: S01; P01

LCMS: 010_CA07; Rt: 11.04 min; m/3: 1600.0 m/4: m/5:

Compound 57

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,13T,17A,18Q,22V,28Y,30W,31L]-hPYY(4-36)

iVal-APAK(C18DA-gGlu-Ahx)PEEDATPEEA-QRYYVSLRHYYNWLTRQRY-NH2 (SEQ ID NO: 61)

MW (calculated): 4724.4 Da

Synthesis and purification methods: S01; P01

LCMS: 010_CA07; Rt: 11.20 min; m/3: m/4: 1182.0 m/5:

Compound 58

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,17V,18Q,22V,28Y,30W,31L]-hPYY(4-36)

iVal-APEK(C18DA-gGlu-Ahx)PEEDAT-PEEVQRYYVSLRHYYNWLTRQRY-NH2 (SEQ ID NO: 62)

MW (calculated): 4810.5 Da

Synthesis and purification methods: S01; P01

LCMS: 010_CA07; Rt: 9.62 min; m/3: m/4: 1203.4 m/5:

Compound 59

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,18Q,22V,23Q,28Y,30W,31L]-hPYY(4-36)

iVal-APAK(C18DA-gGlu-Ahx)PEE-DASPEELQRYYVQLRHYYNWLTRQRY-NH2 (SEQ ID NO: 63)

MW (calculated): 4793.5 Da

Synthesis and purification methods: S01; P02

LCMS: 010_CA07; Rt: 9.88 min; m/3: 1598.7 m/4: m/5:

Compound 60

N{alpha-4}-(3-methylbutanoyl)-N{epsilon-7}-(6-[(4S)-4-carboxy-4-(17-carboxyheptadecanamido) butanamido] hexanoyl)-[4A,7K,9E,18Q,22V,28Y,29Q,30W,31L]-hPYY(4-36)

iVal-APEK(C18DA-gGlu-Ahx)PEE-DASPEELQRYYVSLRHYYQWLTRQRY-NH2 (SEQ ID NO: 64)

MW (calculated): 4824.5 Da

Synthesis and purification methods: S01; P02

LCMS: 010_CA07; Rt: 9.59 min; m/3: 1609.4 m/4: m/5:

Compound 61

N{alpha-4}-(3-methylbutanoyl)-N{epsilon-7}-(6-[(4S)-4-carboxy-4-(17-carboxyheptadecanamido) butanamido] hexanoyl)-[4A,7K,9P,10A,17I,18Q,22V,28Y,30W,31L]-hPYY(4-36)

iVal-APEK(C18DA-gGlu-Ahx)PPADASPEE-IQRYYVSLRHYYNWLTRQRY-NH2 (SEQ ID NO: 65)

MW (calculated): 4720.4 Da

Synthesis and purification methods: S01; P01

LCMS: 010_CA07; Rt: 9.70 min; m/3: m/4: 1181.5 m/5:

Compound 62

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9P,18Q,22V,23E,28Y,30W,31L]-hPYY(4-36)

iVal-APAK(C18DA-gGlu-Ahx)PPE-DASPEELQRYYVELRHYYNWLTRQRY-NH2 (SEQ ID NO: 66)

MW (calculated): 4762.5 Da

Synthesis and purification methods: S01; P01

LCMS: 010_CA07; Rt: 9.43 min; m/3: 1588.6 m/4: m/5:

Compound 63

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,17I,18Q,22V,28Y,30W,31L]-hPYY(4-36)

iVal-APAK(C18DA-gGlu-Ahx)PEEDASPEE-IQRYYVSLRHYYNWLTRQRY-NH2 (SEQ ID NO: 67)

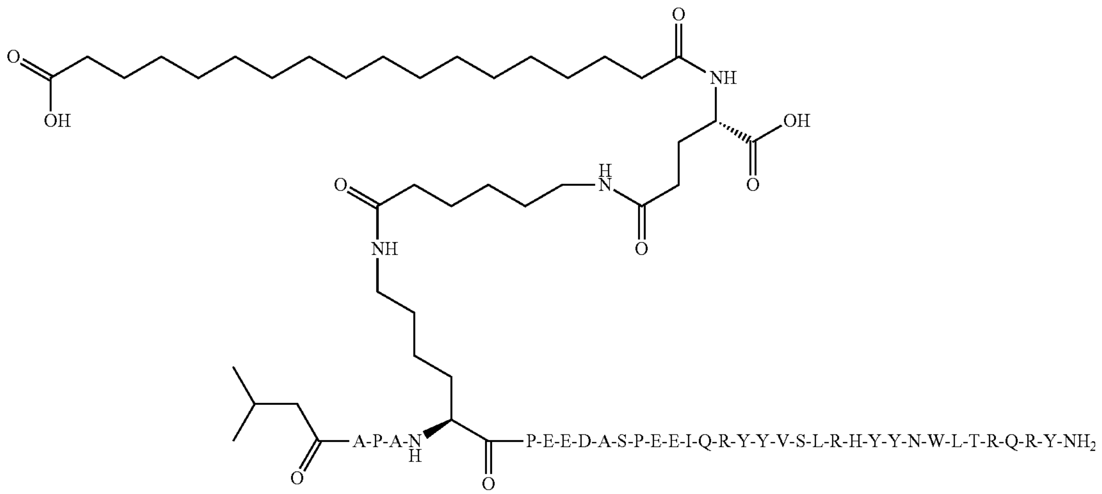

MW (calculated): 4752.4 Da

Synthesis and purification methods: S01; P01

LCMS: 010_CA07; Rt: 10.35 min; m/3: 1585.2 m/4: m/5:

Compound 64

N{alpha-4}-(3-methylbutanoyl)-N{epsilon-7}-(6-[(4S)-4-carboxy-4-(17-carboxyheptadecanamido) butanamido] hexanoyl)-[4A,7K,9P,13T,17I,18Q,22V,23A,28Y,30W,31L]-hPYY(4-36)

iVal-APEK(C18DA-gGlu-Ahx)PPEDATPEEIQRYYVALRHYYNWLTRQRY-NH2 (SEQ ID NO: 68)

MW (calculated): 4776.5 Da

Synthesis and purification methods: S01; P01

LCMS: 010_CA07; Rt: 11.50 min; m/3: m/4: 1194.9 m/5:

Compound 65

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,17I,18Q,22I,23A,28Y,30W,31L]-hPYY(4-36)

iVal-APAK(C18DA-gGlu-Ahx)PEEDASPEEIQRYYIALRHYYNWLTRQRY-NH2 (SEQ ID NO: 69)

MW (calculated): 4750.4 Da

Synthesis and purification methods: S01; P02

LCMS: 010_CA07; Rt: 10.18 min; m/3: m/4: 1187.8 m/5:

Compound 66

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,18Q,22I,28Y,30W,31L]-hPYY(4-36)

iVal-APEK(C18DA-gGlu-Ahx)PEEDATPEELQRYYISLRHYYNWLTRQRY-NH2 (SEQ ID NO: 70)

MW (calculated): 4838.5 Da

Synthesis and purification methods: S01; P01

LCMS: 010_CA07; Rt: 13.60 min; m/3: 1613.2 m/4: m/5:

Compound 67

N{alpha-4}-(3-methylbutanoyl)-N{epsilon-7}-(6-[(4S)-4-carboxy-4-(17-carboxyheptadecanamido) butanamido] hexanoyl)-[4A,7K,9E,17T,18Q,22V,23A,28Y,30W,31L]-hPYY(4-36)

iVal-APEK(C18DA-gGlu-Ahx)PEEDASPEETQRYYVALRHYYNWLTRQRY-NH2 (SEQ ID NO: 71)

MW (calculated): 4782.4 Da

Synthesis and purification methods: S01; P01

LCMS: 010_CA07; Rt: 9.86 min; m/3: 1595.1 m/4: m/5:

Compound 68

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13E,18Q,22V,28Y,29Q,30W,31L]-hPYY(4-36)

iVal-APEK(C18DA-gGlu-Ahx)PEEDAEPEELQRYYVSLRHYYQWLTRQRY-NH2 (SEQ ID NO: 72)

MW (calculated): 4866.5 Da

Synthesis and purification methods: S01; P02

LCMS: 010_CA07; Rt: 10.02 min; m/3: m/4: 1217.4 m/5:

Compound 69

N{alpha-4}-(3-methylbutanoyl)-N{epsilon-7}-(6-[(4S)-4-carboxy-4-(17-carboxyheptadecanamido) butanamido] hexanoyl)-[4A,7K,9P,10A,17T,18Q,22V,28Y,30W,31L]-hPYY(4-36)

iVal-APEK(C18DA-gGlu-Ahx)PPADASPEETQRYYVSLRHYYNWLTRQRY-NH2 (SEQ ID NO: 73)

MW (calculated): 4708.4 Da

Synthesis and purification methods: S01; P01

LCMS: 010_CA07; Rt: 9.50 min; m/3: m/4: 1178.1 m/5:

Compound 70

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,13T,18Q,22I,23A,28Y,30W,31L]-hPYY(4-36)

iVal-APAK(C18DA-gGlu-Ahx)PEEDATPEELQRYYIALRHYYNWLTRQRY-NH2 (SEQ ID NO: 74)

MW (calculated): 4764.5 Da

Synthesis and purification methods: S01; P02

LCMS: 010_CA07; Rt: 10.55 min; m/3: m/4: 1192.4 m/5:

Compound 71

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,13E,18Q,22V,23A,28Y,30W,31L]-hPYY(4-36)

iVal-APAK(C18DA-gGlu-Ahx)PEEDAEPEELQRYYVALRHYYNWLTRQRY-NH2 (SEQ ID NO: 75)

MW (calculated): 4778.5 Da

Synthesis and purification methods: S01; P02

LCMS: 010_CA07; Rt: 13.10 min; m/3: m/4: 1196.0 m/5:

Compound 72

N{alpha-4}-(3-methylbutanoyl)-N{epsilon-7}-(6-[(4S)-4-carboxy-4-(17-carboxyheptadecanamido) butanamido] hexanoyl)-[4A,7K,9E,10A,13E,18Q,22V,28Y,30W,31L]-hPYY(4-36)

iVal-APEK(C18DA-gGlu-Ahx)PEADAEPEELQRYYVSLRHYYNWLTRQRY-NH2 (SEQ ID NO: 76)

MW (calculated): 4794.5 Da

Synthesis and purification methods: S01; P01

LCMS: 010_CA07; Rt: 10.71 min; m/3: 1598.4 m/4: m/5:

Compound 73

N{alpha-4}-(3-methylbutanoyl)-N{epsilon-7}-(6-[(4S)-4-carboxy-4-(17-carboxyheptadecanamido) butanamido] hexanoyl)-[4A,7K,9E,11A,18Q,22V,23A,28Y,30W,31L]-hPYY(4-36)

iVal-APEK(C18DA-gGlu-Ahx)PEEAASPEELQRYYVALRHYYNWLTRQRY-NH2 (SEQ ID NO: 77)

MW (calculated): 4750.4 Da

Synthesis and purification methods: S01; P01

LCMS: 010_CA07; Rt: 13.24 min; m/3: 1584.1 m/4: m/5:

Compound 74

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,18Q,22V,23A,28Y,30W,31L]-hPYY(4-36)

iVal-APEK(C18DA-gGlu-Ahx)PEEDATPEELQRYYVALRHYYNWLTRQRY-NH2 (SEQ ID NO: 78)

MW (calculated): 4808.5 Da

Synthesis and purification methods: S01; P01

LCMS: 010_CA07; Rt: 13.70 min; m/3: m/4: 1203.1 m/5:

Compound 75

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13P,17I,18Q,22V,28Y,30W,31L]-hPYY(4-36)

iVal-APEK(C18DA-gGlu-Ahx)PEEDAPPEEIQRYYVSLRHYYNWLTRQRY-NH2 (SEQ ID NO: 79)

MW (calculated): 4820.5 Da

Synthesis and purification methods: S01; P01

LCMS: 010_CA07; Rt: 10.30 min; m/3: m/4: 1207.1 m/5:

Compound 76

N{alpha-4}-(3-methylbutanoyl)-N{epsilon-7}-(6-[(4S)-4-carboxy-4-(17-carboxyheptadecanamido) butanamido] hexanoyl)-[4A,7K,9E,18Q,22I,28Y,30W,31L]-hPYY(4-36)

iVal-APEK(C18DA-gGlu-Ahx)PEEDASPEELQRYYIS-LRHYYNWLTRQRY-NH2 (SEQ ID NO: 80)

MW (calculated): 4824.5 Da

Synthesis and purification methods: S01; P01

LCMS: U046_001; Rt: 11.60 min; m/3: 1609.0 m/4: m/5:

Compound 77

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,18Q,22V,28Q,30W,31L]-hPYY (4-36)

iVal-APAK(C18DA-gGlu-Ahx)PEE-DASPEELQRYYVSLRHYQNWLTRQRY-NH2 (SEQ ID NO: 81)

MW (calculated): 4717.4 Da

Synthesis and purification methods: S01; P02

LCMS: 010_CA07; Rt: 9.51 min; m/3: 1572.9 m/4: 1180.4 m/5:

Compound 78

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,18Q,22V,28Y,29Q,30W,31L]-hPYY(4-36)

iVal-APAK(C18DA-gGlu-Ahx)PEE-DASPEELQRYYVSLRHYYQWLTRQRY-NH2 (SEQ ID NO: 82)

MW (calculated): 4766.4 Da

Synthesis and purification methods: S01; P01

LCMS: 010_CA07; Rt: 10.00 min; m/3: 1589.9 m/4: m/5:

Compound 79

N{alpha-4}-(3-methylbutanoyl)-N{epsilon-7}-(6-[(4S)-4-carboxy-4-(17-carboxyheptadecanamido) butanamido] hexanoyl)-[4A,7K,9E,18Q,22V,28Y,30W,31L]-hPYY(4-36)

iVal-APEK(C18DA-gGlu-Ahx)PEE-DASPEELQRYYVSLRHYYNWLTRQRY-NH2 (SEQ ID NO: 83)

MW (calculated): 4810.5 Da

Synthesis and purification methods: S01; P02

LCMS: 010_CA07; Rt: 10.11 min; m/3: m/4: 1203.5 m/5:

Compound 80

N{alpha-4}-(3-methylbutanoyl)-N{epsilon-7}-(6-[(4S)-4-carboxy-4-(17-carboxyheptadecanamido) butanamido] hexanoyl)-[4A,7K,9E,14E,15A,18Q,22V,28Y,30W,31L]-hPYY(4-36)

iVal-APEK(C18DA-gGlu-Ahx)PEEDASEAEL-QRYYVSLRHYYNWLTRQRY-NH2 (SEQ ID NO: 84)

MW (calculated): 4784.4 Da

Synthesis and purification methods: S01; P02

LCMS: 010_CA07; Rt: 10.52 min; m/3: 1594.9 m/4: m/5:

Compound 81

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13Q,17I,18Q,22V,28Y,30W,31L]-hPYY(4-36)

iVal-APEK(C18DA-gGlu-Ahx)PEEDAQPEE-IQRYYVSLRHYYNWLTRQRY-NH2 (SEQ ID NO: 85)

MW (calculated): 4851.5 Da

Synthesis and purification methods: S01; P02

LCMS: 010_CA07; Rt: 9.87 min; m/3: 1618.2 m/4: 1214.5 m/5:

Compound 82

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9P,17I,18Q,22V,28Y,30W,31L]-hPYY(4-36)

iVal-APAK(C18DA-gGlu-Ahx)PPEDASPEE-IQRYYVSLRHYYNWLTRQRY-NH2 (SEQ ID NO: 86)

MW (calculated): 4720.4 Da

Synthesis and purification methods: S01; P01

LCMS: 010_CA07; Rt: 9.36 min; m/3: 1574.2 m/4: m/5:

Compound 83

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,14S,18Q,22V,28Y,30W,31L]-hPYY(4-36)

iVal-APEK(C18DA-gGlu-Ahx)PEEDAT-SEELQRYYVSLRHYYNWLTRQRY-NH2 (SEQ ID NO: 87)

MW (calculated): 4814.4 Da

Synthesis and purification methods: S01; P02

LCMS: 010_CA07; Rt: 10.69 min; m/3: 1605.0 m/4: 1204.4 m/5:

Compound 84

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,17I,18Q,22V,23A,28Y,30W,31L]-hPYY(4-36)

iVal-APEK(C18DA-gGlu-Ahx)PEEDATPEEIQRYY-VALRHYYNWLTRQRY-NH2 (SEQ ID NO: 88)

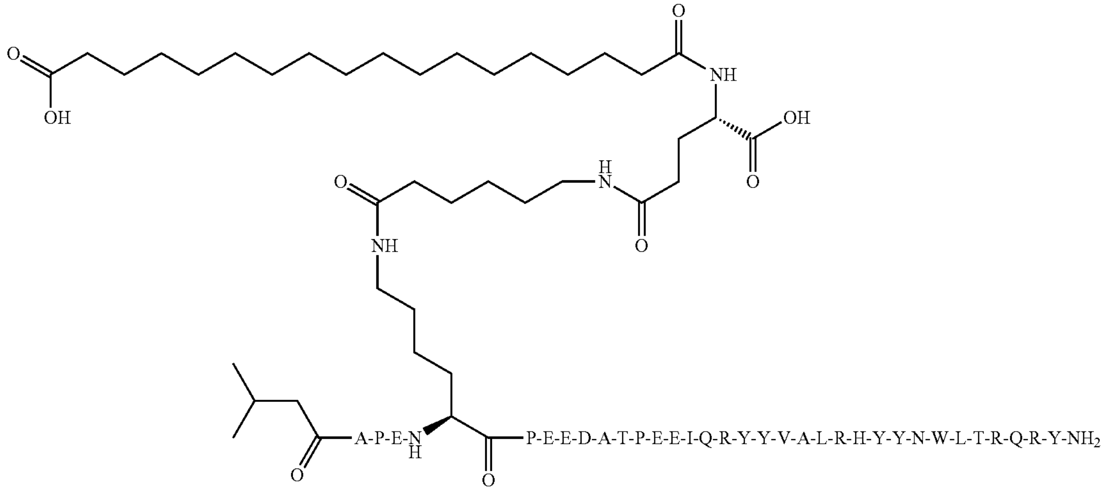

MW (calculated): 4808.5 Da

Synthesis and purification methods: S01; P01

LCMS: 010_CA07; Rt: 13.60 min; m/3: m/4: 1202.9 m/5:

Compound 85

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,17T,18Q,22V,28Y,30W,31L]-hPYY(4-36)

iVal-APAK(C18DA-gGlu-Ahx)PEE-DASPEETQRYYVSLRHYYNWLTRQRY-NH2 (SEQ ID NO: 89)

MW (calculated): 4740.4 Da

Synthesis and purification methods: S01; P02

LCMS: 010_CA07; Rt: 9.15 min; m/3: m/4: 1186.2 m/5:

Compound 86

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,17I,18Q,28Y,30W,31L]-hPYY(4-36)

iVal-APEK(C18DA-gGlu-Ahx)PEEDATPEE-IQRYYASLRHYYNWLTRQRY-NH2 (SEQ ID NO: 90)

MW (calculated): 4796.4 Da

Synthesis and purification methods: S01; P02

LCMS: 010_CA07; Rt: 9.67 min; m/3: m/4: 1200.1 m/5:

Compound 87

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,18Q,22V,23P,28Y,30W,31L]-hPYY(4-36)

iVal-APEK(C18DA-gGlu-Ahx)PEEDAT-PEELQRYYVPLRHYYNWLTRQRY-NH2 (SEQ ID NO: 91)

MW (calculated): 4834.5 Da

Synthesis and purification methods: S01; P02

LCMS: 010_CA07; Rt: 10.25 min; m/3: m/4: 1209.3 m/5:

Compound 88

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,18Q,20Q,22V,28Y,30W,31L]-hPYY(4-36)

iVal-APEK(C18DA-gGlu-Ahx)PEEDAT-PEELQRQYVSLRHYYNWLTRQRY-NH2 (SEQ ID NO: 92)

MW (calculated): 4789.4 Da

Synthesis and purification methods: S01; P01

LCMS: 010_CA07; Rt: 9.60 min; m/3: 1596.6 m/4: m/5:

Compound 89

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9P,18Q,22V,23A,28Y,30W,31L]-hPYY(4-36)

iVal-APAK(C18DA-gGlu-Ahx)PPEDASPEELQRYY-VALRHYYNWLTRQRY-NH2 (SEQ ID NO: 93)

MW (calculated): 4704.4 Da

Synthesis and purification methods: S01; P01

LCMS: 010_CA07; Rt: 12.20 min; m/3: 1568.4 m/4: m/5:

Compound 90

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,18Q,22V,23V,28Y,30W,31L]-hPYY(4-36)

iVal-APEK(C18DA-gGlu-Ahx)PEEDAT-PEELQRYYVVLRHYYNWLTRQRY-NH2 (SEQ ID NO: 94)

MW (calculated): 4836.5 Da

Synthesis and purification methods: S01; P02

LCMS: 010_CA07; Rt: 10.76 min; m/3: m/4: 1209.9 m/5:

Compound 91

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13E,18Q,22T,28Y,29H,30W,31L]-hPYY(4-36)

iVal-APEK(C18DA-gGlu-Ahx)PEEDAEPEELQRYYT-SLRHYYHWLTRQRY-NH2 (SEQ ID NO: 95)

MW (calculated): 4877.5 Da

Synthesis and purification methods: S01; P01

LCMS: 010_CA07; Rt: 10.22 min; m/3: 1628.8 m/4: m/5:

Compound 92

N{alpha-4}-(3-methylbutanoyl)-N{epsilon-7}-(6-[(4S)-4-carboxy-4-(17-carboxyheptadecanamido) butanamido] hexanoyl)-[4A,7K,18Q,22I,28Y,30W,31L]-hPYY(4-36)

iVal-APEK(C18DA-gGlu-Ahx)PGEDASPEELQRYYIS-LRHYYNWLTRQRY-NH2 (SEQ ID NO: 96)

MW (calculated): 4752.4 Da

Synthesis and purification methods: S01; P02

LCMS: 010_CA07; Rt: 10.75 min; m/3: 1585.3 m/4: 1188.4 m/5:

Compound 93

N{alpha-4}-(3-methylbutanoyl)-N{epsilon-7}-(6-[(4S)-4-carboxy-4-(17-carboxyheptadecanamido) butanamido] hexanoyl)-[4A,7K,9E,17I,18Q,22V,23Q,28Y,30W,31L]-hPYY(4-36)

iVal-APEK(C18DA-gGlu-Ahx)PEEDASPEE-IQRYYVQLRHYYNWLTRQRY-NH2 (SEQ ID NO: 97)

MW (calculated): 4851.5 Da

Synthesis and purification methods: S01; P02

LCMS: 010_CA07; Rt: 9.64 min; m/3: m/4: 1213.4 m/5:

Compound 94

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,10A,18Q,22V,23E,28Y,30W,31L]-hPYY(4-36)

iVal-APAK(C18DA-gGlu-Ahx) PEADASPEELQRYYVELRHYYNWLTRQRY-NH2 (SEQ ID NO: 98)

MW (calculated): 4736.4 Da

Synthesis and purification methods: S01; P01

LCMS: 010_CA07; Rt: 10.07 min; m/3: 1578.9 m/4: m/5:

Compound 95

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,18Q,19A,22V,28Y,30W,31L]-hPYY(4-36)

iVal-APEK(C18DA-gGlu-Ahx)PEEDAT-PEELQAYYVSLRHYYNWLTRQRY-NH2 (SEQ ID NO: 99)

MW (calculated): 4739.4 Da

Synthesis and purification methods: S01; P01

LCMS: 010_CA07; Rt: 13.31 min; m/3: 1579.5 m/4: m/5:

Compound 96

N{alpha-4}-(3-methylbutanoyl)-N{epsilon-7}-(6-[(4S)-4-carboxy-4-(17-carboxyheptadecanamido) butanamido] hexanoyl)-[4A,7K,9E,11S,13T,18Q,22V,28Y,30W,31L]-hPYY(4-36)

iVal-APEK(C18DA-gGlu-Ahx)PEESAT-PEELQRYYVSLRHYYNWLTRQRY-NH2 (SEQ ID NO: 100)

MW (calculated): 4796.5 Da

Synthesis and purification methods: S01; P01

LCMS: 010_CA07; Rt: 9.90 min; m/3: 1599.4 m/4: m/5:

Compound 97

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,17I,18Q,22L,28Y,30W,31L]-hPYY(4-36)

iVal-APEK(C18DA-gGlu-Ahx)PEEDATPEE-IQRYYLSLRHYYNWLTRQRY-NH2 (SEQ ID NO: 101)

MW (calculated): 4838.5 Da

Synthesis and purification methods: S01; P02

LCMS: 010_CA07; Rt: 9.88 min; m/3: 1613.3 m/4: m/5:

Compound 98

N{alpha-4}-(3-methylbutanoyl)-N{epsilon-7}-(6-[(4S)-4-carboxy-4-(17-carboxyheptadecanamido) butanamido] hexanoyl)-[4A,7K,9E,10A,13T,17I,18Q,22V,28Y,30W,31L]-hPYY(4-36)

iVal-APEK(C18DA-gGlu-Ahx)PEADATPEE-IQRYYVSLRHYYNWLTRQRY-NH2 (SEQ ID NO: 102)

MW (calculated): 4816.1 Da

Synthesis and purification methods: S01; P02

LCMS: 010_CA07; Rt: 13.35 min; m/3: 1606.6 m/4: m/5:

Compound 99

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,13T,17I,18Q,22V,23A,28Y,30W,31L]-hPYY(4-36)

iVal-APAK(C18DA-gGlu-Ahx)PEEDATPEEIQRYY-VALRHYYNWLTRQRY-NH2 (SEQ ID NO: 103)

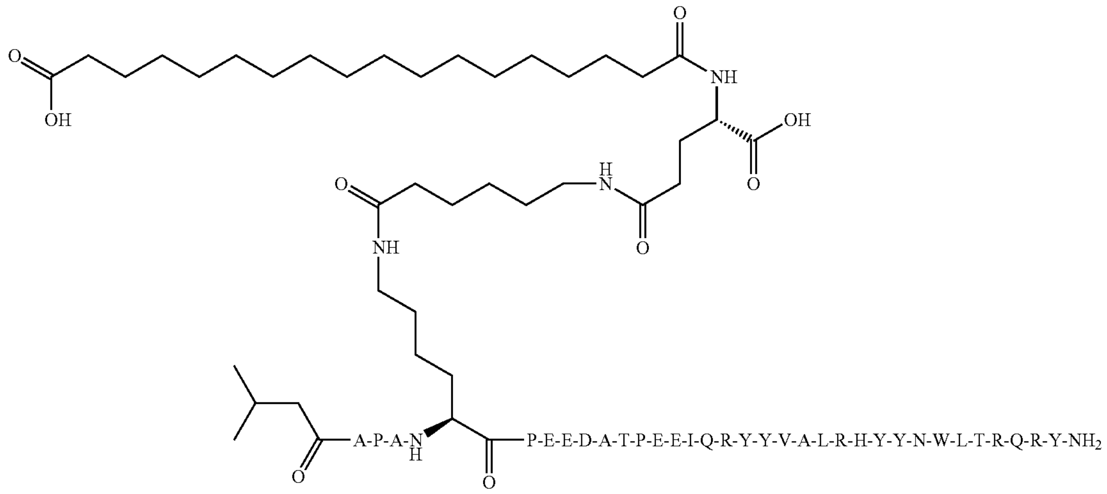

MW (calculated): 4750.4 Da

Synthesis and purification methods: S01; P01

LCMS: 010_CA07; Rt: 11.90 min; m/3: m/4: 1188.5 m/5:

Compound 100

N{alpha-4}-(3-methylbutanoyl)-N{epsilon-7}-(6-[(4S)-4-carboxy-4-(17-carboxyheptadecanamido) butanamido] hexanoyl)-[4A,7K,9E,10A,13T,18Q,22I,23A,28Y,30W,31L]-hPYY(4-36)

iVal-APEK(C18DA-gGlu-Ahx)PEADAT-PEELQRYYIALRHYYNWLTRQRY-NH2 (SEQ ID NO: 104)

MW (calculated): 4764.5 Da

Synthesis and purification methods: S01; P01

LCMS: 010_CA07; Rt: 12.10 min; m/3: m/4: 1192.2 m/5:

Compound 101

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,13T,18Q,22V,23A,28Y,30W,31L]-hPYY(4-36)

iVal-APAK(C18DA-gGlu-Ahx)PEEDATPEELQRYY-VALRHYYNWLTRQRY-NH2 (SEQ ID NO: 105)

MW (calculated): 4750.4 Da

Synthesis and purification methods: S01; P02

LCMS: 010_CA07; Rt: 12.28 min; m/3: m/4: 1188.8 m/5:

Compound 102

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,14L,18Q,22V,28Y,30W,31L]-hPYY(4-36)

iVal-APEK(C18DA-gGlu-Ahx)PEED-ATLEELQRYYVSLRHYYNWLTRQRY-NH2 (SEQ ID NO: 106)

MW (calculated): 4840.5 Da

Synthesis and purification methods: S01; P02

LCMS: 010_CA07; Rt: 11.96 min; m/3: 1613.9 m/4: 1210.9 m/5:

Compound 103

N{alpha-4}-(3-methylbutanoyl)-N{epsilon-7}-(6-[(4S)-4-carboxy-4-(17-carboxyheptadecanamido) butanamido] hexanoyl)-[4A,7K,9E,14A,18Q,22V,23A,28Y,30W,31L]-hPYY(4-36)

iVal-APEK(C18DA-gGlu-Ahx)PEEDASAEELQRYY-VALRHYYNWLTRQRY-NH2 (SEQ ID NO: 107)

MW (calculated): 4768.4 Da

Synthesis and purification methods: S01; P02

LCMS: 010_CA07; Rt: 10.95 min; m/3: 1590.9 m/4: 1193.5 m/5:

Compound 104

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13E,17A,18Q,22V,28Y,30W,31L]-hPYY(4-36)

iVal-APEK(C18DA-gGlu-Ahx)PEEDAEPEEA-QRYYVSLRHYYNWLTRQRY-NH2 (SEQ ID NO: 108)

MW (calculated): 4882.5 Da

Synthesis and purification methods: S01; P01

LCMS: 010_CA07; Rt: 12.00 min; m/3: m/4: 1221.8 m/5:

Compound 105

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,14Q,18Q,22V,28Y,30W,31L]-hPYY(4-36)

iVal-APEK(C18DA-gGlu-Ahx)PEED-ATQEELQRYYVSLRHYYNWLTRQRY-NH2 (SEQ ID NO: 109)

MW (calculated): 4855.5 Da

Synthesis and purification methods: S01; P02

LCMS: 010_CA07; Rt: 10.63 min; m/3: 1618.4 m/4: 1215.2 m/5:

Compound 106

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,18Q,22V,23A,28Y,30W,31L]-hPYY(4-36)

iVal-APAK(C18DA-gGlu-Ahx)PEEDASPEELQRYY-VALRHYYNWLTRQRY-NH2 (SEQ ID NO: 110)

MW (calculated): 4736.4 Da

Synthesis and purification methods: S01; P01

LCMS: 010_CA07; Rt: 10.50 min; m/3: m/4: 1185.0 m/5:

Compound 107

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13E,17T,18Q,22V,28Y,30W,31L]-hPYY(4-36)

iVal-APEK(C18DA-gGlu-Ahx)PEEDAE-PEETQRYYVSLRHYYNWLTRQRY-NH2 (SEQ ID NO: 111)

MW (calculated): 4840.4 Da

Synthesis and purification methods: S01; P01

LCMS: 010_CA07; Rt: 11.30 min; m/3: 1614.3 m/4: m/5:

Compound 108

N{alpha-4}-(3-methylbutanoyl)-N{epsilon-7}-(6-[(4S)-4-carboxy-4-(17-carboxyheptadecanamido) butanamido] hexanoyl)-[4A,7K,9E,10A,14E,18Q,22V,28Y,30W,31L]-hPYY(4-36)

iVal-APEK(C18DA-gGlu-Ahx)PEADA-SEEELQRYYVSLRHYYNWLTRQRY-NH2 (SEQ ID NO: 112)

MW (calculated): 4784.4 Da

Synthesis and purification methods: S01; P02

LCMS: 010_CA07; Rt: 10.71 min; m/3: 1595.5 m/4: 1196.7 m/5:

Compound 109

N{alpha-4}-(3-methylbutanoyl)-N{epsilon-7}-(6-[(4S)-4-carboxy-4-(17-carboxyheptadecanamido) butanamido] hexanoyl)-[4A,7K,9E,12L,13T,18Q,22V,28Y,30W,31L]-hPYY(4-36)

iVal-APEK(C18DA-gGlu-Ahx)PEEDLT-PEELQRYYVSLRHYYNWLTRQRY-NH2 (SEQ ID NO: 113)

MW (calculated): 4866.6 Da

Synthesis and purification methods: 501; P02

LCMS: 010_CA07; Rt: 10.14 min; m/3: 1623.2 m/4: 1216.9 m/5:

Compound 110

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,18Q,22V,23E,28Y,30W,31L]-hPYY(4-36)

iVal-APEK(C18DA-gGlu-Ahx)PEEDAT-PEELQRYYVELRHYYNWLTRQRY-NH2 (SEQ ID NO: 114)

MW (calculated): 4866.5 Da

Synthesis and purification methods: S01; P02

LCMS: 010_CA07; Rt: 10.31 min; m/3: 1622.9 m/4: m/5:

Compound 111

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,10A,11A,13E,17I,18Q,22V,28Y,30W,31L]-hPYY(4-36)

iVal-APAK(C18DA-gGlu-Ahx)PEAAAEPEE-IQRYYVSLRHYYNWLTRQRY-NH2 (SEQ ID NO: 115)

MW (calculated): 4692.4 Da

Synthesis and purification methods: S01; P02

LCMS: 010_CA07; Rt: 11.12 min; m/3: 1564.1 m/4: 1173.3 m/5:

Compound 112

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13E,17I,18Q,22V,28Y,30W,31L]-hPYY(4-36)

iVal-APEK(C18DA-gGlu-Ahx)PEEDAEPEE-IQRYYVSLRHYYNWLTRQRY-NH2 (SEQ ID NO: 116)

MW (calculated): 4852.5 Da

Synthesis and purification methods: S01; P02

LCMS: 010_CA07; Rt: 9.97 min; m/3: m/4: 1214.4 m/5:

Compound 113

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,17I,18Q,22V,28Q,30W,31L]-hPYY(4-36)

iVal-APEK(C18DA-gGlu-Ahx)PEEDATPEE-IQRYYVSLRHYQNWLTRQRY-NH2 (SEQ ID NO: 117)

MW (calculated): 4789.4 Da

Synthesis and purification methods: S01; P01

LCMS: 010_CA07; Rt: 9.23 min; m/3: 1596.7 m/4: m/5:

Compound 114

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,13T,17I,18Q,22V,28Y,30W,31L]-hPYY(4-36)

iVal-APAK(C18DA-gGlu-Ahx)PEEDATPEE-IQRYYVSLRHYYNWLTRQRY-NH2 (SEQ ID NO: 118)

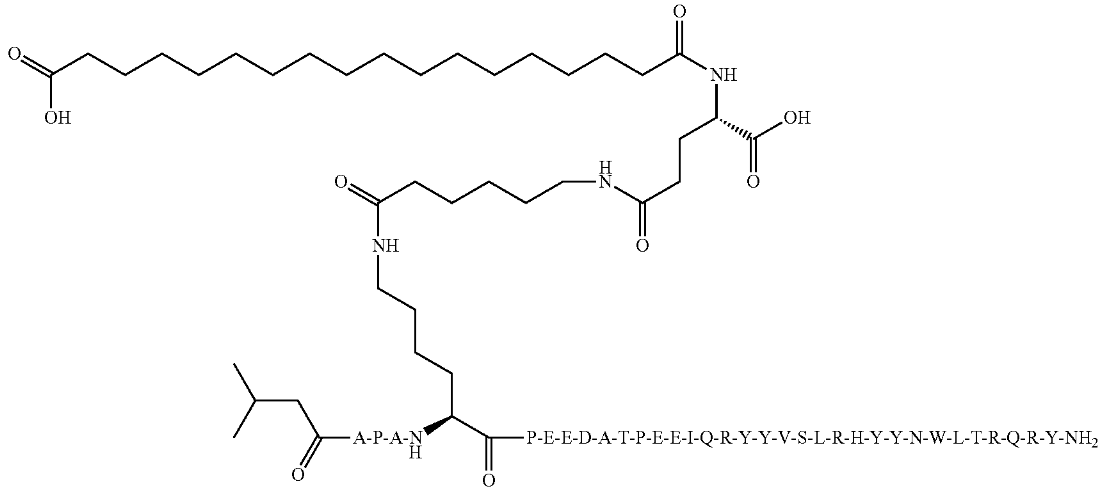

MW (calculated): 4766.4 Da

Synthesis and purification methods: S01; P01

LCMS: 010_CA07; Rt: 11.70 min; m/3: m/4: 1192.4 m/5:

Compound 115

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,18Q,21Q,22V,28Y,30W,31L]-hPYY(4-36)

iVal-APEK(C18DA-gGlu-Ahx)PEEDAT-PEELQRYQVSLRHYYNWLTRQRY-NH2 (SEQ ID NO: 119)

MW (calculated): 4789.4 Da

Synthesis and purification methods: S01; P01

LCMS: 010_CA07; Rt: 11.17 min; m/3: 1597.3 m/4: m/5:

Compound 116

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,10A,11A,13E,17I,18Q,22V,23A,28Y,30W,31L]-hPYY(4-36)

iVal-APAK(C18DA-gGlu-Ahx)PEAAAEPEEIQRYY-VALRHYYNWLTRQRY-NH2 (SEQ ID NO: 120)

MW (calculated): 4676.4 Da

Synthesis and purification methods: S01; P02

LCMS: 010_CA07; Rt: 11.62 min; m/3: 1559.2 m/4: m/5:

Compound 117

N{alpha-4}-(3-methylbutanoyl)-N{epsilon-7}-(6-[(4S)-4-carboxy-4-(17-carboxyheptadecanamido) butanamido] hexanoyl)-[4A,7K,9E,17A,18Q,22V,23A,28Y,30W,31L]-hPYY(4-36)

iVal-APEK(C18DA-gGlu-Ahx)PEEDASPEEAQRYY-VALRHYYNWLTRQRY-NH2 (SEQ ID NO: 121)

MW (calculated): 4752.4 Da

Synthesis and purification methods: S01; P01

LCMS: 010_CA07; Rt: 12.53 min; m/3: 1584.9 m/4: m/5:

Compound 118

N{alpha-4}-(3-methylbutanoyl)-N{epsilon-7}-(6-[(4S)-4-carboxy-4-(17-carboxyheptadecanamido) butanamido] hexanoyl)-[4A,7K,9P,13E,17I,18Q,22V,28Y,30W,31L]-hPYY(4-36)

iVal-APEK(C18DA-gGlu-Ahx)PPEDAEPEE-IQRYYVSLRHYYNWLTRQRY-NH2 (SEQ ID NO: 122)

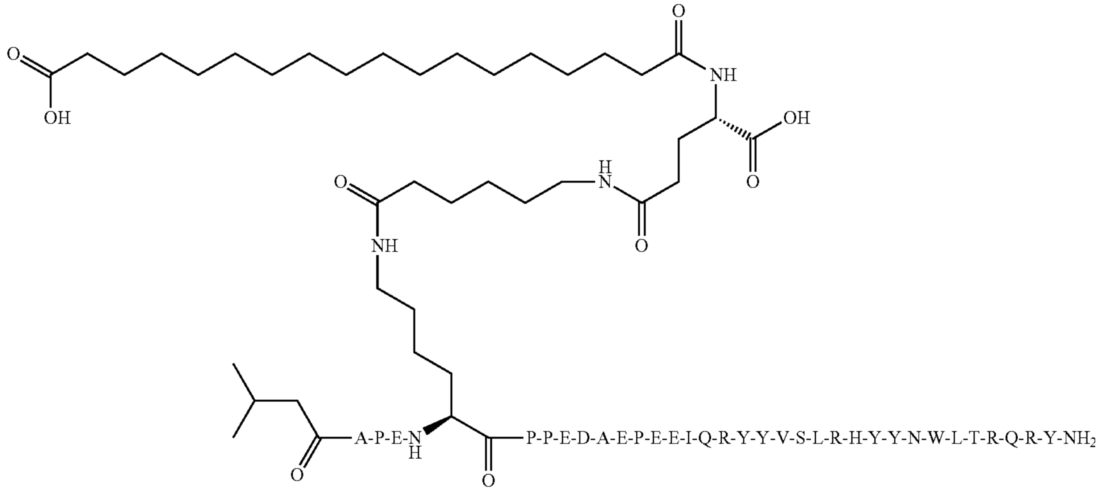

MW (calculated): 4820.5 Da

Synthesis and purification methods: S01; P02

LCMS: 010_CA07; Rt: 9.86 min; m/3: 1607.4 m/4: m/5:

Compound 119

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,17S,18Q,22V,28Y,30W,31L]-hPYY(4-36)

iVal-APEK(C18DA-gGlu-Ahx)PEEDAT-PEESQRYYVSLRHYYNWLTRQRY-NH2 (SEQ ID NO: 123)

MW (calculated): 4798.4 Da

Synthesis and purification methods: S01; P01

LCMS: 010_CA07; Rt: 10.92 min; m/3: 1600.3 m/4: m/5:

Compound 120

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,11A,13T,17I,18Q,22V,23A,28Y,30W,31L]-hPYY(4-36)

iVal-APAK(C18DA-gGlu-Ahx)PEEAATPEEIQRYY-VALRHYYNWLTRQRY-NH2 (SEQ ID NO: 124)

MW (calculated): 4706.4 Da

Synthesis and purification methods: S01; P02

LCMS: 010_CA07; Rt: 11.28 min; m/3: m/4: 1177.1 m/5:

Compound 121

N{alpha-4}-(3-methylbutanoyl)-N{epsilon-7}-(6-[(4S)-4-carboxy-4-(17-carboxyheptadecanamido) butanamido] hexanoyl)-[4A,7K,9E,10A,18Q,22V,23Q,28Y,30W,31L]-hPYY(4-36)

iVal-APEK(C18DA-gGlu-Ahx) PEADASPEELQRYYVQLRHYYNWLTRQRY-NH2 (SEQ ID NO: 125)

MW (calculated): 4793.5 Da

Synthesis and purification methods: 501; P02

LCMS: 010_CA07; Rt: 9.78 min; m/3: m/4: 1199.3 m/5:

Compound 122

N{alpha-4}-(3-methylbutanoyl)-N{epsilon-7}-(6-[(4S)-4-carboxy-4-(17-carboxyheptadecanamido) butanamido] hexanoyl)-[4A,7K,9E,10A,11E,18Q,22V,28Y,30W,31L]-hPYY(4-36)

iVal-APEK(C18DA-gGlu-Ahx)PE-AEASPEELQRYYVSLRHYYNWLTRQRY-NH2 (SEQ ID NO: 126)

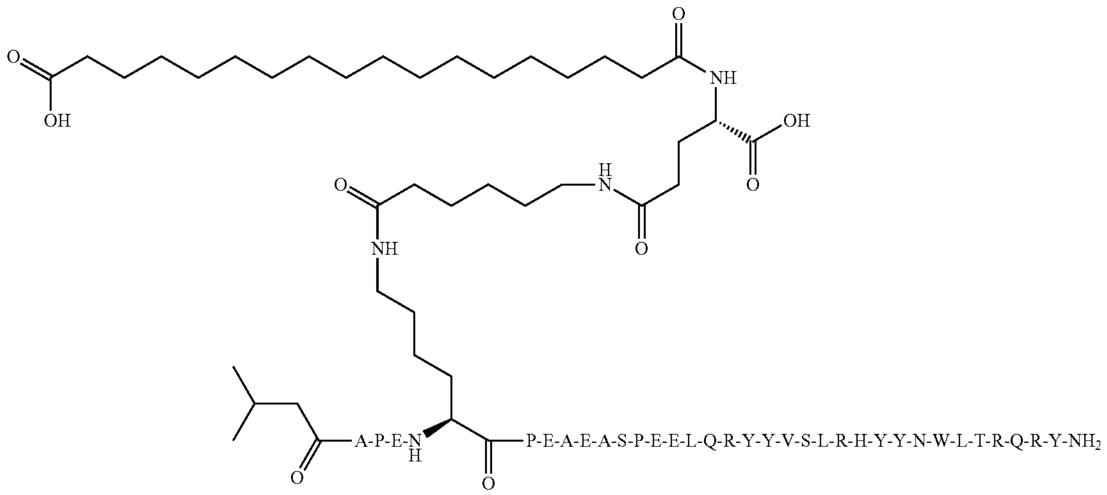

MW (calculated): 4766.4 Da
Synthesis and purification methods: S01; P01
LCMS: 010_CA07; Rt: 12.40 min; m/3: 1589.2 m/4: m/5:

Compound 123
N{alpha-4}-(3-methylbutanoyl)-N{epsilon-7}-(6-[(4S)-4-carboxy-4-(17-carboxyheptadecanamido) butanamido] hexanoyl)-[4A,7K,9E,13A,18Q,19K,22V,28Y,30W,31L]-hPYY(4-36)
iVal-APEK(C18DA-gGlu-Ahx)PEEDAAP-EELQKYYVSLRHYYNWLTRQRY-NH2 (SEQ ID NO: 127)
MW (calculated): 4766.4 Da
Synthesis and purification methods: S01; P02
LCMS: 010_CA07; Rt: 10.65 min; m/3: m/4: 1192.1 m/5:

Compound 124
N{alpha-4}-(3-methylbutanoyl)-N{epsilon-7}-(6-[(4S)-4-carboxy-4-(17-carboxyheptadecanamido) butanamido] hexanoyl)-[4A,7K,9E,10A,11A,13E,17I,18Q,22V,28Y,30W,31L]-hPYY(4-36)
iVal-APEK(C18DA-gGlu-Ahx)PEAAAEPEE-IQRYYVSLRHYYNWLTRQRY-NH2 (SEQ ID NO: 128)
MW (calculated): 4750.4 Da
Synthesis and purification methods: S01; P02
LCMS: 010_CA07; Rt: 10.74 min; m/3: 1583.7 m/4: m/5:

Compound 125
N{alpha-4}-(3-methylbutanoyl)-N{epsilon-7}-(6-[(4S)-4-carboxy-4-(17-carboxyheptadecanamido) butanamido] hexanoyl)-[4A,7K,9E,18Q,22V,23E,28Y,30W,31L]-hPYY(4-36)
iVal-APEK(C18DA-gGlu-Ahx)PEE-DASPEELQRYYVELRHYYNWLTRQRY-NH2 (SEQ ID NO: 129)
MW (calculated): 4852.5 Da
Synthesis and purification methods: S01; P01
LCMS: 010_CA07; Rt: 9.93 min; m/3: 1618.3 m/4: m/5:

Compound 126
N{alpha-4}-(3-methylbutanoyl)-N{epsilon-7}-(6-[(4S)-4-carboxy-4-(17-carboxyheptadecanamido) butanamido] hexanoyl)-[4A,7K,9E,13E,18Q,22V,28Y,30W,31L]-hPYY(4-36)
iVal-APEK(C18DA-gGlu-Ahx)PEEDAE-PEELQRYYVSLRHYYNWLTRQRY-NH2 (SEQ ID NO: 130)
MW (calculated): 4852.5 Da
Synthesis and purification methods: S01; P01
LCMS: 010_CA07; Rt: 12.00 min; m/3: 1617.0 m/4: m/5:

Compound 127
N{alpha-4}-(3-methylbutanoyl)-N{epsilon-7}-(6-[(4S)-4-carboxy-4-(17-carboxyheptadecanamido) butanamido] hexanoyl)-[4A,7K,9E,10A,11A,13E,18Q,22V,23A,28Y,30W,31L]-hPYY(4-36)
iVal-APEK(C18DA-gGlu-Ahx)PEAAAEPEELQRYY-VALRHYYNWLTRQRY-NH2 (SEQ ID NO: 131)
MW (calculated): 4734.4 Da
Synthesis and purification methods: 501; P02
LCMS: 010_CA07; Rt: 10.99 min; m/3: m/4: 1184.2 m/5:

Compound 128
N{alpha-4}-(3-methylbutanoyl)-N{epsilon-7}-(6-[(4S)-4-carboxy-4-(17-carboxyheptadecanamido) butanamido] hexanoyl)-[4A,7K,9E,11A,13T,18Q,22V,28Y,30W,31L]-hPYY(4-36)
iVal-APEK(C18DA-gGlu-Ahx)PEEAAT-PEELQRYYVSLRHYYNWLTRQRY-NH2 (SEQ ID NO: 132)
MW (calculated): 4780.5 Da
Synthesis and purification methods: S01; P01
LCMS: 010_CA07; Rt: 13.70 min; m/3: 1594.6 m/4: m/5:

Compound 129
N{alpha-4}-(3-methylbutanoyl)-N{epsilon-7}-(6-[(4S)-4-carboxy-4-(17-carboxyheptadecanamido) butanamido] hexanoyl)-[4A,7K,9E,14A,17I,18Q,22V,28Y,30W,31L]-hPYY(4-36)
iVal-APEK(C18DA-gGlu-Ahx)PEEDASAEE-IQRYYVSLRHYYNWLTRQRY-NH2 (SEQ ID NO: 133)
MW (calculated): 4784.4 Da
Synthesis and purification methods: S01; P02
LCMS: 010_CA07; Rt: 10.37 min; m/3: m/4: 1197.0 m/5:

Compound 130
N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,18Q,19L,22V,28Y,30W,31L]-hPYY(4-36)
iVal-APEK(C18DA-gGlu-Ahx)PEEDAT-PEELQLYYVSLRHYYNWLTRQRY-NH2 (SEQ ID NO: 134)
MW (calculated): 4781.5 Da
Synthesis and purification methods: S01; P01
LCMS: 010_CA07; Rt: 10.67 min; m/3: 1595.1 m/4: m/5:

Compound 131
N{alpha-4}-(3-methylbutanoyl)-N{epsilon-7}-(6-[(4S)-4-carboxy-4-(17-carboxyheptadecanamido) butanamido] hexanoyl)-[4A,7K,9E,10A,13E,17I,18Q,22V,23A,28Y,30W,31L]-hPYY(4-36)
iVal-APEK(C18DA-gGlu-Ahx)PEADAEPEEIQRYY-VALRHYYNWLTRQRY-NH2 (SEQ ID NO: 135)
MW (calculated): 4778.5 Da
Synthesis and purification methods: S01; P02
LCMS: 010_CA07; Rt: 10.83 min; m/3: m/4: 1195.0 m/5:

Compound 132
N{alpha-4}-(3-methylbutanoyl)-N{epsilon-7}-(6-[(4S)-4-carboxy-4-(17-carboxyheptadecanamido) butanamido] hexanoyl)-[4A,7K,9E,10A,13T,18Q,22V,28Y,30W,31L]-hPYY(4-36)
iVal-APEK(C18DA-gGlu-Ahx)PEADAT-PEELQRYYVSLRHYYNWLTRQRY-NH2 (SEQ ID NO: 136)
MW (calculated): 4766.4 Da
Synthesis and purification methods: S01; P02
LCMS: 010_CA07; Rt: 9.74 min; m/3: 1589.6 m/4: m/5:

Compound 133
N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,13E,18Q,22V,28Y,30W,31L]-hPYY(4-36)
iVal-APAK(C18DA-gGlu-Ahx)PEEDAE-PEELQRYYVSLRHYYNWLTRQRY-NH2 (SEQ ID NO: 137)
MW (calculated): 4794.5 Da
Synthesis and purification methods: 501; P02
LCMS: 010_CA07; Rt: 10.12 min; m/3: 1598.3 m/4: m/5:

Compound 134
N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,17Q,18Q,22V,28Y,30W,31L]-hPYY(4-36)
iVal-APEK(C18DA-gGlu-Ahx)PEEDATPE-EQQRYYVSLRHYYNWLTRQRY-NH2 (SEQ ID NO: 138)
MW (calculated): 4839.5 Da
Synthesis and purification methods: S01; P01
LCMS: 010_CA07; Rt: 9.04 min; m/3: 1613.8 m/4: m/5:

Compound 135

N{alpha-4}-(3-methylbutanoyl)-N{epsilon-7}-(6-[(4S)-4-carboxy-4-(17-carboxyheptadecanamido) butanamido] hexanoyl)-[4A,7K,9E,10A,11A,13E,17I,18Q,22V,23A,28Y,30W,31L]-hPYY(4-36)

iVal-APEK(C18DA-gGlu-Ahx)PEAAAEPEEIQRYY-VALRHYYNWLTRQRY-NH2 (SEQ ID NO: 139)

MW (calculated): 4734.4 Da

Synthesis and purification methods: S01; P02

LCMS: 010_CA07; Rt: 11.45 min; m/3: m/4: 1184.2 m/5:

Compound 136

N{alpha-4}-(3-methylbutanoyl)-N{epsilon-7}-(6-[(4S)-4-carboxy-4-(17-carboxyheptadecanamido) butanamido] hexanoyl)-[4A,7K,9E,10A,13T,18Q,22V,23A,28Y,30W,31L]-hPYY(4-36)

iVal-APEK(C18DA-gGlu-Ahx)PEADATPEELQRYY-VALRHYYNWLTRQRY-NH2 (SEQ ID NO: 140)

Compound 139

N{alpha-4}-(3-methylbutanoyl)-N{epsilon-7}-(6-[(4S)-4-carboxy-4-(17-carboxyheptadecanamido) butanamido] hexanoyl)-[4A,7K,9E,11E,15A,18Q,22V,28Y,30W,31L]-hPYY(4-36)

iVal-APEK(C18DA-gGlu-Ahx)PEEEASPAEL-QRYYVSLRHYYNWLTRQRY-NH2 (SEQ ID NO: 143)

MW (calculated): 4766.4 Da

Synthesis and purification methods: S01; P02

LCMS: 010_CA07; Rt: 10.01 min; m/3: 1589.4 m/4: 1191.8 m/5:

Compound 140

N{alpha-4}-(3-methylbutanoyl)-N{epsilon-7}-(6-[(4S)-4-carboxy-4-(17-carboxyheptadecanamido) butanamido] hexanoyl)-[4A,7K,9E,10A,17I,18Q,22V,28Y,30W,31L]-hPYY(4-36)

iVal-APEK(C18DA-gGlu-Ahx)PEADASPEE-IQRYYVSLRHYYNWLTRQRY-NH2 (SEQ ID NO: 144)

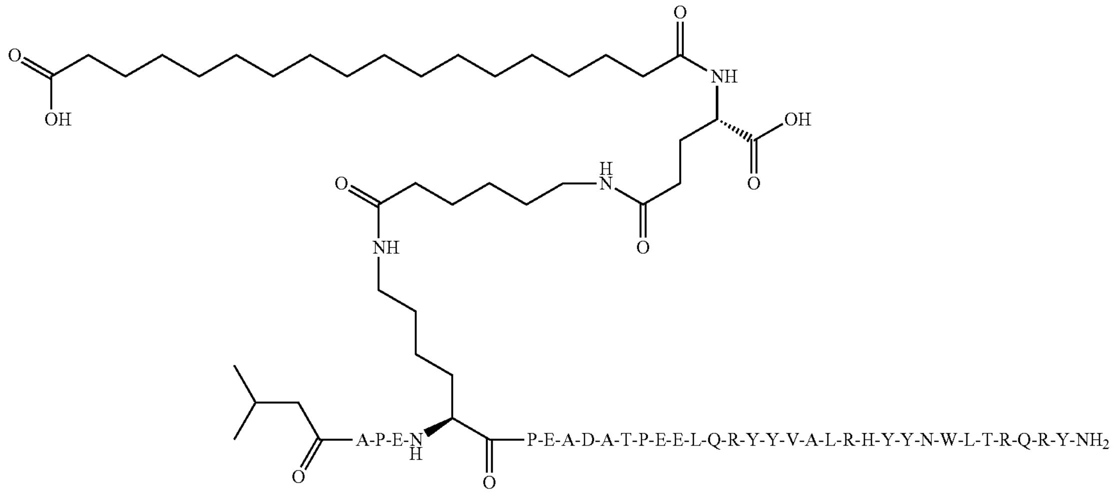

MW (calculated): 4750.4 Da

Synthesis and purification methods: 501; P01

LCMS: 010_CA07; Rt: 13.80 min; m/3: 1584.4 m/4: m/5:

Compound 137

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,18Q,22V,28Y,30W,31L,32L]-hPYY(4-36)

iVal-APEK(C18DA-gGlu-Ahx)PEEDAT-PEELQRYYVSLRHYYNWLLRQRY-NH2 (SEQ ID NO: 141)

MW (calculated): 4836.5 Da

Synthesis and purification methods: S01; P01

LCMS: 010_CA07; Rt: 11.13 min; m/3: 1558.4 m/4: m/5:

Compound 138

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13E,18Q,19E,22V,28Y,30W,31L]-hPYY(4-36)

iVal-APEK(C18DA-gGlu-Ahx)PEEDAE-PEELQEYYVSLRHYYNWLTRQRY-NH2 (SEQ ID NO: 142)

MW (calculated): 4825.4 Da

Synthesis and purification methods: S01; P02

LCMS: 010_CA07; Rt: 13.90 min; m/3: 1609.1 m/4: 1206.7 m/5:

MW (calculated): 4752.4 Da

Synthesis and purification methods: S01; P01

LCMS: 010_CA07; Rt: 10.21 min; m/3: 1585.1 m/4: m/5:

Compound 141

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,18Q,19S,22V,28Y,30W,31L]-hPYY(4-36)

iVal-APEK(C18DA-gGlu-Ahx)PEEDAT-PEELQSYYVSLRHYYNWLTRQRY-NH2 (SEQ ID NO: 145)

MW (calculated): 4755.4 Da

Synthesis and purification methods: S01; P01

LCMS: 010_CA07; Rt: 10.40 min; m/3: 1586.6 m/4: m/5:

Compound 142

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13L,17I,18Q,22V,28Y,30W,31L]-hPYY(4-36)

iVal-APEK(C18DA-gGlu-Ahx)PEEDALPEE-IQRYYVSLRHYYNWLTRQRY-NH2 (SEQ ID NO: 146)

MW (calculated): 4836.5 Da

Synthesis and purification methods: 501; P02

LCMS: 010_CA07; Rt: 12.05 min; m/3: 1613.6 m/4: 1210.2 m/5:

Compound 143

N{alpha-4}-(3-methylbutanoyl)-N{epsilon-7}-(6-[(4S)-4-carboxy-4-(17-carboxyheptadecanamido) butanamido] hexanoyl)-[4A,7K,9E,12S,13T,18Q,22V,28Y,30W,31L]-hPYY(4-36)

iVal-APEK(C18DA-gGlu-Ahx)PEEDST-PEELQRYYVSLRHYYNWLTRQRY-NH2 (SEQ ID NO: 147)

MW (calculated): 4840.5 Da

Synthesis and purification methods: S01; P01

LCMS: 010_CA07; Rt: 11.81 min; m/3: 1614.3 m/4: m/5:

Compound 144

N{alpha-4}-(3-methylbutanoyl)-N{epsilon-7}-(6-[(4S)-4-carboxy-4-(17-carboxyheptadecanamido) butanamido] hexanoyl)-[4A,7K,9E,12Q,13T,18Q,22V,28Y,30W,31L]-hPYY(4-36)

iVal-APEK(C18DA-gGlu-Ahx)PEEDQT-PEELQRYYVSLRHYYNWLTRQRY-NH2 (SEQ ID NO: 148)

MW (calculated): 4881.5 Da

Synthesis and purification methods: S01; P02

LCMS: 010_CA07; Rt: 9.95 min; m/3: 1628.4 m/4: 1221.3 m/5:

Compound 145

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,18Q,22V,28Y,30W,31L]-hPYY (4-36)

iVal-APAK(C18DA-gGlu-Ahx)PEE-DASPEELQRYYVSLRHYYNWLTRQRY-NH2 (SEQ ID NO: 149)

MW (calculated): 4752.4 Da

Synthesis and purification methods: S01; P02

LCMS: 010_CA07; Rt: 10.37 min; m/3: 1586.0 m/4: m/5:

Compound 146

N{alpha-4}-(3-methylbutanoyl)-N{epsilon-7}-(6-[(4S)-4-carboxy-4-(17-carboxyheptadecanamido) butanamido] hexanoyl)-[4A,7K,9E,11E,13T,18Q,22V,28Y,30W,31L]-hPYY(4-36)

iVal-APEK(C18DA-gGlu-Ahx)PEEEAT-PEELQRYYVSLRHYYNWLTRQRY-NH2 (SEQ ID NO: 150)

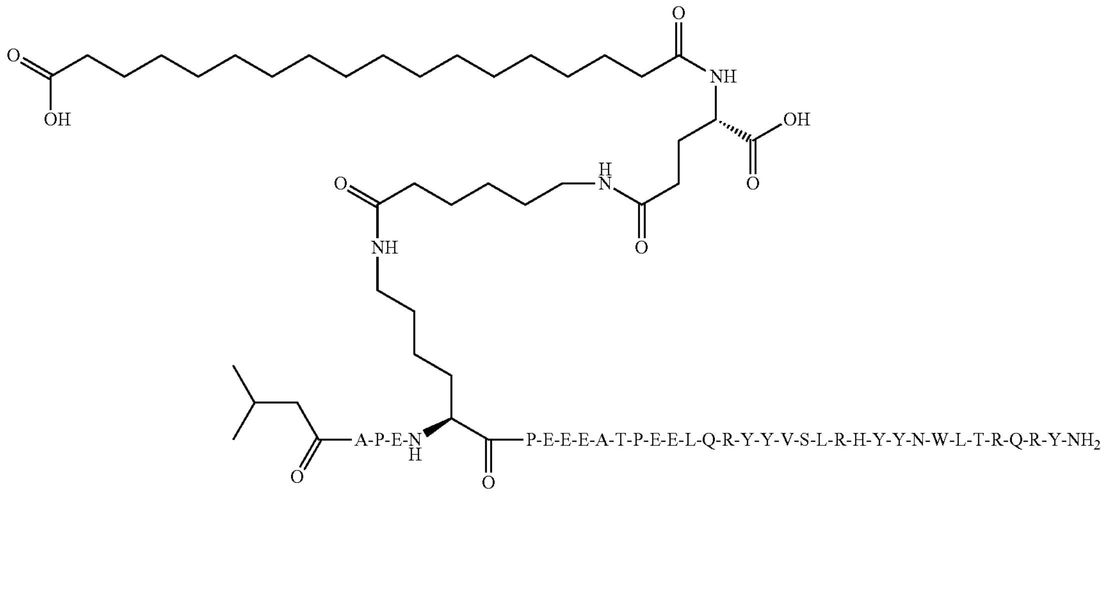

MW (calculated): 4838.5 Da

Synthesis and purification methods: S01; P01

LCMS: 010_CA07; Rt: 10.57 min; m/3: 1614.2 m/4: m/5:

Compound 147

N{alpha-4}-(3-methylbutanoyl)-N{epsilon-7}-(6-[(4S)-4-carboxy-4-(17-carboxyheptadecanamido) butanamido] hexanoyl)-[4A,7K,9E,17I,18Q,22V,28Y,30W,31L]-hPYY (4-36)

iVal-APEK(C18DA-gGlu-Ahx)PEEDASPEE-IQRYYVSLRHYYNWLTRQRY-NH2 (SEQ ID NO: 151)

MW (calculated): 4810.5 Da

Synthesis and purification methods: S01; P01

LCMS: 010_CA07; Rt: 10.02 min; m/3: 1603.9 m/4: m/5:

Compound 148

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,18Q,22V,23T,28Y,30W,31L]-hPYY(4-36)

iVal-APEK(C18DA-gGlu-Ahx)PEEDAT-PEELQRYYVTLRHYYNWLTRQRY-NH2 (SEQ ID NO: 152)

MW (calculated): 4838.5 Da

Synthesis and purification methods: S01; P01

LCMS: 010_CA07; Rt: 11.80 min; m/3: m/4: 1210.5 m/5:

Compound 149

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,17S,18Q,22V,28Y,30W,31L]-hPYY(4-36)

iVal-APAK(C18DA-gGlu-Ahx)PEE-DASPEESQRYYVSLRHYYNWLTRQRY-NH2 (SEQ ID NO: 153)

MW (calculated): 4726.3 Da

Synthesis and purification methods: S01; P02

LCMS: 010_CA07; Rt: 9.28 min; m/3: m/4: 1182.3 m/5:

Compound 150

N{alpha-4}-(3-methylbutanoyl)-N{epsilon-7}-(6-[(4S)-4-carboxy-4-(17-carboxyheptadecanamido) butanamido] hexanoyl)-[4A,7K,9E,11A,17I,18Q,22V,28Y,30W,31L]-hPYY(4-36)

iVal-APEK(C18DA-gGlu-Ahx)PEEAASPEE-IQRYYVSLRHYYNWLTRQRY-NH2 (SEQ ID NO: 154)

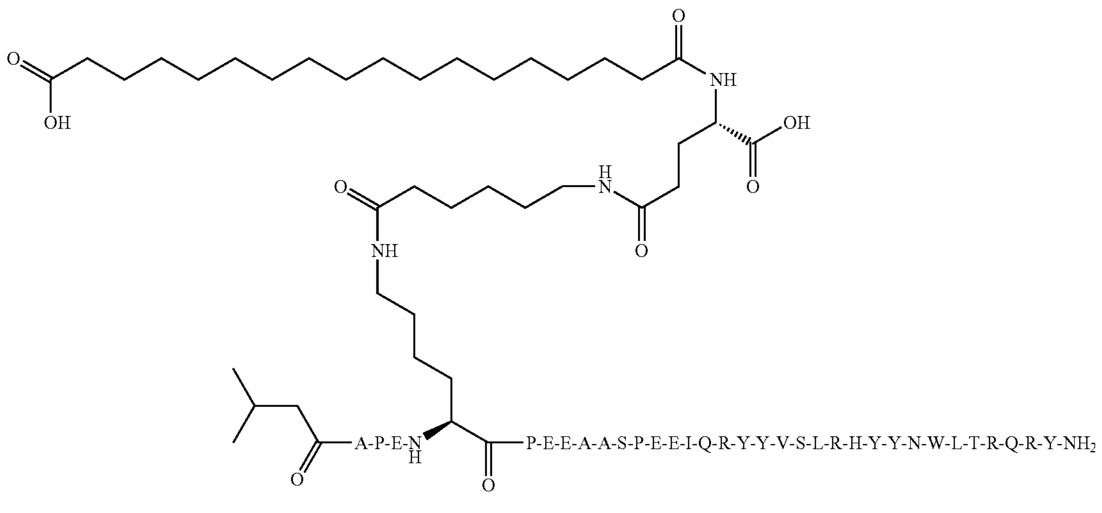

MW (calculated): 4766.4 Da

Synthesis and purification methods: S01; P01

LCMS: 010_CA07; Rt: 12.30 min; m/3: 1590.6 m/4: m/5:

Compound 151

N{alpha-4}-(3-methylbutanoyl)-N{epsilon-7}-(6-[(4S)-4-carboxy-4-(17-carboxyheptadecanamido) butanamido] hexanoyl)-[4A,7K,9E,12S,18Q,22V,23A,28Y,30W,31L]-hPYY(4-36)

iVal-APEK(C18DA-gGlu-Ahx)PEEDSSPEELQRYY-VALRHYYNWLTRQRY-NH2 (SEQ ID NO: 155)

MW (calculated): 4810.5 Da

Synthesis and purification methods: S01; P01

LCMS: 010_CA07; Rt: 10.05 min; m/3: 1603.5 m/4: m/5:

Compound 152

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,17T,18Q,22V,28Y,30W,31L]-hPYY(4-36)

iVal-APEK(C18DA-gGlu-Ahx)PEEDAT-PEETQRYYVSLRHYYNWLTRQRY-NH2 (SEQ ID NO: 156)

MW (calculated): 4812.4 Da

Synthesis and purification methods: S01; P01

LCMS: 010_CA07; Rt: 10.96 min; m/3: m/4: 1204.0 m/5:

Compound 153

N{alpha-4}-(3-methylbutanoyl)-N{epsilon-7}-(6-[(4S)-4-carboxy-4-(17-carboxyheptadecanamido) butanamido] hexanoyl)-[4A,7K,9E,11L,13T,18Q,22V,28Y,30W,31L]-hPYY(4-36)

iVal-APEK(C18DA-gGlu-Ahx)PEELAT-PEELQRYYVSLRHYYNWLTRQRY-NH2 (SEQ ID NO: 157)

MW (calculated): 4822.6 Da

Synthesis and purification methods: S01; P01

LCMS: 010_CA07; Rt: 10.90 min; m/3: m/4: 1206.5 m/5:

Compound 154

N{alpha-4}-(3-methylbutanoyl)-N{epsilon-7}-(6-[(4S)-4-carboxy-4-(17-carboxyheptadecanamido) butanamido] hexanoyl)-[4A,7K,9E,11A,13T,17I,18Q,22V,23A,28Y,30W,31L]-hPYY(4-36)

iVal-APEK(C18DA-gGlu-Ahx)PEEAATPEEIQRYY-VALRHYYNWLTRQRY-NH2 (SEQ ID NO: 158)

MW (calculated): 4764.5 Da

Synthesis and purification methods: S01; P02

LCMS: 010_CA07; Rt: 10.68 min; m/3: 1588.4 m/4: m/5:

Compound 155

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,18Q,22V,28Y,30W,31L,32S]-hPYY(4-36)

iVal-APEK(C18DA-gGlu-Ahx)PEEDAT-PEELQRYYVSLRHYYNWLSRQRY-NH2 (SEQ ID NO: 159)

MW (calculated): 4810.5 Da

Synthesis and purification methods: S01; P01

LCMS: 010_CA07; Rt: 11.33 min; m/3: 1604.2 m/4: m/5:

Compound 156

N{alpha-4}-(3-methylbutanoyl)-N{epsilon-7}-(6-[(4S)-4-carboxy-4-(17-carboxyheptadecanamido) butanamido] hexanoyl)-[4A,7K,9E,11A,13E,17I,18Q,22V,23A,28Y,30W,31L]-hPYY(4-36)

iVal-APEK(C18DA-gGlu-Ahx)PEEAAEPEEIQRYY-VALRHYYNWLTRQRY-NH2 (SEQ ID NO: 160)

MW (calculated): 4792.5 Da

Synthesis and purification methods: S01; P02

LCMS: 010_CA07; Rt: 10.99 min; m/3: 1598.2 m/4: 1199.1 m/5:

Compound 157

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,11A,18Q,22V,23A,28Y,30W,31L]-hPYY(4-36)

iVal-APAK(C18DA-gGlu-Ahx)PEEAASPEELQRYY-VALRHYYNWLTRQRY-NH2 (SEQ ID NO: 161)

MW (calculated): 4692.4 Da

Synthesis and purification methods: S01; P01

LCMS: 010_CA07; Rt: 13.45 min; m/3: 1564.3 m/4: m/5:

Compound 158

N{alpha-4}-(3-methylbutanoyl)-N{epsilon-7}-(6-[(4S)-4-carboxy-4-(17-carboxyheptadecanamido) butanamido] hexanoyl)-[4A,7K,9P,11A,17I,18Q,22V,23A,28Y,30W,31L]-hPYY(4-36)

iVal-APEK(C18DA-gGlu-Ahx)PPEAASPEEIQRYY-VALRHYYNWLTRQRY-NH2 (SEQ ID NO: 162)

MW (calculated): 4718.4 Da

Synthesis and purification methods: S01; P01

LCMS: 010_CA07; Rt: 13.11 min; m/3: 1574.2 m/4: m/5:

Compound 159

N{alpha-4}-(3-methylbutanoyl)-N{epsilon-7}-(6-[(4S)-4-carboxy-4-(17-carboxyheptadecanamido) butanamido] hexanoyl)-[4A,7K,9E,10A,13E,18Q,22I,28Y,30W,31L]-hPYY(4-36)

iVal-APEK(C18DA-gGlu-Ahx)PEADAEPEELQRYY-ISLRHYYNWLTRQRY-NH2 (SEQ ID NO: 163)

MW (calculated): 4808.5 Da

Synthesis and purification methods: S01; P02

LCMS: 010_CA07; Rt: 10.63 min; m/3: m/4: 1203.2 m/5:

Compound 160

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,18Q,22I,23A,28Y,30W,31L]-hPYY(4-36)

iVal-APAK(C18DA-gGlu-Ahx)PEE-DASPEELQRYYIALRHYYNWLTRQRY-NH2 (SEQ ID NO: 164)

MW (calculated): 4750.4 Da

Synthesis and purification methods: 501; P02

LCMS: 010_CA07; Rt: 13.49 min; m/3: m/4: 1188.2 m/5:

Compound 161

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,11A,13E,18Q,22V,23A,28Y,30W,31L]-hPYY(4-36)

iVal-APAK(C18DA-gGlu-Ahx)PEEAAEPEELQRYY-VALRHYYNWLTRQRY-NH2 (SEQ ID NO: 165)

MW (calculated): 4734.4 Da

Synthesis and purification methods: S01; P02

LCMS: 010_CA07; Rt: 11.00 min; m/3: m/4: 1184.0 m/5:

Compound 162

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,17E,18Q,22V,28Y,30W,31L]-hPYY(4-36)

iVal-APEK(C18DA-gGlu-Ahx)PEEDATPEE-EQRYYVSLRHYYNWLTRQRY-NH2 (SEQ ID NO: 166)

MW (calculated): 4840.4 Da

Synthesis and purification methods: S01; P02

LCMS: 010_CA07; Rt: 9.20 min; m/3: m/4: 1211.0 m/5:

Compound 163

N{alpha-4}-(3-methylbutanoyl)-N{epsilon-7}-(6-[(4S)-4-carboxy-4-(17-carboxyheptadecanamido) butanamido] hexanoyl)-[4A,7K,9E,10A,18Q,22V,23A,28Y,30W,31L]-hPYY(4-36)

iVal-APEK(C18DA-gGlu-Ahx)PEADASPEELQRYY-VALRHYYNWLTRQRY-NH2 (SEQ ID NO: 167)

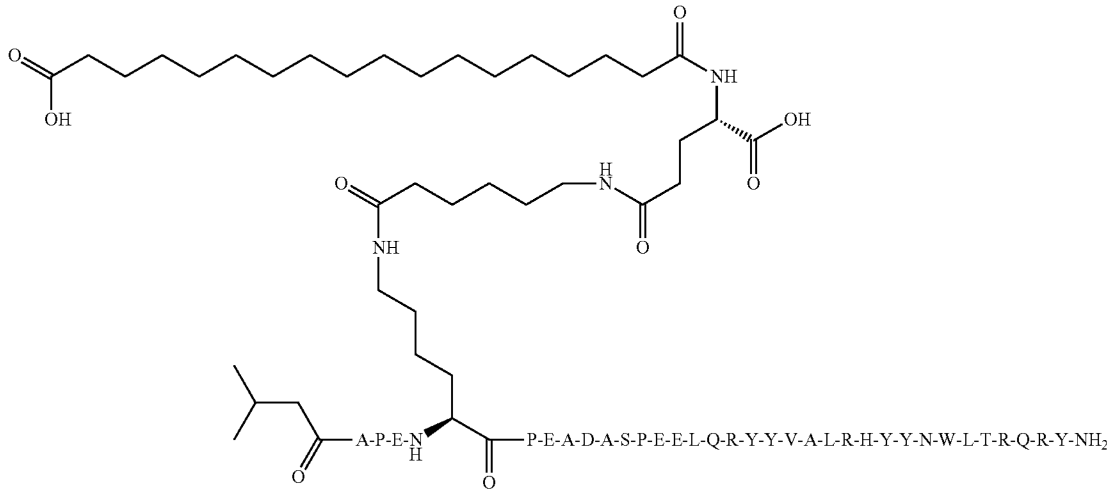

MW (calculated): 4736.4 Da

Synthesis and purification methods: 501; P01

LCMS: 010_CA07; Rt: 12.30 min; m/3: m/4: 1184.5 m/5:

Compound 164

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,17I,18Q,22Q,28Y,30W,31L]-hPYY(4-36)

iVal-APEK(C18DA-gGlu-Ahx)PEEDATPEE-IQRYYQSLRHYYNWLTRQRY-NH2 (SEQ ID NO: 168)

MW (calculated): 4853.5 Da

Synthesis and purification methods: S01; P01

LCMS: 010_CA07; Rt: 11.44 min; m/3: 1618.6 m/4: m/5:

Compound 165

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9P,13E,18Q,22V,28Y,30W,31L]-hPYY(4-36)

iVal-APAK(C18DA-gGlu-Ahx)PPEDAE-PEELQRYYVSLRHYYNWLTRQRY-NH2 (SEQ ID NO: 169)

MW (calculated): 4762.5 Da

Synthesis and purification methods: S01; P01

LCMS: 010_CA07; Rt: 10.11 min; m/3: 1587.7 m/4: m/5:

Compound 166

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,18Q,22V,23E,28Y,30W,31L]-hPYY(4-36)

iVal-APAK(C18DA-gGlu-Ahx)PEE-DASPEELQRYYVELRHYYNWLTRQRY-NH2 (SEQ ID NO: 170)

MW (calculated): 4794.5 Da

Synthesis and purification methods: S01; P02

LCMS: 010_CA07; Rt: 9.76 min; m/3: m/4: 1199.2 m/5:

Compound 167

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,11A,13E,17I,18Q,22V,23A,28Y,30W,31L]-hPYY(4-36)

iVal-APAK(C18DA-gGlu-Ahx)PEEAAEPEEIQRYY-VALRHYYNWLTRQRY-NH2 (SEQ ID NO: 171)

MW (calculated): 4734.4 Da

Synthesis and purification methods: S01; P02

LCMS: 010_CA07; Rt: 11.49 min; m/3: m/4: 1185.0 m/5:

Compound 168

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,17I,18Q,22S,28Y,30W,31L]-hPYY(4-36)

iVal-APEK(C18DA-gGlu-Ahx)PEEDATPEE-IQRYYSSLRHYYNWLTRQRY-NH2 (SEQ ID NO: 172)

MW (calculated): 4812.4 Da

Synthesis and purification methods: S01; P01

LCMS: 010_CA07; Rt: 9.83 min; m/3: 1605.7 m/4: m/5:

Compound 169

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13E,18Q,19A,22V,28Y,30W,31L]-hPYY(4-36)

iVal-APEK(C18DA-gGlu-Ahx)PEEDAE-PEELQAYYVSLRHYYNWLTRQRY-NH2 (SEQ ID NO: 173)

MW (calculated): 4767.4 Da

Synthesis and purification methods: S01; P02

LCMS: 010_CA07; Rt: 13.90 min; m/3: 1589.0 m/4: 1192.1 m/5:

Compound 170

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13A,17I,18Q,22V,28Y,30W,31L]-hPYY(4-36)

iVal-APEK(C18DA-gGlu-Ahx)PEEDAAPEE-IQRYYVSLRHYYNWLTRQRY-NH2 (SEQ ID NO: 174)

MW (calculated): 4794.5 Da

Synthesis and purification methods: S01; P01

LCMS: 010_CA07; Rt: 10.60 min; m/3: m/4: 1199.0 m/5:

Compound 171

N{alpha-4}-(3-methylbutanoyl)-N{epsilon-7}-(6-[(4S)-4-carboxy-4-(17-carboxyheptadecanamido) butanamido] hexanoyl)-[4A,7K,9E,10A,18Q,22V,23E,28Y,30W,31L]-hPYY(4-36)

iVal-APEK(C18DA-gGlu-Ahx) PEADASPEELQRYYVELRHYYNWLTRQRY-NH2 (SEQ ID NO: 175)

MW (calculated): 4794.5 Da

Synthesis and purification methods: S01; P01

LCMS: 010_CA07; Rt: 9.57 min; m/3: 1599.2 m/4: m/5:

Compound 172

N{alpha-4}-(3-methylbutanoyl)-N{epsilon-7}-(6-[(4S)-4-carboxy-4-(17-carboxyheptadecanamido) butanamido] hexanoyl)-[4A,7K,9P,17I,18Q,22V,28Y,30W,31L]-hPYY (4-36)

iVal-APEK(C18DA-gGlu-Ahx)PPEDASPEE-IQRYYVSLRHYYNWLTRQRY-NH2 (SEQ ID NO: 176)

MW (calculated): 4778.5 Da

Synthesis and purification methods: S01; P01

LCMS: 010_CA07; Rt: 9.95 min; m/3: 1593.5 m/4: m/5:

Compound 173

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,18Q,22V,28Y,30W,31L]-hPYY (4-36)

iVal-APEK(C18DA-gGlu-Ahx)PEEDAT-PEELQRYYVSLRHYYNWLTRQRY-NH2 (SEQ ID NO: 177)

MW (calculated): 4824.5 Da

Synthesis and purification methods: S01; P01

LCMS: 010_CA07; Rt: 10.50 min; m/3: 1609.0 m/4: m/5:

Compound 174

N{alpha-4}-(3-methylbutanoyl)-N{epsilon-7}-(6-[(4S)-4-carboxy-4-(17-carboxyheptadecanamido) butanamido] hexanoyl)-[4A,7K,10A,16K,18Q,22V,28Y,29H,30K,31L]-hPYY(4-36)

iVal-APEK(C18DA-gGlu-Ahx)PGADAS-PEKLQRYYVSLRHYYHKLTRQRY-NH2 (SEQ ID NO: 178)

MW (calculated): 4644.4 Da

Synthesis and purification methods: S01; P02

LCMS: 010_CA07; Rt: 7.90 min; m/3: 1548.8 m/4: m/5:

Compound 175

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,13E,18Q,22I,23A,28Y,30W,31L]-hPYY(4-36)

iVal-APAK(C18DA-gGlu-Ahx)PEEDAE-PEELQRYYIALRHYYNWLTRQRY-NH2 (SEQ ID NO: 179)

MW (calculated): 4792.5 Da

Synthesis and purification methods: S01; P02

LCMS: 010_CA07; Rt: 10.86 min; m/3: m/4: 1198.8 m/5:

Compound 176

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,17I,18Q,22V,28Y,30W,31L]-hPYY(4-36)

iVal-APEK(C18DA-gGlu-Ahx)PEEDATPEE-IQRYYVSLRHYYNWLTRQRY-NH2 (SEQ ID NO: 180)

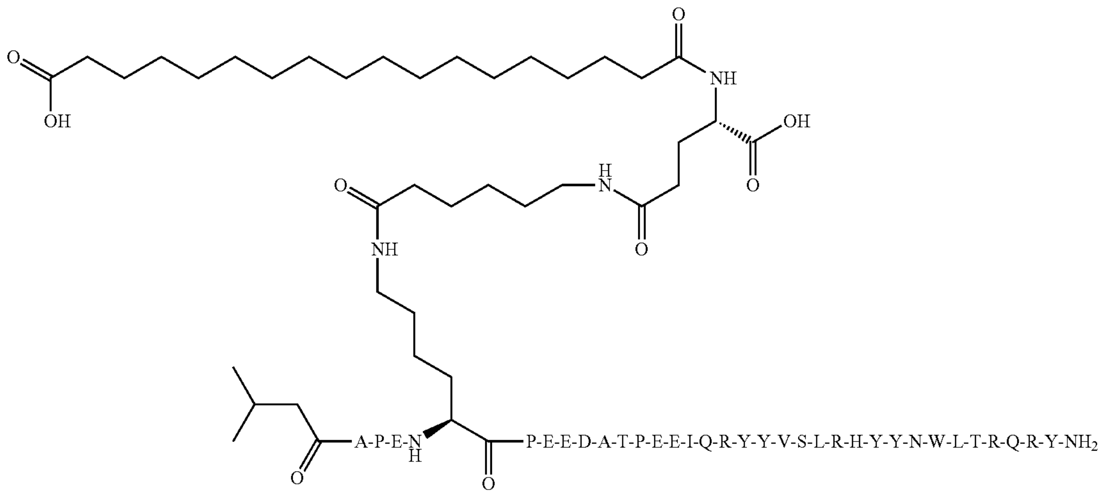

MW (calculated): 4824.5 Da

Synthesis and purification methods: S01; P01

LCMS: 010_CA07; Rt: 9.84 min; m/3: 1610.6 m/4: m/5:

Compound 177

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,18Q,19Q,22V,28Y,30W,31L]-hPYY(4-36)

iVal-APEK(C18DA-gGlu-Ahx)PEEDAT-PEELQQYYVSLRHYYNWLTRQRY-NH2 (SEQ ID NO: 181)

MW (calculated): 4796.4 Da

Synthesis and purification methods: S01; P02

LCMS: 010_CA07; Rt: 10.00 min; m/3: m/4: 1200.0 m/5:

Compound 178

N{alpha-4}-(3-methylbutanoyl)-N{epsilon-7}-(6-[(4S)-4-carboxy-4-(17-carboxyheptadecanamido) butanamido] hexanoyl)-[4A,7K,9E,10A,11A,13T,17I,18Q,22V,23A,28Y,30W,31L]-hPYY(4-36)

iVal-APEK(C18DA-gGlu-Ahx)PEAAATPEEIQRYY-VALRHYYNWLTRQRY-NH2 (SEQ ID NO: 182)

MW (calculated): 4706.4 Da

Synthesis and purification methods: 501; P02

LCMS: 010_CA07; Rt: 11.21 min; m/3: m/4: 1177.0 m/5:

Compound 179

N{alpha-4}-(3-methylbutanoyl)-N{epsilon-7}-(6-[(4S)-4-carboxy-4-(17-carboxyheptadecanamido) butanamido] hexanoyl)-[4A,7K,9E,10A,17T,18Q,22V,23A,28Y,30W,31L]-hPYY(4-36)

iVal-APEK(C18DA-gGlu-Ahx)PEADASPEETQRYY-VALRHYYNWLTRQRY-NH2 (SEQ ID NO: 183)

MW (calculated): 4724.4 Da

Synthesis and purification methods: S01; P01

LCMS: 010_CA07; Rt: 12.50 min; m/3: m/4: 1181.4 m/5:

Compound 180

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,18Q,22V,28Y,30W,31L,33K]-hPYY(4-36)

iVal-APEK(C18DA-gGlu-Ahx)PEEDAT-PEELQRYYVSLRHYYNWLTKQRY-NH2 (SEQ ID NO: 184)

MW (calculated): 4796.5 Da

Synthesis and purification methods: S01; P02

LCMS: 010_CA07; Rt: 9.80 min; m/3: 1600.8 m/4: m/5:

Compound 181

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,10A,13E,17I,18Q,22V,23A,28Y,30W,31L]-hPYY(4-36)

iVal-APAK(C18DA-gGlu-Ahx)PEADAEPEEIQRYY-VALRHYYNWLTRQRY-NH2 (SEQ ID NO: 185)

MW (calculated): 4720.4 Da

Synthesis and purification methods: 501; P02

LCMS: 010_CA07; Rt: 11.23 min; m/3: 1574.1 m/4: 1180.8 m/5:

Compound 182

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,17A,18Q,22V,23A,28Y,30W,31L]-hPYY(4-36)

iVal-APAK(C18DA-gGlu-Ahx)PEEDASPEEAQRYY-VALRHYYNWLTRQRY-NH2 (SEQ ID NO: 186)

MW (calculated): 4694.3 Da

Synthesis and purification methods: S01; P01

LCMS: 010_CA07; Rt: 12.70 min; m/3: 1565.3 m/4: m/5:

Compound 183

N{alpha-4}-(3-methylbutanoyl)-N{epsilon-7}-(6-[(4S)-4-carboxy-4-(17-carboxyheptadecanamido) butanamido] hexanoyl)-[4A,7K,8A,9E,17I,18Q,22V,28Y,30W,31L]-hPYY(4-36)

iVal-APEK(C18DA-gGlu-Ahx)AEEDASPEE-IQRYYVSLRHYYNWLTRQRY-NH2 (SEQ ID NO: 187)

MW (calculated): 4784.4 Da

Synthesis and purification methods: S01; P01

LCMS: 010_CA07; Rt: 10.60 min; m/3: 1595.9 m/4: m/5:

Compound 184

N{alpha-4}-(3-methylbutanoyl)-N{epsilon-7}-(6-[(4S)-4-carboxy-4-(17-carboxyheptadecanamido) butanamido] hexanoyl)-[4A,7K,9E,10A,13T,17I,18Q,22V,23A,28Y,30W,31L]-hPYY(4-36)

iVal-APEK(C18DA-gGlu-Ahx)PEADATPEEIQRYY-VALRHYYNWLTRQRY-NH2 (SEQ ID NO: 188)

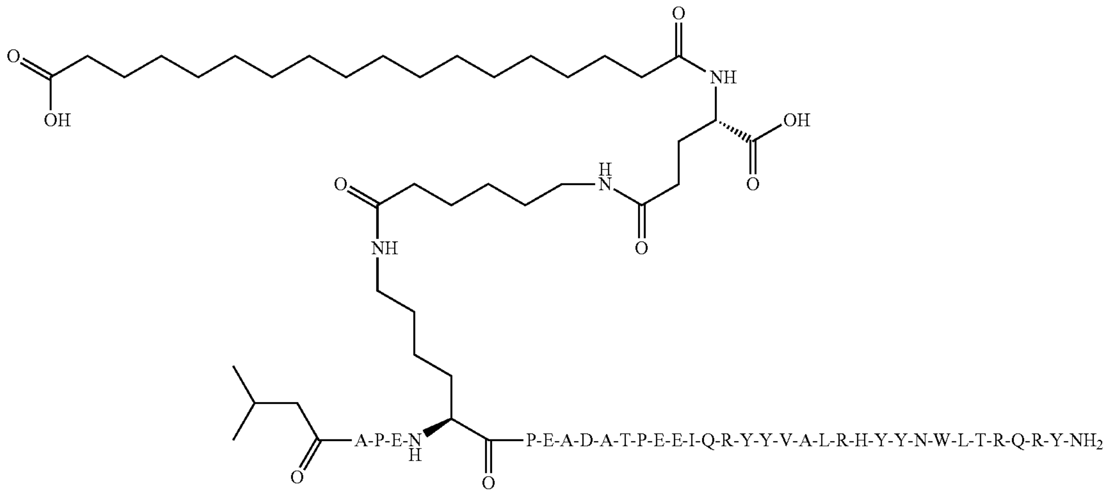

MW (calculated): 4750.4 Da

Synthesis and purification methods: 501; P01

LCMS: 010_CA07; Rt: 12.00 min; m/3: m/4: 1188.5 m/5:

Compound 185

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,14E,18Q,22V,28Y,30W,31L]-hPYY(4-36)

iVal-APAK(C18DA-gGlu-Ahx)PEEDA-SEEELQRYYVSLRHYYNWLTRQRY-NH2 (SEQ ID NO: 189)

MW (calculated): 4784.4 Da

Synthesis and purification methods: S01; P01

LCMS: 010_CA07; Rt: 10.80 min; m/3: 1595.2 m/4: m/5:

Compound 186

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13E,17A,18Q,22V,28Y,30W,31L]-hPYY(4-36)

iVal-APEK(C18DA-gGlu-Ahx)PEEDAEPEEA-QRYYVSLRHYYNWLTRQRY-NH2 (SEQ ID NO: 190)

MW (calculated): 4810.4 Da

Synthesis and purification methods: S01; P01

LCMS: 010_CA07; Rt: 13.20 min; m/3: m/4: 1203.8 m/5:

Compound 187

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,17P,18Q,22V,28Y,30W,31L]-hPYY(4-36)

iVal-APEK(C18DA-gGlu-Ahx)PEEDAT-PEEPQRYYVSLRHYYNWLTRQRY-NH2 (SEQ ID NO: 191)

MW (calculated): 4808.4 Da

Synthesis and purification methods: S01; P01

LCMS: 010_CA07; Rt: 9.38 min; m/3: 1603.3 m/4: m/5:

Compound 188

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,18Q,22V,28Y,30W,31L,32Q]-hPYY(4-36)

iVal-APEK(C18DA-gGlu-Ahx)PEEDAT-PEELQRYYVSLRHYYNWLQRQRY-NH2 (SEQ ID NO: 192)

MW (calculated): 4851.5 Da

Synthesis and purification methods: S01; P01

LCMS: 010_CA07; Rt: 11.13 min; m/3: 1618.0 m/4: m/5:

Compound 189

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,17T,18Q,22V,23A,28Y,30W,31L]-hPYY(4-36)

iVal-APAK(C18DA-gGlu-Ahx)PEEDASPEETQRYY-VALRHYYNWLTRQRY-NH2 (SEQ ID NO: 193)

MW (calculated): 4724.4 Da

Synthesis and purification methods: S01; P02

LCMS: 010_CA07; Rt: 11.50 min; m/3: m/4: 1182.1 m/5:

Compound 190

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,13T,18Q,22I,28Y,30W,31L]-hPYY(4-36)

iVal-APAK(C18DA-gGlu-Ahx)PEEDATPEELQRYYIS-LRHYYNWLTRQRY-NH2 (SEQ ID NO: 194)

MW (calculated): 4780.5 Da

Synthesis and purification methods: S01; P02

LCMS: 010_CA07; Rt: 10.28 min; m/3: 1594.5 m/4: m/5:

Compound 191

N{alpha-4}-(3-methylbutanoyl)-N{epsilon-7}-(6-[(4S)-4-carboxy-4-(17-carboxyheptadecanamido) butanamido] hexanoyl)-[4A,7K,9E,13T,17I,18Q,22E,28Y,30W,31L]-hPYY(4-36)

iVal-APEK(C18DA-gGlu-Ahx)PEEDATPEE-IQRYYESLRHYYNWLTRQRY-NH2 (SEQ ID NO: 195)

MW (calculated): 4854.5 Da

Synthesis and purification methods: S01; P02

LCMS: 010_CA07; Rt: 9.77 min; m/3: 1619.0 m/4: m/5:

Compound 192

N{alpha-4}-(3-methylbutanoyl)-N{epsilon-7}-(6-[(4S)-4-carboxy-4-(17-carboxyheptadecanamido) butanamido] hexanoyl)-[4A,7K,9E,10A,11P,18Q,22V,28Y,30W,31L]-hPYY(4-36)

iVal-APEK(C18DA-gGlu-Ahx) PEAPASPEELQRYYVSLRHYYNWLTRQRY-NH2 (SEQ ID NO: 196)

MW (calculated): 4734.4 Da

Synthesis and purification methods: S01; P02

LCMS: 010_CA07; Rt: 10.39 min; m/3: m/4: 1184.5 m/5:

Compound 193

N{alpha-4}-(3-methylbutanoyl)-N{epsilon-7}-(6-[(4S)-4-carboxy-4-(17-carboxyheptadecanamido) butanamido] hexanoyl)-[4A,7K,9E,11E,17I,18Q,22V,28Y,30W,31L]-hPYY(4-36)

iVal-APEK(C18DA-gGlu-Ahx)PEEEASPEE-IQRYYVSLRHYYNWLTRQRY-NH2 (SEQ ID NO: 197)

MW (calculated): 4824.5 Da

Synthesis and purification methods: S01; P01

LCMS: 010_CA07; Rt: 12.20 min; m/3: 1609.1 m/4: m/5:

Compound 194

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,13E,17I,18Q,22V,23A,28Y,30W,31L]-hPYY(4-36)

iVal-APAK(C18DA-gGlu-Ahx)PEEDAEPEEIQRYY-VALRHYYNWLTRQRY-NH2 (SEQ ID NO: 198)

MW (calculated): 4778.5 Da

Synthesis and purification methods: S01; P02

LCMS: 010_CA07; Rt: 10.80 min; m/3: m/4: 1195.1 m/5:

Compound 195

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,17I,18Q,22I,28Y,30W,31L]-hPYY(4-36)

iVal-APAK(C18DA-gGlu-Ahx)PEEDASPEEIQRYYIS-LRHYYNWLTRQRY-NH2 (SEQ ID NO: 199)

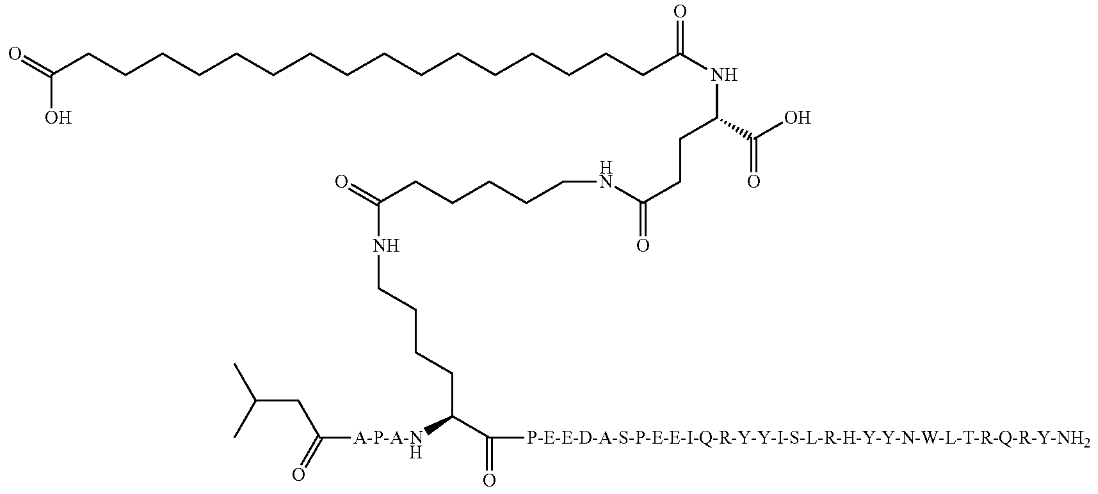

MW (calculated): 4766.4 Da

Synthesis and purification methods: S01; P02

LCMS: 010_CA07; Rt: 10.02 min; m/3: m/4: 1192.4 m/5:

Compound 196

N{alpha-4}-(3-methylbutanoyl)-N{epsilon-7}-(6-[(4S)-4-carboxy-4-(17-carboxyheptadecanamido) butanamido] hexanoyl)-[4A,7K,9E,10A,18Q,22V,28Y,30W,31L]-hPYY (4-36)

iVal-APEK(C18DA-gGlu-Ahx) PEADASPEELQRYYVSLRHYYNWLTRQRY-NH2 (SEQ ID NO: 200)

MW (calculated): 4752.4 Da

Synthesis and purification methods: 501; P01

LCMS: 010_CA07; Rt: 10.35 min; m/3: 1584.8 m/4: m/5:

Compound 197

N{alpha-4}-(3-methylbutanoyl)-N{epsilon-7}-(6-[(4S)-4-carboxy-4-(17-carboxyheptadecanamido) butanamido] hexanoyl)-[4A,7K,9E,17I,18Q,22V,23A,28Y,30W,31L]-hPYY(4-36)

iVal-APEK(C18DA-gGlu-Ahx)PEEDASPEEIQRYY-VALRHYYNWLTRQRY-NH2 (SEQ ID NO: 201)

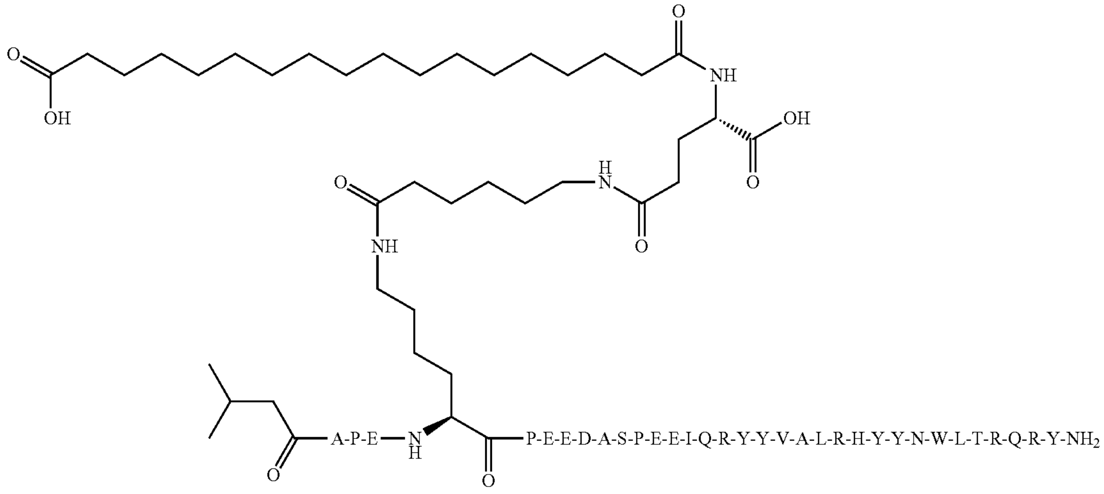

MW (calculated): 4794.5 Da

Synthesis and purification methods: S01; P01

LCMS: 010_CA07; Rt: 10.19 min; m/3: m/4: 1199.4 m/5:

Compound 198

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,10A,13E,17I,18Q,22V,28Y,30W,31L]-hPYY(4-36)

iVal-APAK(C18DA-gGlu-Ahx)PEADAEPEE-IQRYYVSLRHYYNWLTRQRY-NH2 (SEQ ID NO: 202)

MW (calculated): 4736.4 Da

Synthesis and purification methods: S01; P02

LCMS: 010_CA07; Rt: 10.70 min; m/3: m/4: 1184.9 m/5:

Compound 199

N{alpha-4}-(3-methylbutanoyl)-N{epsilon-7}-(6-[(4S)-4-carboxy-4-(17-carboxyheptadecanamido) butanamido] hexanoyl)-[4A,6A,7K,9E,11E,18Q,22V,28Y,30W,31L]-hPYY(4-36)

iVal-APAK(C18DA-gGlu-Ahx)PEEE-ASPEELQRYYVSLRHYYNWLTRQRY-NH2 (SEQ ID NO: 203)

MW (calculated): 4766.4 Da

Synthesis and purification methods: S01; P01

LCMS: 010_CA07; Rt: 10.40 min; m/3: m/4: 1192.0 m/5:

The following compound disclosed as Example 32 in WO 2016/198682 A1 was synthesized as reference:

```
Ref. 1
                                        (SEQ ID NO: 204)
iVal-RPEK(C18DA-gGlu-Ahx)PGEDASPEELQRYYISLRHYYNWLT

RQRY-NH2
```

Further compounds were synthesized as references:

```
Ref. 2
                                        (SEQ ID NO: 205)
iVal-RPEK(C18DA-gGlu-Ahx) PGEDASPEELQRYYISLAHYYNWL

TRQRY-NH2

Ref. 3
                                        (SEQ ID NO: 206)
iVal-RPEK(C18DA-gGlu-Ahx) PGEDASPEELQRYYISLRHYYNWL

TAQRY-NH2

Ref. 4
                                        (SEQ ID NO: 207)
iVal-RPEK(C18DA-gGlu-Ahx) PGEDASPEELQRYYISLRHYYNWL

TRQAY-NH2
```

The structure of Ref. 1 is—except for alanine at position 4—identical to Compound 92. This R4A mutation leads to a compound that shows much higher solubility at pH 6.2 (0.0 mg/ml for Ref. 1 vs. 9.2 mg/ml for Compound 92). At the same time high binding affinity and receptor activity are maintained for Compound 92 (see Table 2). Other arginine to alanine mutations at different positions (R25A in Ref. 2; R33A in Ref. 3; R35A in Ref. 4) negatively affect binding affinity and receptor activity of the resulting compounds.

TABLE 2

| Comp. | Seq. mod. vs. Ref. 1 | hY2 RLB (nM) (Example 1) | hY2 cAMP (nM) (Example 2) | SoL pH 6 (mg/mL) [final pH] (Example 3) | Sol pH 7 (mg/mL) [final pH] (Example 3) |
|---|---|---|---|---|---|
| Ref. 1 | — | 1.7 | 0.5 | 0.0 [6.2] | 6.7 [6.8] |
| Comp. 92 | R4A | 1.8 | 0.6 | 9.2 [6.1] | 8.9 [6.7] |
| Ref. 2 | R25A | 10.0 | 3.0 | 7.0 [6.1] | 8.5 [6.7] |
| Ref. 3 | R33A | >316 | >10 | 10.0 [6.1] | 10.0 [6.7] |
| Ref. 4 | R35A | >316 | >10 | 10.0 [6.1] | 10.0 [6.7]. |

EXAMPLES

The following examples demonstrate certain specific embodiments of the present invention. The following examples were carried out using standard techniques that are well known and routine to those of skill in the art, except where otherwise described in detail.

Example 1: Radioligand Binding Competition Assays (RLB)

The filtration RLB assay was carried out in 96-well plates in a final volume of 100 μl per well. Freeze-dried test peptides were dissolved in 100% dimethyl sulfoxide (DMSO) to stock solutions of 1 mM and serial dilutions were performed in assay buffer (50 mM HEPES, 5 mM $MgCl_2$, 1 mM $CaCl_2$, pH 7.4) containing 0.2% ovalbumin. 10 μl/well of the test peptide solution was added to the plates to give final concentrations ranging from 1 μM to 3 pM. Subsequently, 10 μl of human $^{125}$I-PYY(1-36) (Perkin Elmer) in assay buffer containing 0.2% ovalbumin was added to wells to give a final concentration of 0.02 nM. Next, 80 μL membranes (HTS066M, ChemiSCREEN™ Human Neuropeptide Y2 Receptor Membrane Preparation, CHEMICON) were added to each well to give a final protein concentration of 0.5 μg/well. The plates were sealed and incubated at room temperature for 2 hours in a plate shaker set at 400 rpm. The incubation was stopped by vacuum filtration onto 0.5% polyethylene amine (PE) presoaked GF/C filters using a 96-well FilterMate™ harvester (Perkin Elmer) followed by four washes with 300 μl/well ice-cold wash buffer (50 mM HEPES, 500 mM NaCl, pH7.4). Filter plates were then dried for 60 min at room temperature and the bottom of the plates was sealed with backing tape UniFilter-96. Finally, 50 μl/well scintillation counter cocktail (Microscint20, Packard) was added and the radioactivity was counted in the Packard TopCount NXT scintillation counter. $IC_{50}$ values (the half maximal inhibitory concentration of the agonist) were calculated by nonlinear regression analysis of sigmoidal dose-response curves. Ki values for binding affinity were acquired by the Cheng-Prusoff equation ($Ki=IC_{50}/(1+[L]/Kd)$, where Kd is the previously measured receptor specific dissociation constant (for NPY2R=0.07 nM) and [L] is $^{125}$I-PYY(1-36) radioligand concentration.

The RLB results are summarized in Table 3, below.

TABLE 3

| Compound | Ki [nM] |
|---|---|
| 1 | 2.05 |
| 2 | 2.40 |
| 3 | 1.57 |
| 4 | 4.65 |
| 5 | 12.71 |
| 6 | 1.42 |
| 7 | 1.04 |
| 8 | 106.17 |
| 9 | 3.32 |
| 10 | 2.46 |
| 11 | 1.40 |
| 12 | 4.16 |
| 13 | 1.53 |
| 14 | 1.28 |
| 15 | 3.98 |
| 16 | 2.81 |
| 17 | 24.63 |
| 18 | 2.48 |
| 19 | 9.63 |
| 20 | 2.41 |
| 21 | 3.38 |
| 22 | 4.98 |
| 23 | 12.59 |
| 24 | 3.39 |
| 25 | 1.55 |
| 26 | 5.64 |
| 27 | 10.47 |
| 28 | 0.49 |
| 29 | 1.36 |
| 30 | 0.30 |
| 31 | 34.66 |
| 32 | 13.56 |
| 33 | 2.53 |
| 34 | 3.53 |
| 35 | 1.40 |
| 36 | 1.25 |
| 37 | 3.66 |
| 38 | 12.44 |
| 39 | 2.73 |
| 40 | 0.67 |
| 41 | 19.75 |
| 42 | 1.98 |
| 43 | 2.49 |
| 44 | 5.86 |
| 45 | 6.17 |
| 46 | 5.21 |
| 47 | 0.51 |
| 48 | 1.54 |
| 49 | 11.60 |
| 51 | 2.59 |
| 52 | 2.39 |
| 53 | 3.07 |
| 54 | 8.97 |
| 55 | 2.96 |
| 56 | 4.39 |
| 57 | 2.07 |
| 58 | 3.46 |
| 59 | 1.93 |
| 60 | 6.04 |
| 61 | 0.41 |
| 62 | 1.44 |
| 63 | 0.93 |
| 64 | 0.86 |
| 65 | 0.98 |
| 66 | 2.33 |
| 67 | 2.22 |
| 68 | 9.07 |
| 69 | 0.54 |
| 70 | 2.26 |
| 71 | 1.97 |
| 72 | 2.79 |
| 73 | 2.16 |
| 74 | 3.17 |
| 75 | 1.43 |
| 76 | 2.68 |
| 77 | 9.73 |
| 78 | 1.80 |
| 79 | 1.54 |

TABLE 3-continued

| Compound | Ki [nM] |
|---|---|
| 80 | 4.62 |
| 81 | 2.65 |
| 82 | 0.58 |
| 83 | 6.91 |
| 84 | 1.60 |
| 85 | 1.61 |
| 86 | 4.33 |
| 87 | 22.38 |
| 88 | 16.28 |
| 89 | 1.16 |
| 90 | 8.71 |
| 91 | 4.64 |
| 92 | 1.84 |
| 93 | 1.71 |
| 94 | 0.93 |
| 95 | 2.92 |
| 96 | 3.06 |
| 97 | 4.23 |
| 99 | 0.66 |
| 100 | 1.01 |
| 101 | 1.77 |
| 102 | 7.15 |
| 103 | 1.94 |
| 104 | 14.11 |
| 105 | 5.97 |
| 106 | 2.46 |
| 107 | 5.13 |
| 108 | 2.77 |
| 109 | 13.98 |
| 110 | 6.42 |
| 111 | 2.14 |
| 112 | 4.28 |
| 113 | 3.53 |
| 114 | 0.95 |
| 115 | 2.22 |
| 116 | 2.46 |
| 117 | 3.09 |
| 118 | 1.00 |
| 119 | 5.73 |
| 120 | 1.49 |
| 121 | 1.45 |
| 122 | 2.73 |
| 123 | 3.65 |
| 124 | 3.07 |
| 125 | 3.37 |
| 126 | 4.42 |
| 127 | 3.36 |
| 128 | 2.91 |
| 129 | 1.42 |
| 130 | 9.36 |
| 131 | 1.54 |
| 132 | 2.75 |
| 133 | 4.68 |
| 134 | 2.80 |
| 135 | 3.83 |
| 136 | 1.07 |
| 137 | 49.59 |
| 138 | 12.53 |
| 139 | 3.60 |
| 140 | 1.41 |
| 141 | 8.17 |
| 142 | 3.97 |
| 143 | 3.42 |
| 144 | 9.76 |
| 145 | 5.29 |
| 146 | 8.93 |
| 147 | 5.04 |
| 148 | 2.85 |
| 149 | 3.97 |
| 150 | 2.18 |
| 151 | 1.68 |
| 152 | 1.32 |
| 153 | 6.80 |
| 154 | 3.71 |
| 155 | 7.60 |
| 156 | 4.20 |
| 157 | 1.68 |
| 158 | 0.58 |

TABLE 3-continued

| Compound | Ki [nM] |
|---|---|
| 159 | 2.75 |
| 160 | 1.37 |
| 161 | 4.00 |
| 162 | 14.93 |
| 163 | 0.67 |
| 164 | 2.80 |
| 165 | 1.43 |
| 166 | 2.05 |
| 167 | 4.58 |
| 168 | 3.56 |
| 169 | 5.82 |
| 170 | 2.28 |
| 171 | 2.83 |
| 172 | 0.81 |
| 173 | 4.07 |
| 174 | 0.21 |
| 175 | 3.00 |
| 176 | 1.48 |
| 177 | 8.65 |
| 178 | 3.39 |
| 179 | 0.89 |
| 180 | 15.05 |
| 181 | 1.33 |
| 182 | 2.20 |
| 183 | 18.80 |
| 184 | 0.64 |
| 185 | 2.06 |
| 186 | 7.21 |
| 187 | 15.32 |
| 188 | 5.46 |
| 189 | 0.97 |
| 190 | 1.95 |
| 191 | 8.32 |
| 192 | 0.74 |
| 193 | 3.42 |
| 194 | 26.37 |
| 195 | 0.78 |
| 196 | 3.57 |
| 197 | 2.03 |
| 198 | 1.38 |
| 199 | 2.87 |

In general, the data from the RLB assay is predictive for the acute food intake inhibition in mice (Experiment 6).

Example 2: HTRF cAMP Gi Assay

The Homogenous Time Resolved fluorescence (HTRF) technology optimized for Gi coupled receptors has thoroughly been described in Cisbio cAMP Gi kit manual. Briefly, the production of intracellular cAMP will generate a competition between unlabeled cAMP and exogenously added d2-cAMP for anti-cAMP antibodies conjugated to cryptate. CHO-K1 cells stably expressing the human NPY1, NPY2, NPY4 and NPY5 receptors were used with the cells brought to life from a frozen stock immediately before assay performance. 2000 cells per well were applied for all four NPY receptor subtype assays. A 384-well format was used applying a total volume of 20 μl using 5 μl cells, 2.5 μl peptide agonist, 2.5 μl forskolin and 5 μl of each of the fluorophores. Cells were incubated with agonist peptides (11 points concentration response curves) and forskolin (~90% activity level, 3-11 μM forskolin) for 40 min at 37° C. using DPBS containing 0.5 mM IBMX as stimulation buffer. After addition of HTRF® detection reagents and incubation with shaking (2400 rpm) for one hour at room temperature signals at 620 and 665 nm (raw counts: ratio of 665/620) were detected. Concentration-response evaluation of compounds was performed with 11 concentrations of agonist peptides (covering 3 decades). EC50 values were calculated by nonlinear regression using sigmoid concentration-response with variable slope.

The in vitro activity results (expressed as $EC_{50}$ values) are summarized in Table 4, below.

TABLE 4

| Compound No. | hY2R (nM) | hY1R (nM) | hY4R (nM) | hY5R (nM) |
|---|---|---|---|---|
| hPYY3-36 | 0.160 | 250 | >5000 | 73.2 |
| 7 | 0.143 | >5000 | >5000 | >5000 |
| 11 | 0.136 | >5000 | >5000 | >5000 |
| 12 | 0.250 | | | >5000 |
| 14 | 0.086 | | | >5000 |
| 15 | 0.140 | | | >5000 |
| 16 | 0.310 | | | >5000 |
| 23 | 0.181 | | | >5000 |
| 26 | 0.108 | | | >5000 |
| 40 | 0.122 | >5000 | >5000 | >5000 |
| 52 | 0.176 | | | >5000 |
| 53 | 0.352 | >5000 | >5000 | >5000 |
| 55 | 0.352 | >5000 | >5000 | >5000 |
| 63 | 0.109 | >5000 | >5000 | >5000 |
| 67 | 0.227 | | | >5000 |
| 72 | 0.197 | | | >5000 |
| 76 | 0.172 | | | >5000 |
| 79 | 0.076 | | | >5000 |
| 84 | 0.205 | >5000 | 1000 | >5000 |
| 91 | 0.219 | | | 5000 |
| 99 | 0.281 | >5000 | >5000 | >5000 |
| 106 | 0.121 | | | >5000 |
| 114 | 0.186 | >5000 | >5000 | >5000 |
| 118 | 0.161 | >5000 | >5000 | >5000 |
| 122 | 0.273 | >5000 | >5000 | >5000 |
| 128 | 0.344 | >5000 | >5000 | >5000 |
| 129 | 0.270 | >5000 | >5000 | >5000 |
| 136 | 0.138 | >5000 | >5000 | >5000 |
| 140 | 0.230 | | | >5000 |
| 145 | 0.118 | | | >5000 |
| 146 | 0.130 | | | >5000 |
| 147 | 0.146 | | | >5000 |
| 150 | 0.243 | >5000 | >5000 | >5000 |
| 160 | 0.230 | >5000 | >5000 | >5000 |
| 163 | 0.130 | >5000 | >5000 | >5000 |
| 172 | 0.079 | | | >5000 |
| 176 | 0.168 | >5000 | >5000 | >5000 |
| 183 | 0.447 | | | >5000 |
| 184 | 0.232 | >5000 | >5000 | >5000 |
| 186 | 0.729 | >5000 | >5000 | >5000 |
| 189 | 0.273 | >5000 | >5000 | >5000 |
| 193 | 0.331 | >5000 | >5000 | >5000 |
| 195 | 0.197 | >5000 | >5000 | >5000 |
| 196 | 0.086 | | | >5000 |
| 197 | 0.156 | >5000 | >5000 | >5000 |

Example 3: Solubility Determination

Peptides (as TFA salts) were weighed out in a filter unit (Mini-UniPrep Syringeless Filter 0.45 μm, Whatman), and 0.1 M sodium diphosphate buffer at pH 6.4 or 7.0 was added to achieve 10 mg/ml final concentration. The peptide was dissolved by shaking the filter unit horizontally at 600 rpm for 2 hours at room temperature. The sample was filtered, to remove any insoluble particles and diluted to 1 mg/ml in 50% acetonitrile. The control was prepared by weighing out the corresponding peptide and dissolving it in 50% acetonitrile to final concentration of 1 mg/ml. Both the control and sample were analysed with reversed phase chromatography. The area under the peak of the sample was compared to the control and the solubility was calculated based on that ratio.

The pH was measured and recorded for each sample. Typically, buffer pH dropped by 0.2 to 0.3 pH units due to the TFA content of the peptide.

UPLC Method:

System: UltiMate 3000 UPLC, ThermoFisher

Mobile phase A: 5% acetonitrile, 95% water, 0.03% trifluoracetic acid.

Mobile phase B: 95% acetonitrile, 5% water, 0.03% trifluoracetic acid.

Flow: 1 ml/mm

Gradient: 0-100% mobile phase B (2 mins.)

Column: Kinetix, 5 μm C8, 100 Å, 50×2.1 mm

Column temperature: 50° C.

The results from the solubility determination are summarized in Table 5, below.

TABLE 5

| Compound | Sol6 (mg/ml) | Sol6 pH | Sol7 (mg/ml) | Sol7 pH |
|---|---|---|---|---|
| 1 | 10.0 | 6.1 | 7.6 | 6.8 |
| 2 | 9.5 | 6.1 | 9.5 | 6.8 |
| 3 | 10.0 | 6.3 | 10.0 | 6.8 |
| 4 | 10.0 | 6.1 | 10.0 | 6.8 |
| 5 | 3.6 | 6.2 | 8.8 | 6.8 |
| 6 | 9.6 | 6.1 | 10.0 | 6.8 |
| 7 | 8.9 | 6.1 | 9.2 | 6.9 |
| 8 | 9.7 | 6.0 | 9.6 | 6.7 |
| 9 | 9.7 | 6.1 | 9.9 | 6.7 |
| 10 | 0.0 | 6.2 | 0.0 | 6.7 |
| 11 | 8.9 | 6.1 | 8.7 | 6.8 |
| 12 | 9.4 | 6.0 | 9.8 | 6.7 |
| 13 | 10.0 | 6.1 | 10.0 | 6.7 |
| 14 | 9.3 | 6.2 | 8.4 | 6.8 |
| 15 | 9.3 | 6.2 | 9.2 | 6.8 |
| 16 | 10.0 | 6.1 | 8.3 | 6.8 |
| 17 | 10.0 | 6.0 | 10.0 | 6.7 |
| 18 | 9.3 | 6.0 | 9.5 | 6.7 |
| 19 | 10.0 | 6.0 | 9.2 | 6.7 |
| 20 | >10.0 | 6.1 | 10.0 | 6.8 |
| 21 | 10.0 | 6.1 | 10.0 | 6.8 |
| 22 | 9.7 | 6.0 | 9.8 | 6.7 |
| 23 | 9.8 | 6.2 | 10.0 | 6.8 |
| 24 | 9.8 | 6.1 | 10.0 | 6.8 |
| 25 | 9.3 | 6.2 | 9.3 | 6.8 |
| 26 | 9.2 | 6.2 | 9.1 | 6.8 |
| 27 | 9.1 | 6.1 | 9.4 | 6.8 |
| 28 | >10.0 | 6.1 | >10.0 | 6.7 |
| 29 | 9.9 | 6.2 | 10.0 | 6.8 |
| 30 | 0.1 | 6.2 | 9.4 | 6.8 |
| 31 | >10.0 | 6.1 | 10.0 | 6.8 |
| 32 | 8.2 | 6.2 | 9.3 | 6.8 |
| 33 | 7.2 | 6.2 | 8.3 | 6.8 |
| 34 | 9.2 | 6.1 | 9.1 | 6.8 |
| 35 | 0.0 | 6.2 | 2.4 | 6.8 |
| 36 | 0.0 | 6.3 | 0.4 | 6.8 |
| 37 | 10.0 | 6.1 | 10.0 | 6.8 |
| 38 | 10.0 | 6.1 | 10.0 | 6.8 |
| 39 | 10.0 | 6.1 | 10.0 | 6.8 |
| 40 | 8.5 | 6.1 | 8.2 | 6.8 |
| 41 | 9.8 | 6.0 | 10.0 | 6.7 |
| 42 | 9.8 | 6.0 | 9.9 | 6.7 |
| 43 | 0.0 | 6.3 | 0.0 | 6.8 |
| 44 | 9.7 | 6.2 | 10.0 | 6.8 |
| 45 | >10.0 | 6.1 | >10.0 | 6.7 |
| 46 | 10.0 | 6.1 | 10.0 | 6.8 |
| 47 | 9.4 | 6.1 | 9.9 | 6.7 |
| 48 | 0.0 | 6.1 | 0.3 | 6.7 |
| 49 | >10.0 | 6.1 | >10.0 | 6.7 |
| 51 | 9.6 | 6.0 | 9.7 | 6.7 |
| 52 | 9.5 | 6.0 | 9.5 | 6.7 |
| 53 | 8.7 | 6.1 | 9.6 | 6.8 |
| 54 | 10.0 | 6.0 | 10.0 | 6.7 |
| 55 | >10.0 | 6.0 | >10.0 | 6.7 |
| 56 | 9.0 | 6.1 | 9.2 | 6.7 |
| 57 | 8.3 | 6.1 | 9.6 | 6.7 |
| 58 | 8.6 | 6.0 | 8.8 | 6.7 |
| 59 | 9.7 | 6.0 | 9.6 | 6.7 |
| 60 | >10.0 | 6.1 | 10.0 | 6.7 |
| 61 | 0.1 | 6.1 | 8.9 | 6.8 |
| 62 | 8.8 | 6.1 | 9.3 | 6.7 |
| 63 | 10.0 | 6.1 | >10.0 | 6.8 |
| 64 | 9.8 | 6.1 | 9.6 | 6.7 |
| 65 | 7.9 | 6.2 | 9.0 | 6.8 |
| 66 | 9.2 | 6.1 | 9.2 | 6.8 |
| 67 | 9.3 | 6.1 | 7.9 | 6.8 |

TABLE 5-continued

| Compound | Sol6 (mg/ml) | Sol6 pH | Sol7 (mg/ml) | Sol7 pH |
|---|---|---|---|---|
| 68 | 9.9 | 6.0 | 10.0 | 6.7 |
| 69 | 0.1 | 6.2 | 9.5 | 6.8 |
| 70 | 9.2 | 6.2 | 9.5 | 6.8 |
| 71 | >10.0 | 6.1 | >10.0 | 6.8 |
| 72 | 9.0 | 6.1 | 9.2 | 6.7 |
| 73 | 8.6 | 6.1 | 8.2 | 6.8 |
| 74 | 8.4 | 6.2 | 9.2 | 6.8 |
| 75 | >10.0 | 6.0 | >10.0 | 6.6 |
| 76 | 10.0 | 6.2 | 10.0 | 6.8 |
| 77 | >10.0 | 6.1 | 9.0 | 6.9 |
| 78 | 8.1 | 6.2 | 7.6 | 6.8 |
| 79 | 10.0 | 6.1 | 10.0 | 6.7 |
| 80 | 8.1 | 6.1 | 8.2 | 6.8 |
| 81 | 8.9 | 6.0 | 8.9 | 6.7 |
| 82 | 0.0 | 6.2 | 9.0 | 6.9 |
| 83 | 10.0 | 6.1 | 10.0 | 6.7 |
| 84 | 9.3 | 6.2 | 9.3 | 6.8 |
| 85 | 8.6 | 6.2 | 9.1 | 6.8 |
| 86 | >10.0 | 6.0 | >10.0 | 6.7 |
| 87 | 9.7 | 6.1 | 9.7 | 6.7 |
| 88 | 8.7 | 6.0 | 8.9 | 6.6 |
| 89 | 0.1 | 6.2 | 8.0 | 6.8 |
| 90 | 9.6 | 6.1 | 10.0 | 6.8 |
| 91 | 8.9 | 6.0 | 9.4 | 6.7 |
| 92 | 9.2 | 6.1 | 8.9 | 6.7 |
| 93 | 9.4 | 6.1 | 9.7 | 6.7 |
| 94 | 8.4 | 6.1 | 8.9 | 6.8 |
| 95 | 8.9 | 6.1 | 7.9 | 6.8 |
| 96 | 8.8 | 6.1 | 8.7 | 6.7 |
| 97 | >10.0 | 6.1 | >10.0 | 6.7 |
| 99 | 9.4 | 6.1 | 9.3 | 6.8 |
| 100 | 9.8 | 6.2 | 5.7 | 6.8 |
| 101 | 9.1 | 6.2 | 9.2 | 6.8 |
| 102 | 10.0 | 6.1 | 9.7 | 6.7 |
| 103 | 8.0 | 6.1 | 7.8 | 6.8 |
| 104 | 9.6 | 6.1 | 8.6 | 6.8 |
| 105 | >10.0 | 6.1 | 9.9 | 6.7 |
| 106 | 9.4 | 6.2 | 7.4 | 6.8 |
| 107 | 11.0 | 6.1 | 11.0 | 6.8 |
| 108 | 8.6 | 6.2 | 8.0 | 6.8 |
| 109 | 10.0 | 6.0 | 8.5 | 6.7 |
| 110 | 10.0 | 6.1 | >10.0 | 6.7 |
| 111 | 0.0 | 6.2 | 0.0 | 6.8 |
| 112 | 9.9 | 6.0 | 10.0 | 6.7 |
| 113 | >10.0 | 6.0 | 10.0 | 6.7 |
| 114 | 8.5 | 6.1 | 9.2 | 6.8 |
| 115 | 9.0 | 6.0 | 8.5 | 6.8 |
| 116 | 0.0 | 6.3 | 0.0 | 6.8 |
| 117 | 9.8 | 6.1 | 9.4 | 6.8 |
| 118 | 10.0 | 6.0 | 9.5 | 6.7 |
| 119 | 9.3 | 6.0 | 9.1 | 6.7 |
| 120 | 0.0 | 6.3 | 0.2 | 6.8 |
| 121 | 9.1 | 6.1 | 8.9 | 6.7 |
| 122 | 9.8 | 6.2 | 9.9 | 6.8 |
| 123 | 9.1 | 6.1 | 8.7 | 6.8 |
| 124 | 9.7 | 6.2 | >10.0 | 6.8 |
| 125 | 9.7 | 6.1 | 10.0 | 6.8 |
| 126 | 9.6 | 6.1 | 8.8 | 6.8 |
| 127 | 6.5 | 6.2 | >10.0 | 6.8 |
| 128 | 10.0 | 6.2 | >10.0 | 6.9 |
| 129 | 10.0 | 6.0 | 10.0 | 6.7 |
| 130 | 9.9 | 6.0 | 10.0 | 6.6 |
| 131 | 10.0 | 6.1 | >10.0 | 6.7 |
| 132 | 8.7 | 6.2 | 9.3 | 6.8 |
| 133 | 9.6 | 6.1 | 9.7 | 6.7 |
| 134 | 10.0 | 6.0 | 10.0 | 6.7 |
| 135 | 0.2 | 6.2 | >10.0 | 6.8 |
| 136 | 9.6 | 6.2 | 10.0 | 6.8 |
| 137 | >10.0 | 6.2 | >10.0 | 6.8 |
| 138 | 9.9 | 6.0 | 9.5 | 6.8 |
| 139 | 7.3 | 6.1 | 8.8 | 6.8 |
| 140 | 9.9 | 6.1 | 9.3 | 6.8 |
| 141 | 9.6 | 6.2 | 9.7 | 6.8 |
| 142 | >10.0 | 6.1 | >10.0 | 6.7 |
| 143 | 10.0 | 6.0 | >10.0 | 6.7 |
| 144 | 9.7 | 6.0 | 9.6 | 6.7 |
| 145 | 7.2 | 6.2 | 9.0 | 6.8 |

TABLE 5-continued

| Compound | Sol6 (mg/ml) | Sol6 pH | Sol7 (mg/ml) | Sol7 pH |
|---|---|---|---|---|
| 146 | 9.8 | 6.1 | 9.6 | 6.8 |
| 147 | 9.4 | 6.1 | 9.2 | 6.8 |
| 148 | 9.7 | 6.1 | 10.0 | 6.7 |
| 149 | 8.7 | 6.2 | 10.0 | 6.8 |
| 150 | 9.7 | 6.2 | 10.0 | 6.8 |
| 151 | 8.2 | 6.1 | 9.7 | 6.8 |
| 152 | 8.8 | 6.0 | 8.8 | 6.7 |
| 153 | 6.0 | 6.0 | 9.5 | 6.7 |
| 154 | 8.3 | 6.2 | >10.0 | 6.8 |
| 155 | >10.0 | 6.2 | >10.0 | 6.8 |
| 156 | 9.8 | 6.1 | 9.6 | 6.8 |
| 157 | 0.0 | 6.2 | 0.3 | 6.8 |
| 158 | 0.0 | 6.2 | 0.4 | 6.9 |
| 159 | >10.0 | 6.1 | 10.0 | 6.8 |
| 160 | 10.0 | 6.2 | 9.7 | 6.9 |
| 161 | 0.2 | 6.2 | >10.0 | 6.8 |
| 162 | 9.0 | 6.0 | 9.3 | 6.7 |
| 163 | 8.9 | 6.2 | 9.2 | 6.8 |
| 164 | 9.3 | 6.1 | 9.2 | 6.7 |
| 165 | 8.8 | 6.1 | 9.1 | 6.7 |
| 166 | 9.2 | 6.1 | 9.7 | 6.7 |
| 167 | 0.0 | 6.2 | 9.5 | 6.9 |
| 168 | 8.8 | 6.2 | 9.1 | 6.8 |
| 169 | 9.7 | 6.1 | 9.8 | 6.8 |
| 170 | >10.0 | 6.0 | 10.0 | 6.7 |
| 171 | 10.0 | 6.1 | 10.0 | 6.8 |
| 172 | 10.0 | 6.2 | >10.0 | 6.8 |
| 173 | 9.2 | 6.0 | 9.6 | 6.7 |
| 174 | 3.1 | 6.1 | 1.2 | 6.7 |
| 175 | 10.0 | 6.1 | 10.0 | 6.8 |
| 176 | 9.4 | 6.2 | 9.3 | 6.8 |
| 177 | >10.0 | 6.0 | 10.0 | 6.7 |
| 178 | 0.0 | 6.3 | 0.4 | 6.9 |
| 179 | 8.1 | 6.2 | 8.3 | 6.8 |
| 180 | 9.9 | 6.2 | 10.0 | 6.8 |
| 181 | 9.5 | 6.2 | 9.3 | 6.9 |
| 182 | 6.9 | 6.1 | 8.4 | 6.8 |
| 183 | 8.4 | 6.2 | 8.7 | 6.8 |
| 184 | 9.1 | 6.1 | 9.1 | 6.8 |
| 185 | 8.7 | 6.1 | 8.9 | 6.8 |
| 186 | 9.0 | 6.1 | 10.0 | 6.8 |
| 187 | 7.8 | 6.1 | >10.0 | 6.7 |
| 188 | 9.5 | 6.2 | 9.8 | 6.8 |
| 189 | 9.4 | 6.2 | 9.8 | 6.8 |
| 190 | 8.4 | 6.2 | 8.4 | 6.8 |
| 191 | >10.0 | 6.0 | >10.0 | 6.7 |
| 192 | 0.0 | 6.2 | 9.0 | 6.8 |
| 193 | 8.9 | 6.2 | 9.1 | 6.8 |
| 194 | >10.0 | 6.2 | 10.0 | 6.8 |
| 195 | 8.2 | 6.2 | 8.2 | 6.8 |
| 196 | 8.4 | 6.2 | 9.8 | 6.8 |
| 197 | 8.9 | 6.1 | 10.0 | 6.8 |
| 198 | >10.0 | 6.3 | >10.0 | 6.8 |
| 199 | 9.0 | 6.2 | 9.1 | 6.8 |
| Ref 1. | 0.0 | 6.2 | 6.7 | 6.8 |

Example 4: DLS Studies

Aggregation combined with particle growth in peptide solutions was detected by dynamic light scattering (DLS). Test peptides (5 mg/ml) were dissolved in 50 mM phosphate buffer with EDTA (0.05 mg/ml) which is adjusted to a final pH of 7.2. Solutions were filtered through a 0.2 μm filter and shaken with a lab shaker at approx. 150 rpm at room temperature for 5 to 7 days. Samples were analyzed with a particle size analyzer (DLS, Horiba Nano Particle Analyzer SZ-100) at day 0 and at the end of the study. Formation of aggregates was detected by an increase in particle size over time and rated as OK, indicating no increase in particle size, and NOK, indicating an increase in particle size.

The results from the DLS studies are summarized in Table 6.

TABLE 6

| Example | DLS |
|---|---|
| 7 | OK |
| 11 | OK |
| 26 | OK |
| 40 | OK |
| 63 | OK |
| 84 | OK |
| 92 | NOK |
| 99 | OK |
| 114 | OK |
| 118 | OK |
| 122 | OK |
| 129 | NOK |
| 136 | OK |
| 146 | OK |
| 150 | OK |
| 160 | NOK |
| 163 | OK |
| 176 | OK |
| 184 | OK |
| 195 | OK |
| 197 | OK |

Example 5: Mouse PK

Pharmacokinetic parameters of the test compounds were determined after intravenous administration to NMRI mice.

Male NMRI mice were obtained either from Charles River (Germany) or from Janvier (France) weighing approximately 30 to 40 g. Mice were housed in standard cages with light cycle of 12-hour dark and 12-hour light. Standardized food and water were offered ad libitum to the animals during the whole experimental period.

The respective peptide was dissolved in 50 mM phosphate buffer (pH 7.0) containing 5% mannitol. Intravenous doses of 30 nmol/kg were given via a tail vein.

Serial blood samples were collected from the vena sephena into tubes containing EDTA as anticoagulant at different time points up to 48 h post dosing. After centrifugation for approximately 5 minutes, plasma samples were transferred to 96-well PCR plates, immediately frozen and kept at approximately −20° C. until analyzed for plasma concentration by liquid chromatography mass spectrometry (LC-MS/MS). Individual plasma concentration-time profiles were analyzed by a non-compartmental approach, and the resulting pharmacokinetic parameters were determined.

| Compound | Mouse MRT (h) | Terminal half-life (h) |
|---|---|---|
| Ref. 1 | 13.0 | 9.0 |

Mouse MRT of the PYY analogues according to the invention that have been measured were comparable to Ref. 1 and show very long half-lives as compared to the half-life of hPYY(3-36).

Example 6: Effect on Acute Food Intake in Normal NMRI Mice

Male NMRI mice were obtained from Charles River (Charles River, Research Models & Services Germany GmbH) or from JanVier (JanVier Labs, France) at 5 weeks of age. The animals were group housed 4 mice pr. cage under a 12/12 h dark-light cycle, light off at 3 PM. Room temperature was controlled to 21° C.±1° C., with 60%±20% humidity.

Animals had ad libitum access to regular rodent chow (KLIBA Nafag 3430 or Altromin 1324, Brogaarden, Denmark) and tap water.

Animals were transferred 5-7 days before the start of the study to a real-time food intake monitoring system, HM-2 system (MBRose, Denmark), to allow acclimatization to experimental conditions. As the animals were uniquely identified with microchips, each individual animal was identified by its microchip upon entry and exit from the food channel. Randomization of the mice for each study group (n=7-8) was based on body weight measured the day before the start of the study. A vehicle-treated (50 mM phosphate buffer pH7 with 5% Mannitol) group was included in each experiment. Six hours before the start of the night phase animals were fasted. One hour before the dark phase animals were dosed once subcutaneously (5 nmol/kg) with test peptide. Food intake was reported hourly for a period of 24 h. The food intake of the treated groups was normalized (in %) to the average food intake of the group receiving vehicle (Table 7). Statistical significance was evaluated using One-way analysis of variance with Turkey's multiple comparison test. P<0.05 was considered statistically significant.

TABLE 7

| Compound | Acute Food Intake 24 h [% vehicle] |
|---|---|
| 7 | 38 |
| 26 | 53 |
| 40 | 41 |
| 63 | 62 |
| 84 | 57 |
| 114 | 65 |
| 136 | 64 |
| 146 | 50 |
| 163 | 46 |
| 176 | 44 |
| 197 | 57 |
| Ref. 1 | 49 |

Example 7: Activity after Incubation in Solutions at Different pH Values

Peptides (as TFA salts) were weighed out in a filter unit (Mini-UniPrep Syringeless Filter 0.45 μm, Whatman), and 0.1 M sodium diphosphate buffer at pH 6.4 or 7.4, respectively, or 0.2 M TRIS buffer at pH 8.3 was added to achieve 10 mg/ml final concentration. The peptide was (partially) dissolved by shaking the filter unit horizontally at approx. 400 rpm for 2 hours at room temperature. The sample was filtered to remove any insoluble particles. The filtrate was subsequently subjected to the binding assay as described in Example 1. The apparent binding affinity (Ki) reported in Table 8 is calculated based on an assumed concentration of 10 mg/ml.

Compounds of the invention are active in the binding assay after incubation in solutions at different pH values, including pH 6. This demonstrates the fundamental feasibility of a liquid formulation of the compounds according to the invention at ~pH 6 (in the pH range from ~6 to ~8).

Contrary hereto, after incubation at ~pH 6, solutions of Ref. 1 (after filtration) show a weak response in the binding assay (apparent significant (>45×) affinity loss due to low solubility of Ref. 1 in buffered media at pH 6). Therefore, the low intrinsic solubility of Ref. 1 at ~pH 6 limits the formulation space in the physiological pH range of 6-8 of a liquid formulation of Ref. 1.

TABLE 8

| Compound | hY2R RLB Ki (nM) DMSO | RLB 6 (pH6.1-6.2) (nM) | RLB 7 (pH7.1-7.2) (nM) | RLB 8 (pH8.1-8.2) (nM) | RLB ratio (RLB6/RLB7) | RLB ratio (RLB8/RLB7) |
|---|---|---|---|---|---|---|
| Ref. 1 | 9.3 | >316 | 7.1 | 4.6 | >45 | 0.7 |
| 176 | 8.7 | 3.9 | 4.0 | 5.7 | 1.0 | 1.4 |
| 7 | 4.6 | 4.7 | 4.5 | 3.1 | 1.1 | 0.7 |
| 84 | 4.8 | 7.5 | 5.5 | 5.4 | 1.3 | 1.0 |
| 40 | 5.6 | 4.6 | 7.3 | 3.8 | 0.6 | 0.5 |
| 163 | 7.6 | 6.8 | 7.1 | 4.9 | 1.0 | 0.7 |
| 63 | 6.6 | 5.6 | 5.4 | 4.7 | 1.0 | 0.9 |

What we claim:

1. A PYY analogue comprising:

(SEQ ID NO: 11)

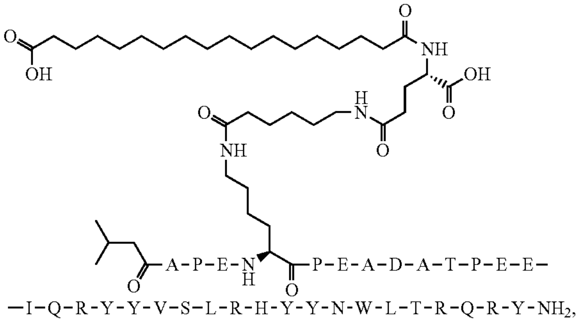

or a pharmaceutically acceptable salt thereof.

2. A PYY analogue, wherein the PYY analogue is:

(SEQ ID NO: 11)

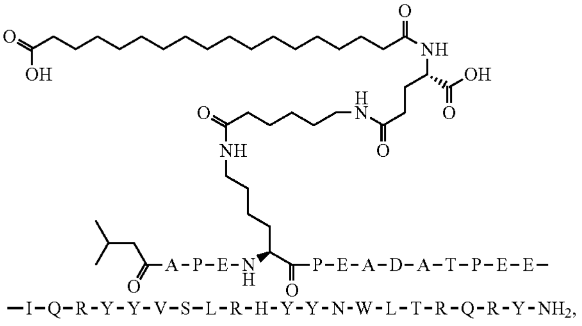

or a pharmaceutically acceptable salt thereof.

3. A PYY analogue comprising:
(SEQ ID NO: 11)
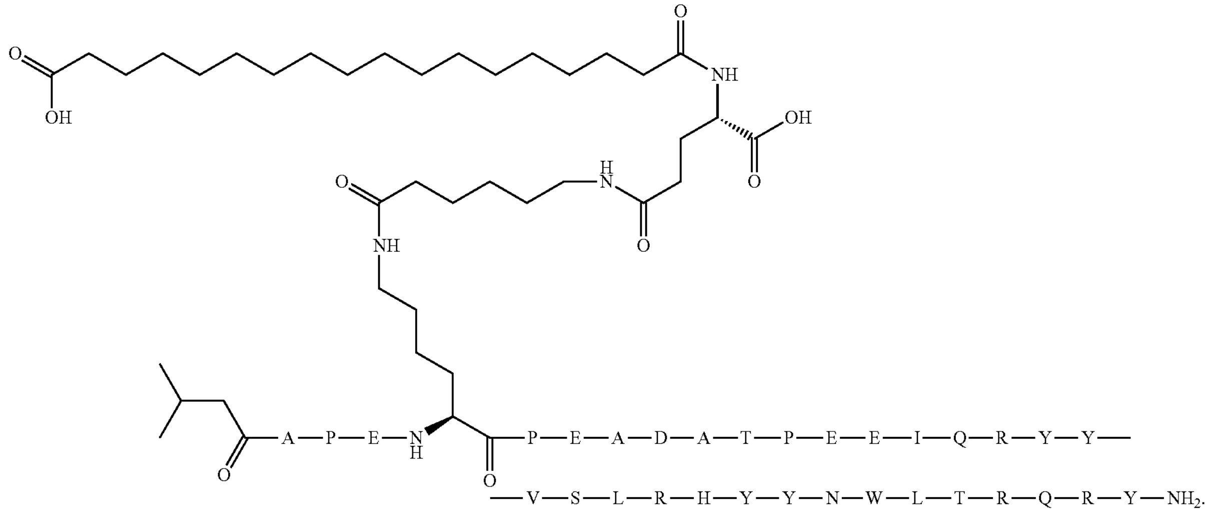
4. A PYY analogue, wherein the PYY analog is:
(SEQ ID NO: 11)
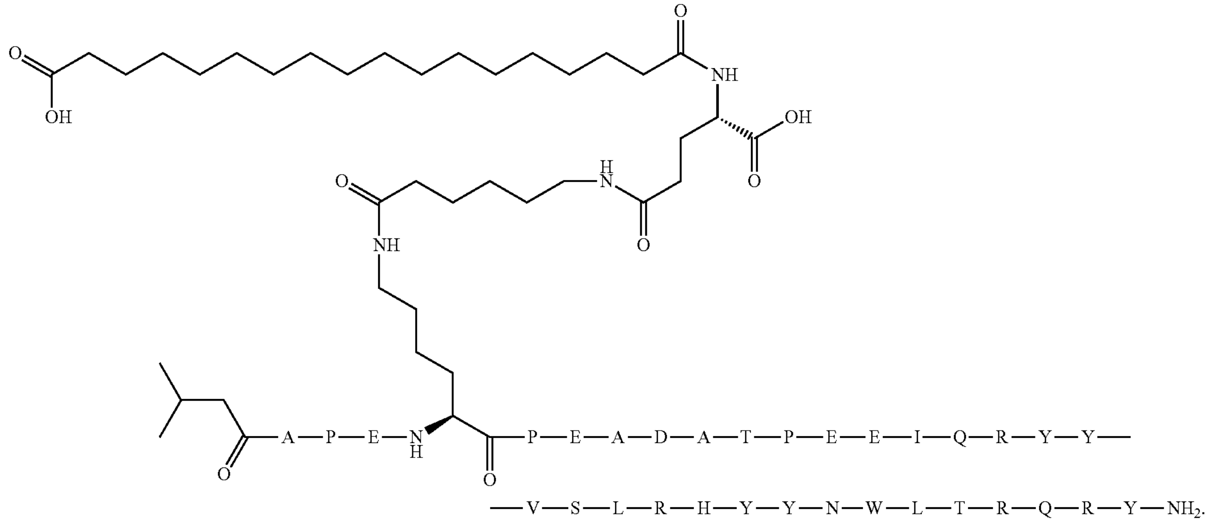

5. A PYY analogue comprising:

(SEQ ID NO: 11)

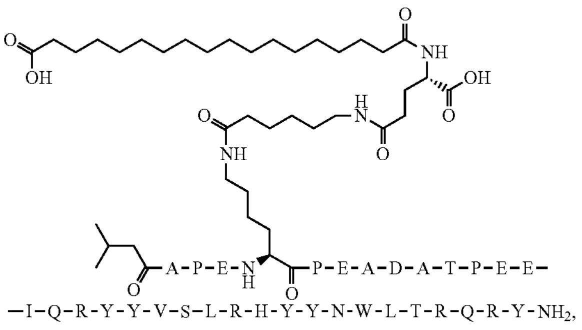

wherein the PYY analogue is in the form of a pharmaceutically acceptable salt.

6. A PYY analogue, wherein the PYY analog is:

(SEQ ID NO: 11)

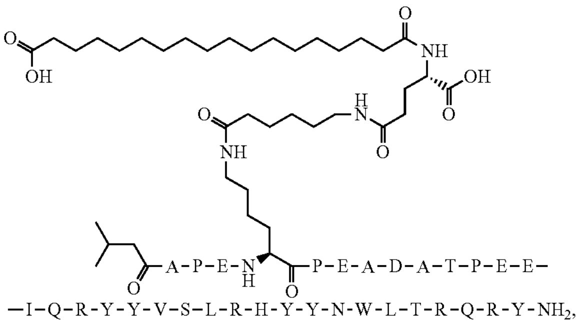

wherein the PYY analogue is in the form of a pharmaceutically acceptable salt.

7. A pharmaceutical composition comprising the PYY analogue or pharmaceutically acceptable salt thereof according to claim 1, and one or more pharmaceutically acceptable excipients.

8. A pharmaceutical composition comprising the PYY analogue or pharmaceutically acceptable salt thereof according to claim 2, and one or more pharmaceutically acceptable excipients.

9. A pharmaceutical composition comprising the PYY analogue according to claim 3, and one or more pharmaceutically acceptable excipients.

10. A pharmaceutical composition comprising the PYY analogue according to claim 4, and one or more pharmaceutically acceptable excipients.

11. A pharmaceutical composition comprising the PYY analogue according to claim 5, and one or more pharmaceutically acceptable excipients.

12. A pharmaceutical composition comprising the PYY analogue according to claim 6, and one or more pharmaceutically acceptable excipients.

13. A method for treating a condition or disease related or caused by excess body weight or excess body weight gain, the method comprising administering to a patient in need thereof a pharmaceutically effective amount of a PYY analogue according to claim 1, or a pharmaceutically acceptable salt thereof.

14. A method for treating obesity or an obesity-related condition or disease, the method comprising administering to a patient in need thereof a pharmaceutically effective amount of a PYY analogue according to claim 1, or a pharmaceutically acceptable salt thereof, wherein the obesity or the obesity-related condition or disease is selected from the group consisting of type 2 diabetes, hypertension, dyslipidemia, sleep apnea and cardiovascular disease.

15. A method for treating atherogenic dyslipidemia, hepatic steatosis, non-alcoholic fatty liver disease (NAFLD), non-alcoholic steatohepatitis (NASH), kidney failure or atherosclerosis, the method comprising administering to a patient in need thereof a pharmaceutically effective amount of a PYY analogue according to claim 1, or a pharmaceutically acceptable salt thereof.

16. The method according to claim 13, wherein the PYY analogue is administered as part of a combination therapy together with an agent for treatment of diabetes, obesity, dyslipidemia or hypertension.

17. The method according to claim 14, wherein the PYY analogue is administered as part of a combination therapy together with an agent for treatment of diabetes, obesity, dyslipidemia or hypertension.

18. The method according to claim 15, wherein the PYY analogue is administered as part of a combination therapy together with an agent for treatment of diabetes, obesity, dyslipidemia or hypertension.

* * * * *